(12) United States Patent
Patel et al.

(10) Patent No.: US 9,451,950 B2
(45) Date of Patent: Sep. 27, 2016

(54) APPARATUS AND METHOD FOR FASCIAL CLOSURE DEVICE FOR LAPAROSCOPIC TROCAR PORT SITE AND SURGERY

(71) Applicants: Manoj B Patel, Lumberton, NJ (US); Philip Zhao, Fort Lee, NJ (US); Neal Patel, North Brunswick, NJ (US); Landon Gilkey, Austin, TX (US); David M. Albala, Manlius, NY (US); Salvatore Castro, Raliegh, NC (US)

(72) Inventors: Manoj B Patel, Lumberton, NJ (US); Philip Zhao, Fort Lee, NJ (US); Neal Patel, North Brunswick, NJ (US); Landon Gilkey, Austin, TX (US); David M. Albala, Manlius, NY (US); Salvatore Castro, Raliegh, NC (US)

(*) Notice: Subject to any disclaimer, the term of this patent is extended or adjusted under 35 U.S.C. 154(b) by 0 days.

(21) Appl. No.: 14/284,456

(22) Filed: May 22, 2014

(65) Prior Publication Data

US 2014/0350576 A1   Nov. 27, 2014

Related U.S. Application Data

(60) Provisional application No. 61/826,058, filed on May 22, 2013, provisional application No. 61/837,114, filed on Jun. 19, 2013, provisional application No. 61/873,325, filed on Sep. 3, 2013.

(51) Int. Cl.
*A61B 17/04* (2006.01)
*A61B 17/00* (2006.01)

(52) U.S. Cl.
CPC ....... *A61B 17/0482* (2013.01); *A61B 17/0057* (2013.01); *A61B 17/0469* (2013.01); *A61B 2017/00623* (2013.01); *A61B 2017/00637* (2013.01); *A61B 2017/00659* (2013.01); *A61B 2017/00663* (2013.01); *A61B 2017/047* (2013.01); *A61B 2017/0472* (2013.01)

(58) Field of Classification Search
CPC .......... A61B 17/0469; A61B 17/0482; A61B 17/0474; A61B 2017/0472; A61B 17/3403; A61B 2017/3405; A61B 2017/3407
See application file for complete search history.

(56) References Cited

U.S. PATENT DOCUMENTS

| 5,364,365 | A  | * | 11/1994 | Wortrich | 604/158 |
|---|---|---|---|---|---|
| 2004/0092964 | A1 | * | 5/2004 | Modesitt et al. | 606/144 |
| 2004/0249393 | A1 | * | 12/2004 | Weisel et al. | 606/144 |
| 2005/0228405 | A1 | * | 10/2005 | Maruyama et al. | 606/144 |

FOREIGN PATENT DOCUMENTS

WO   PCT/US14/43274   12/2014

* cited by examiner

*Primary Examiner* — Diane Yabut
(74) *Attorney, Agent, or Firm* — Rick B. Yeager

(57) ABSTRACT

A suture placement device is inserted into an endoscopic trocar port site. A pivot bar with a pair of receptor ports is moved from a folded to an extended position below the fascia. The trocar port is removed over the device as the pivot bar is pulled upward against the fascia. A pair of stylet guides are deployed from two sides of the device housing, and intercept the receptor ports, thereby creating a suture path through the first guide, through a channel in the pivot bar between the receptor ports, and through the second guide. A stylet is directed through the suture path to pull a suture through the path. The guides are refracted, the pivot bar is folded, the device is removed, and the suture is tied. A stylet guide may have a partially deployed position to accurately inject an anesthetic at a desired intra-muscular layer.

19 Claims, 60 Drawing Sheets

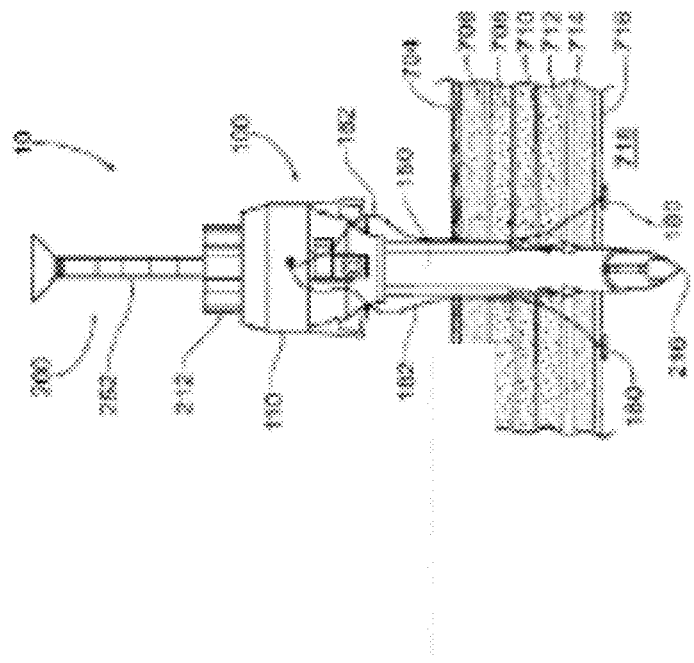
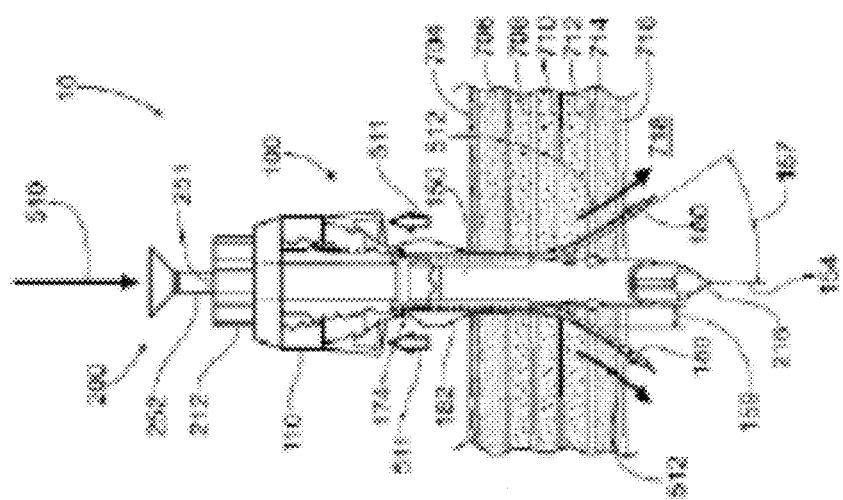

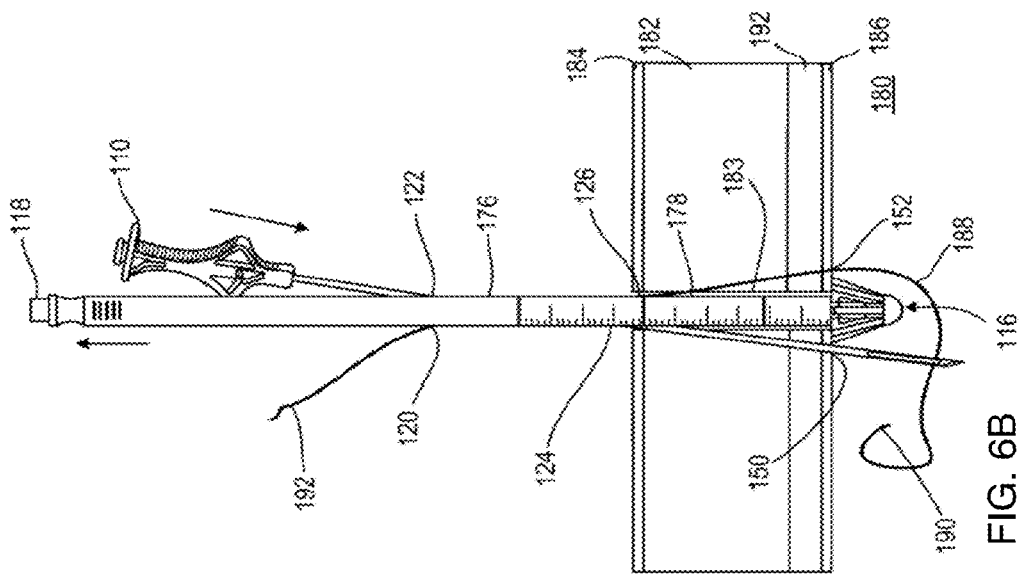
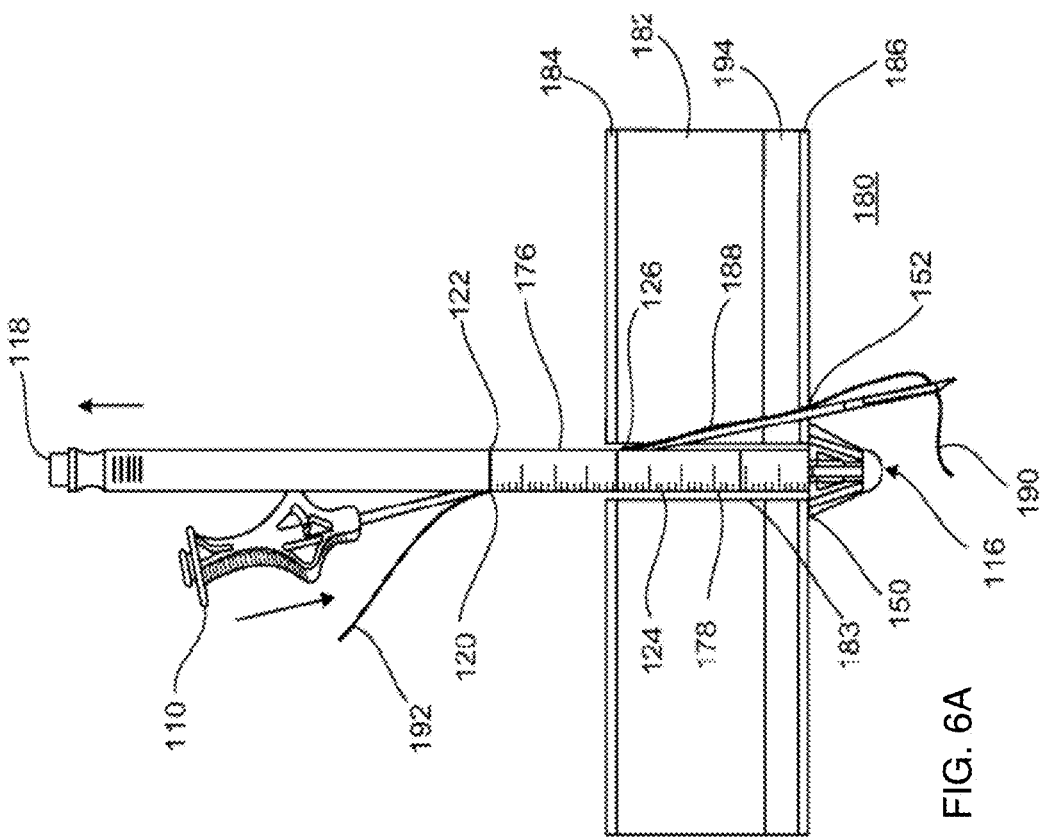

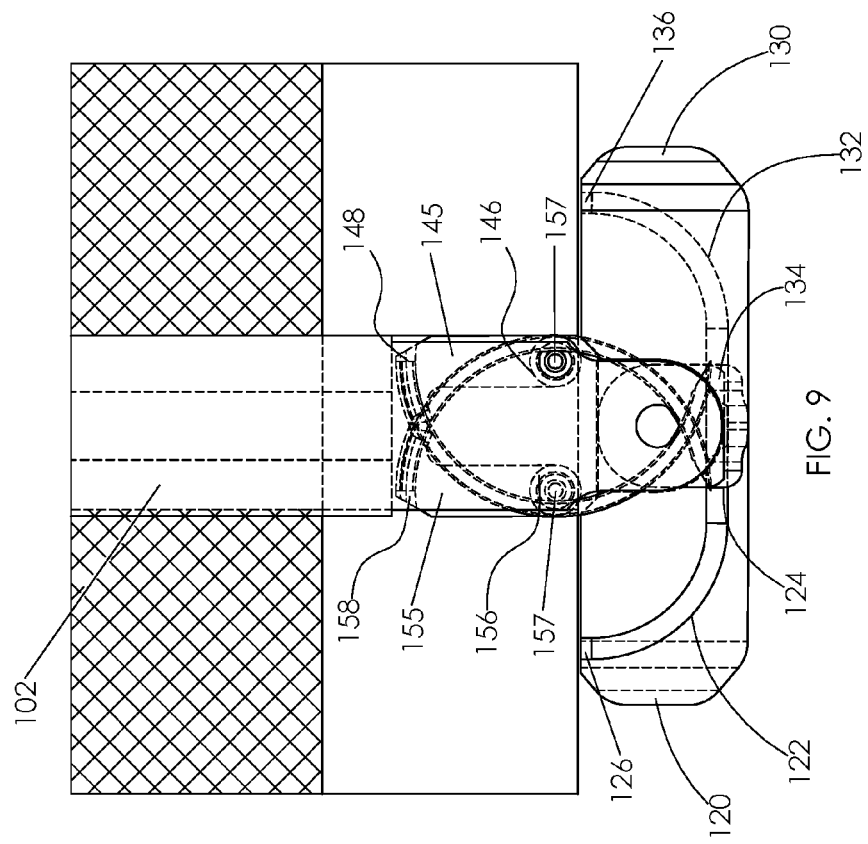
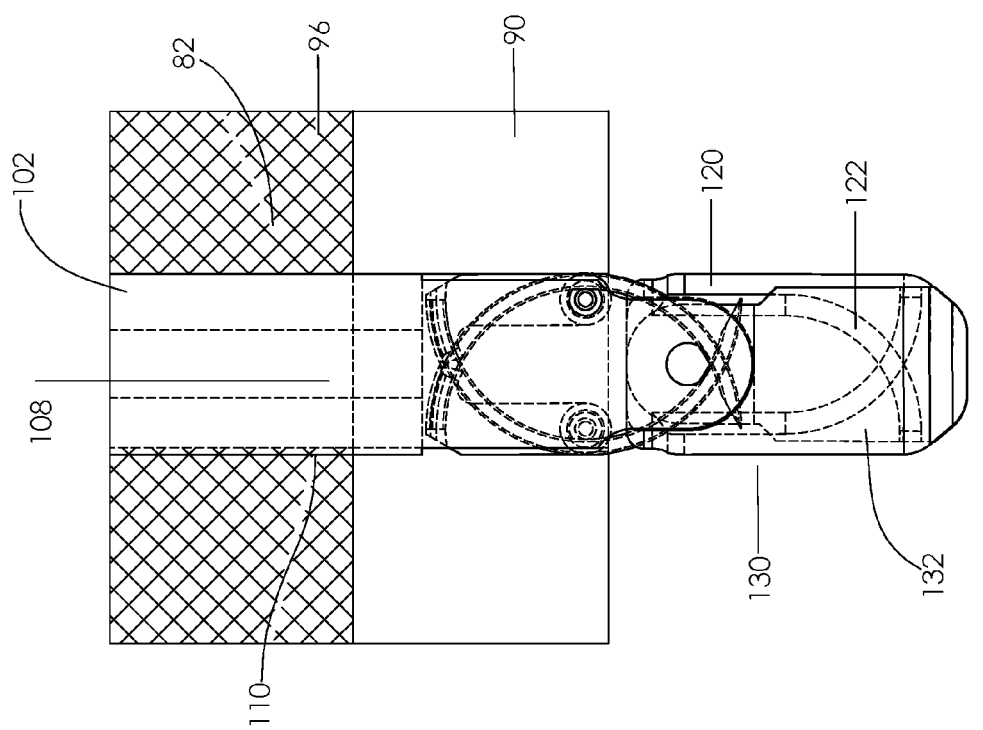

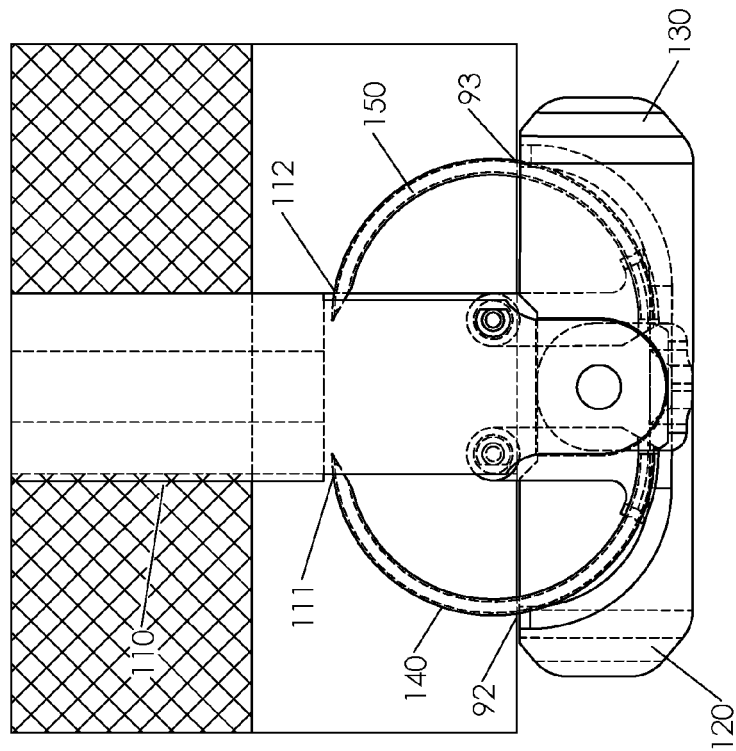
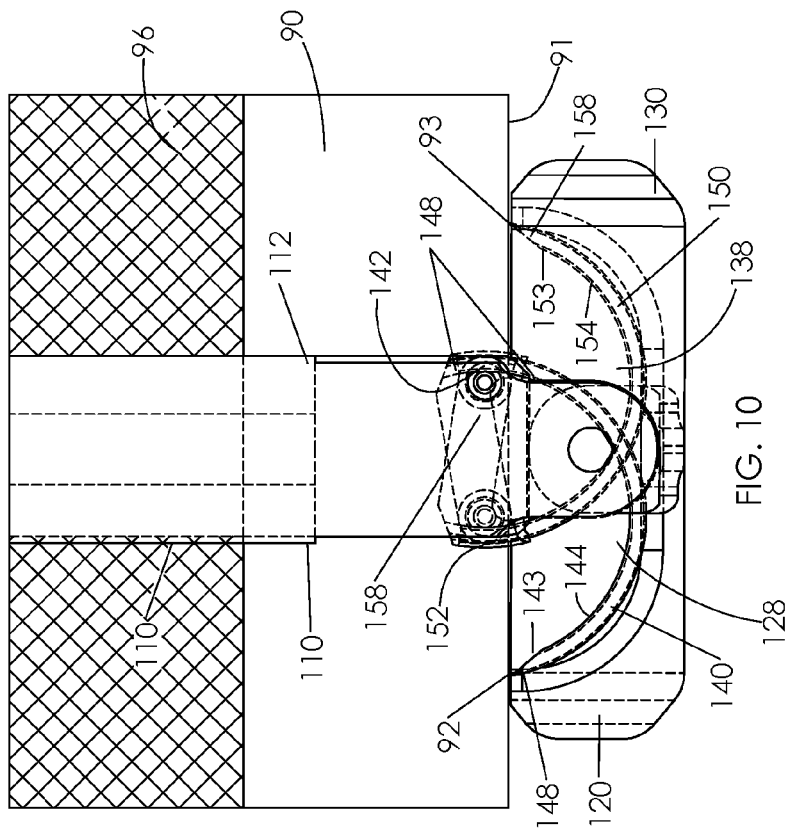

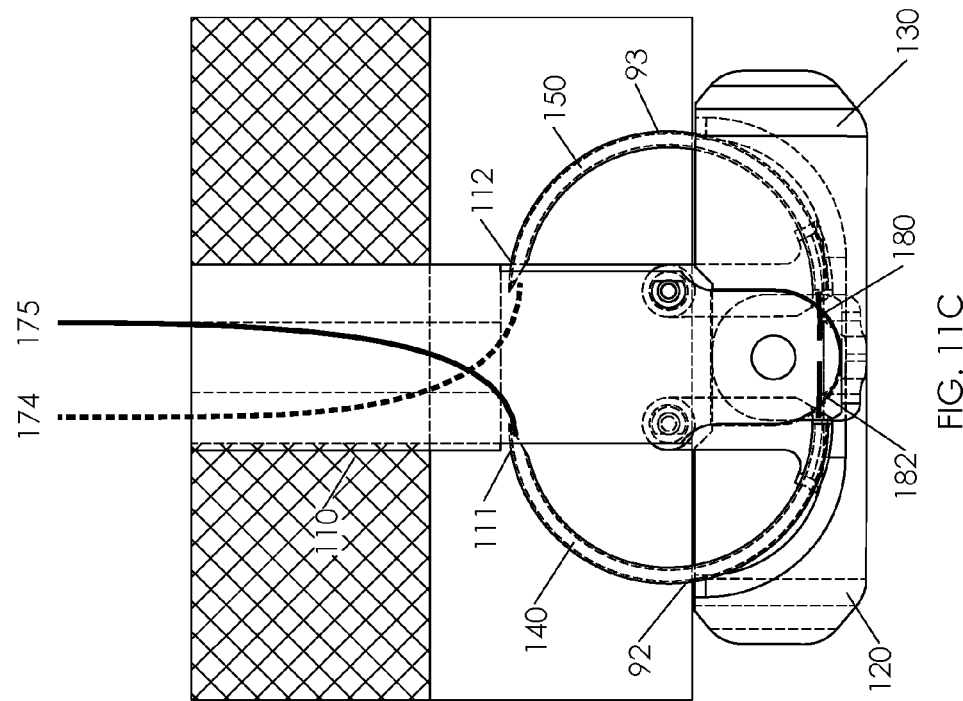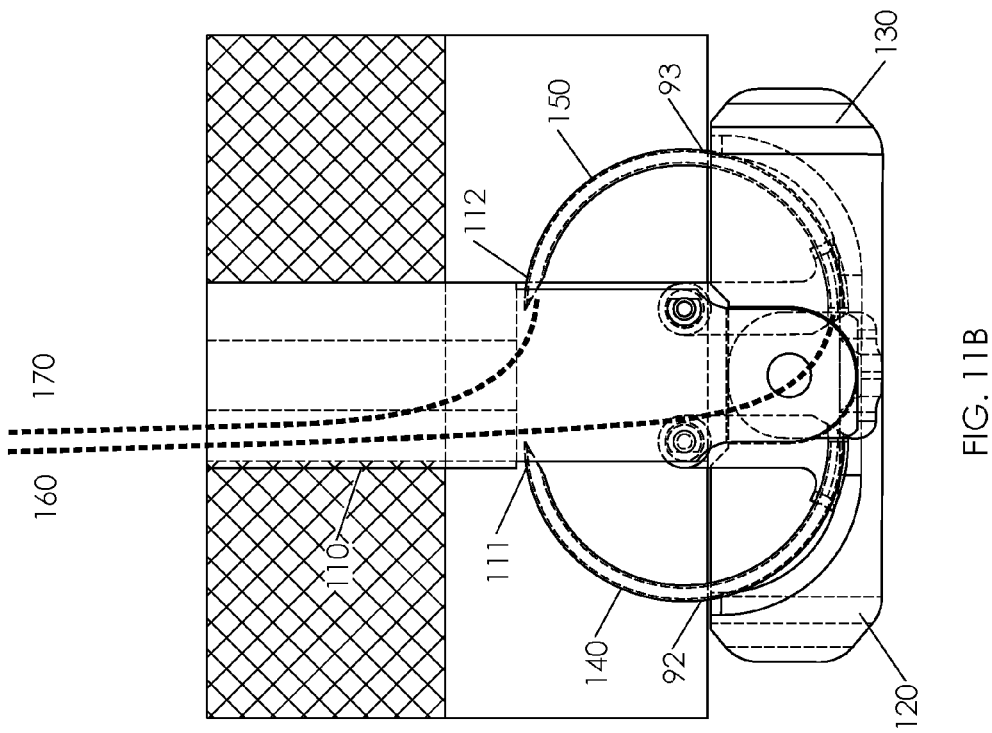

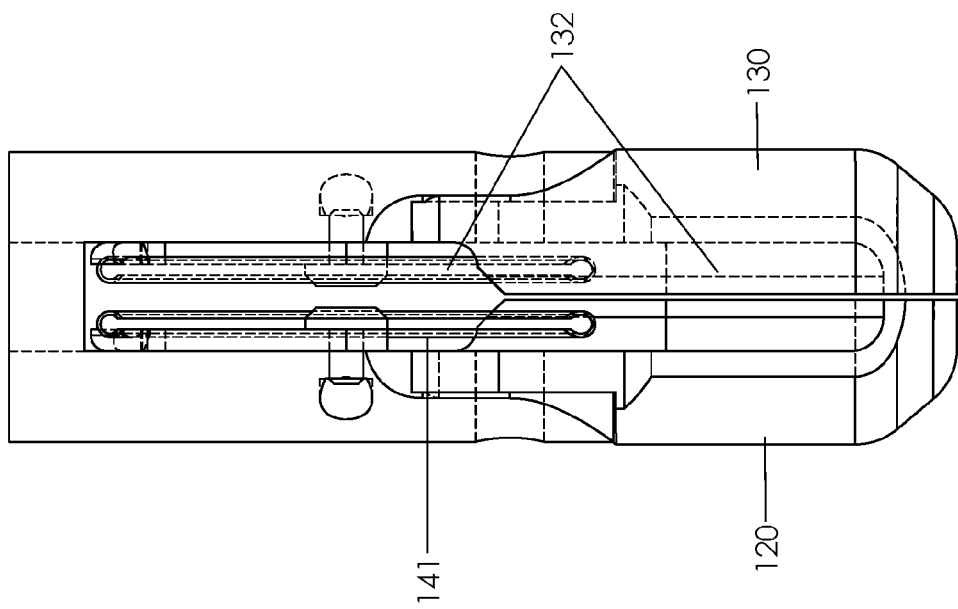
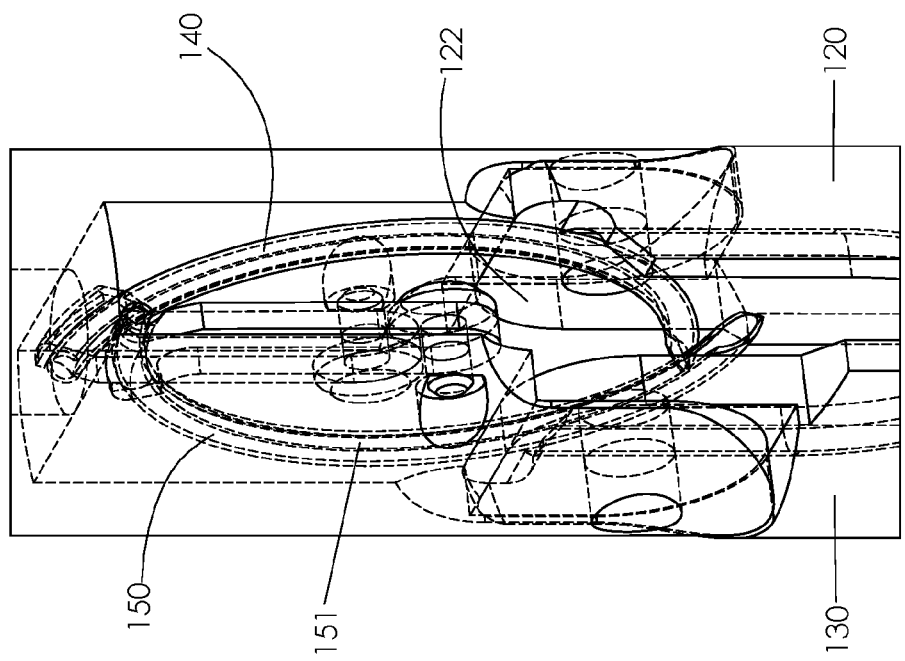
FIG. 13
FIG. 12

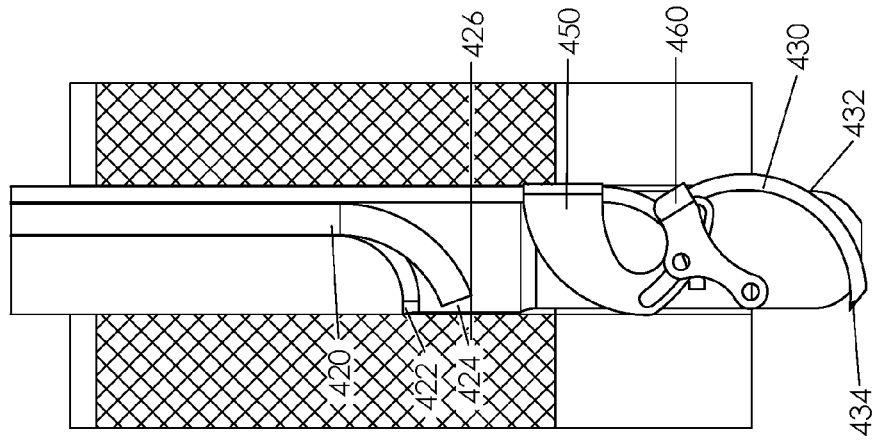

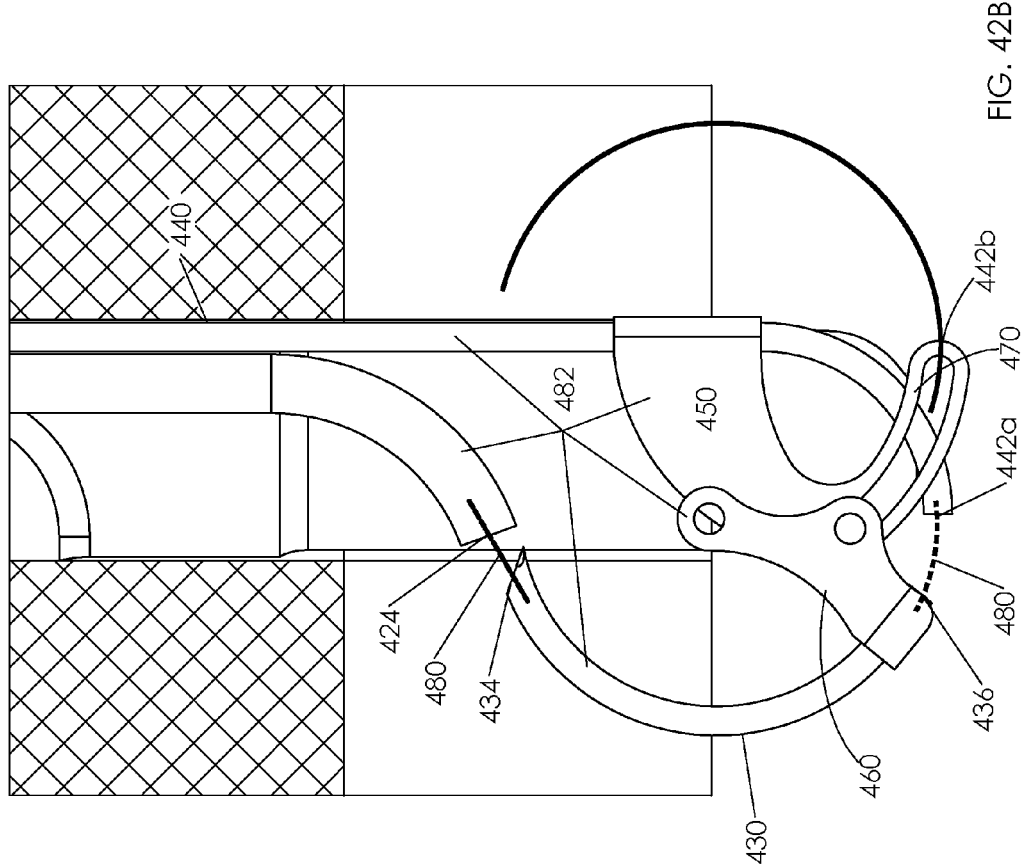

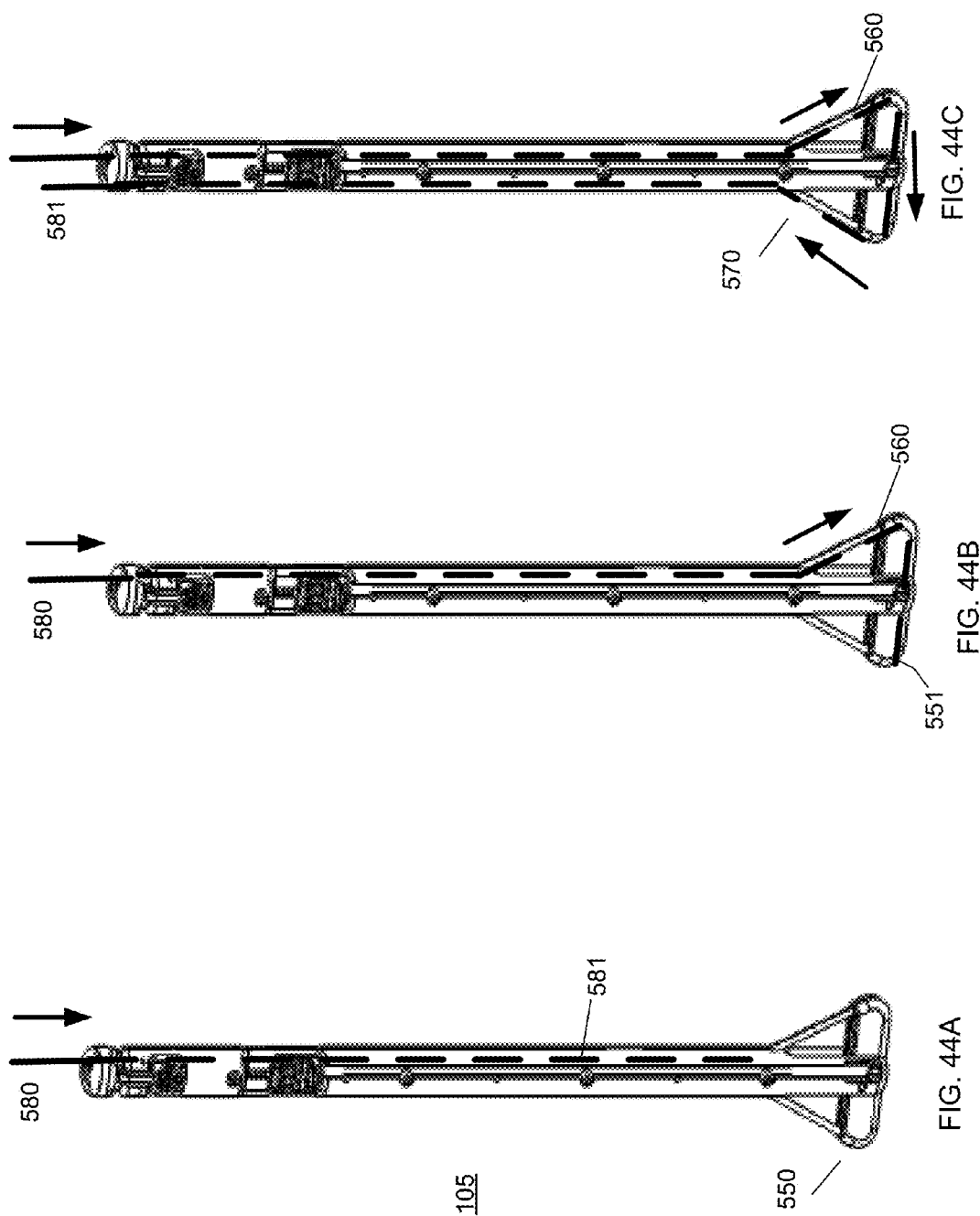

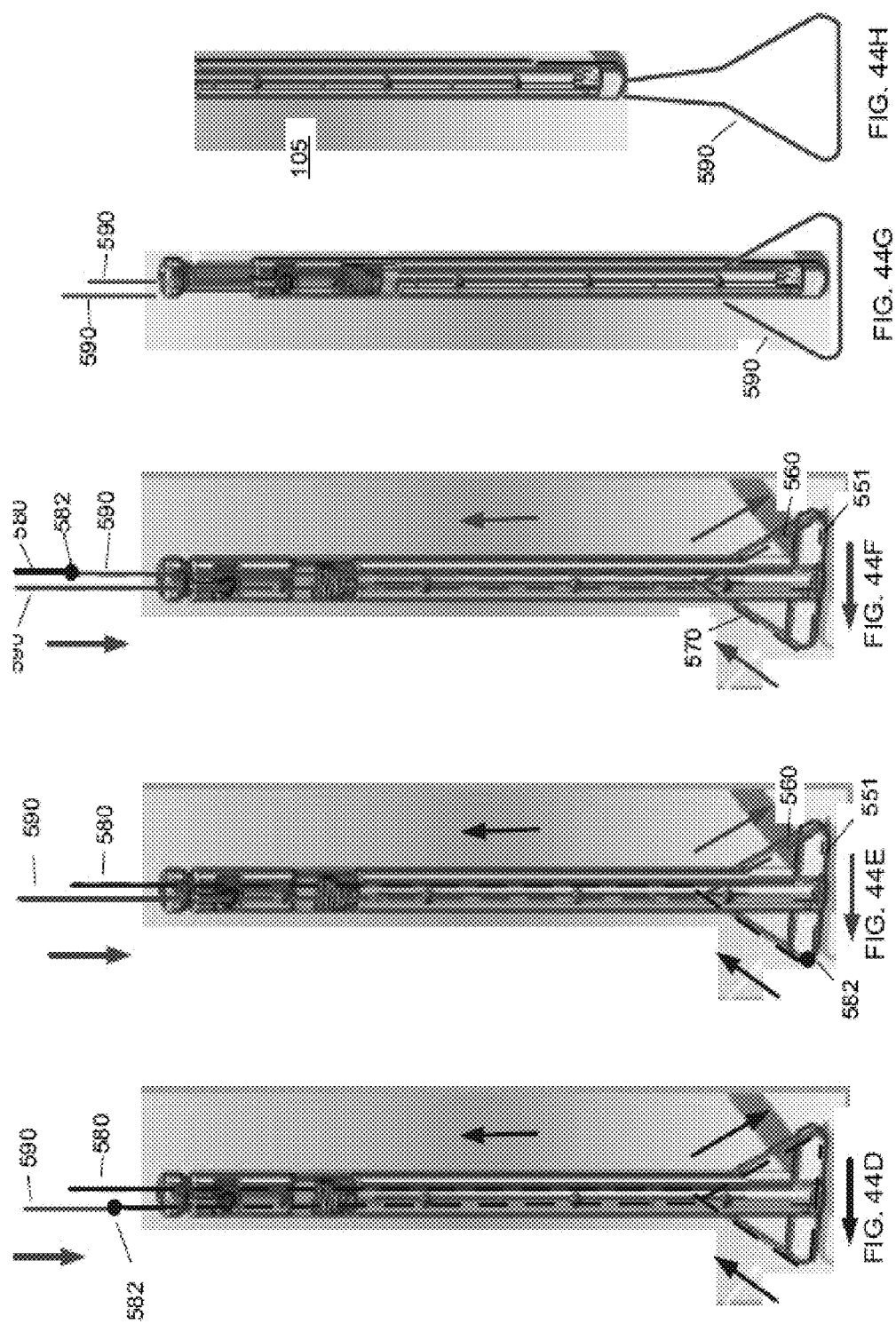

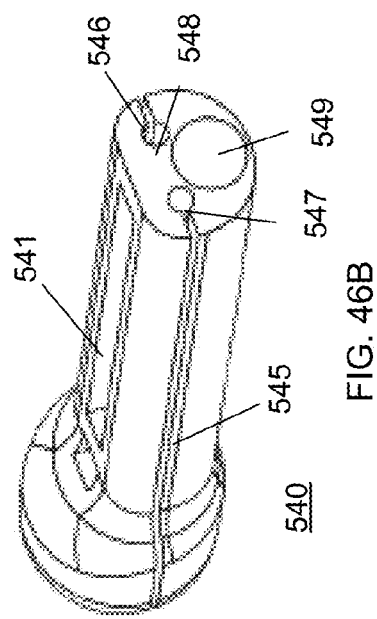
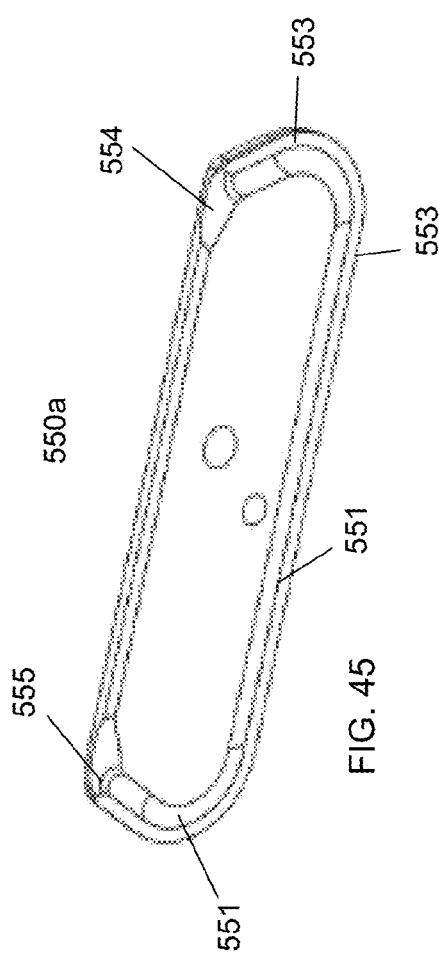
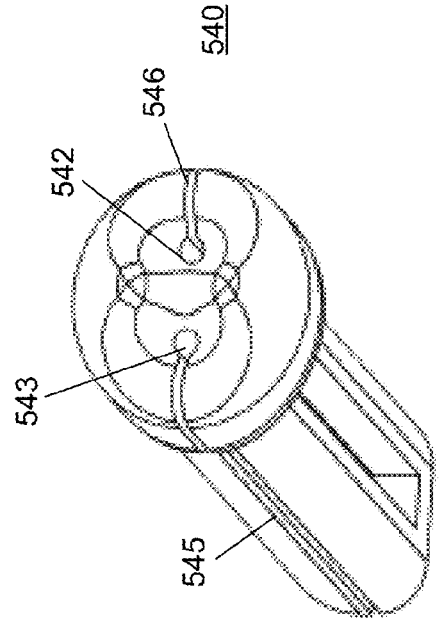
FIG. 45
FIG. 46A
FIG. 46B

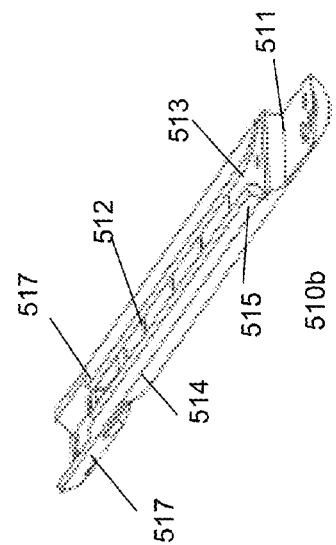
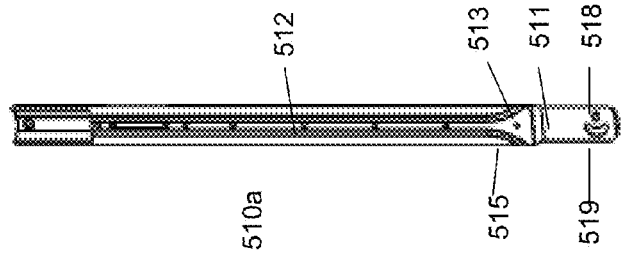
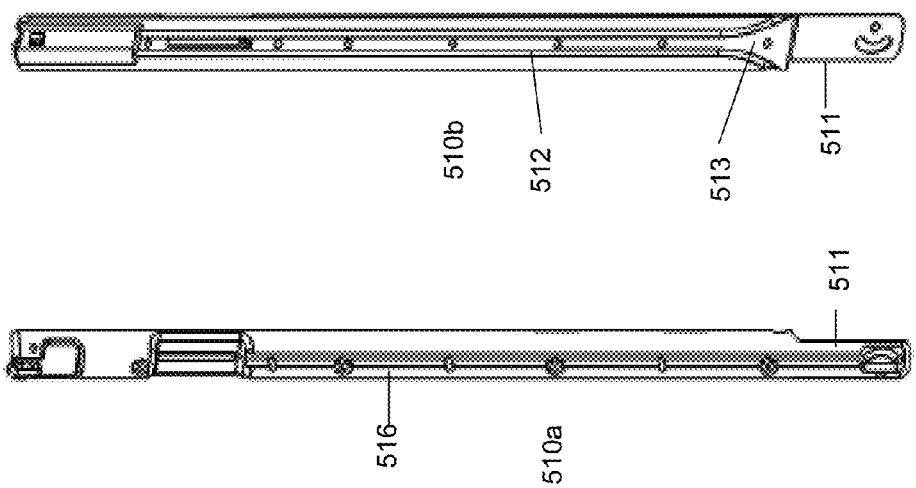

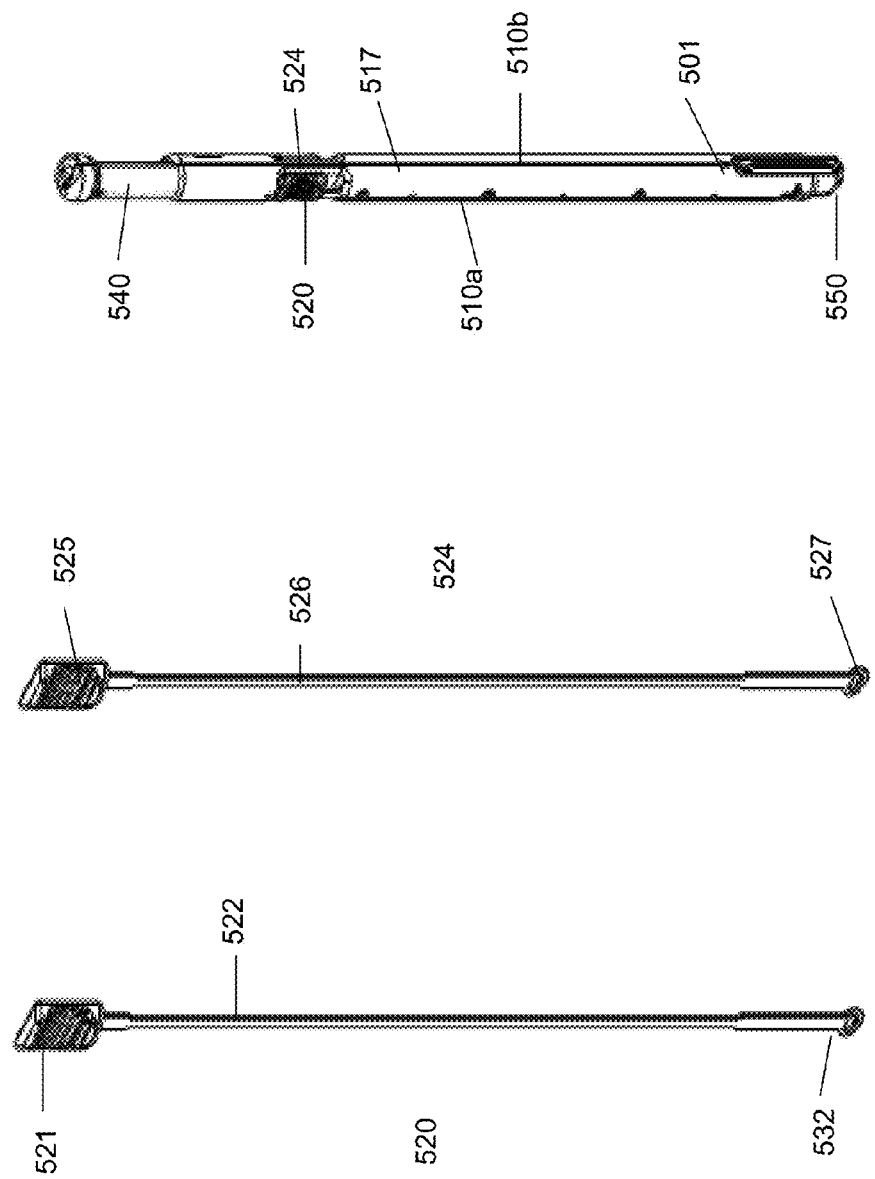

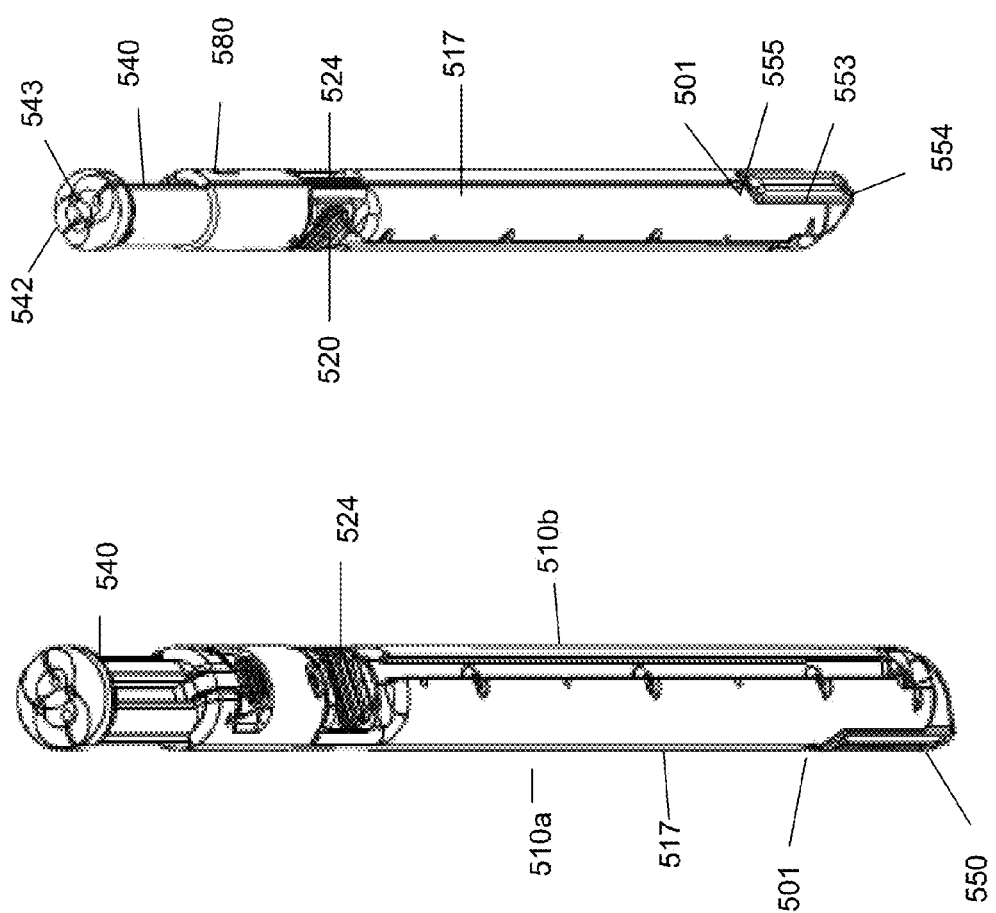

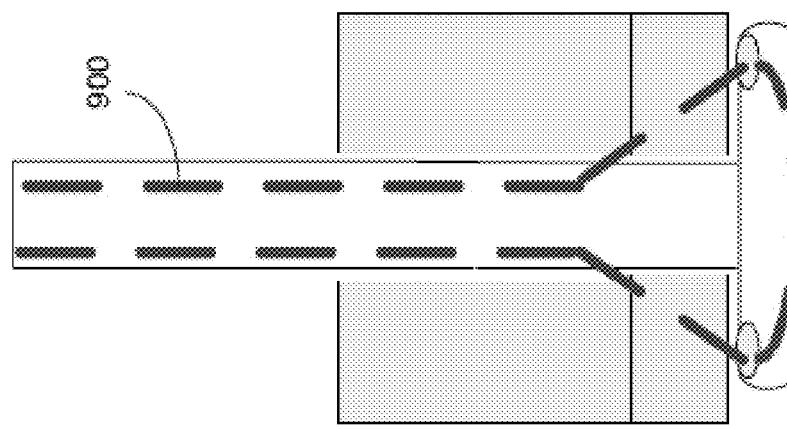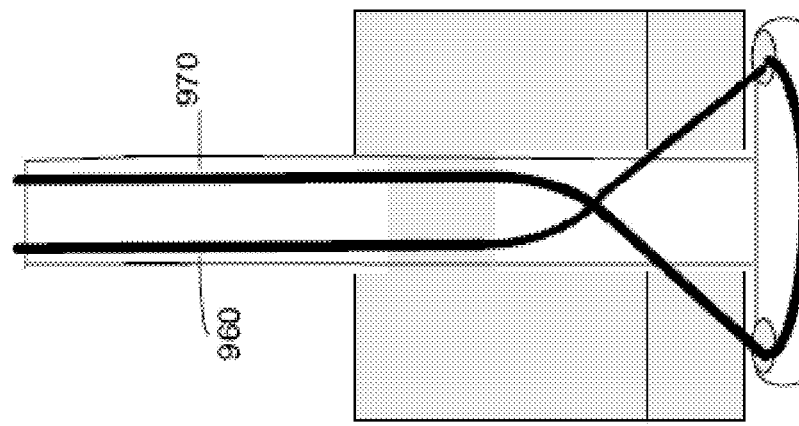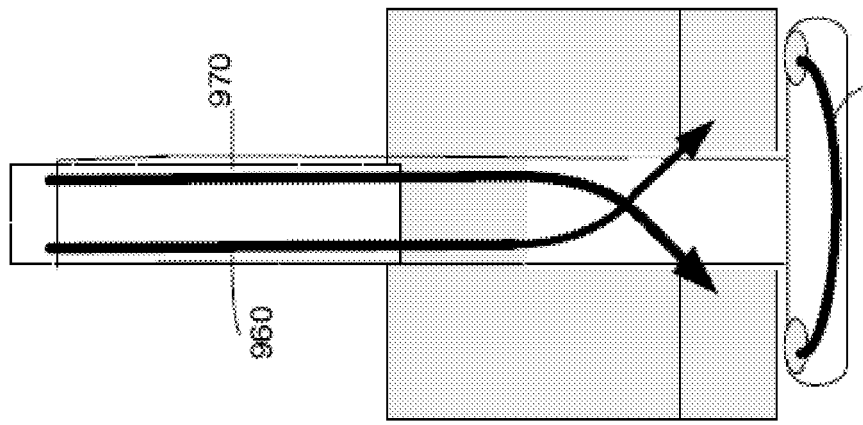

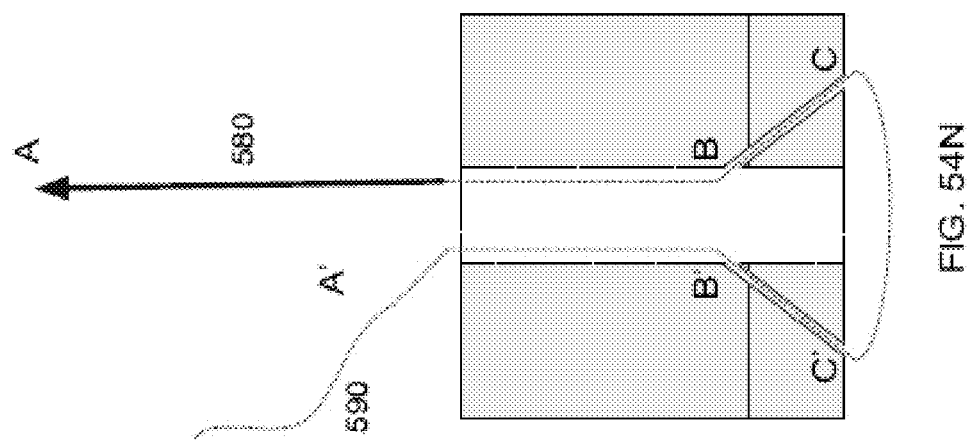
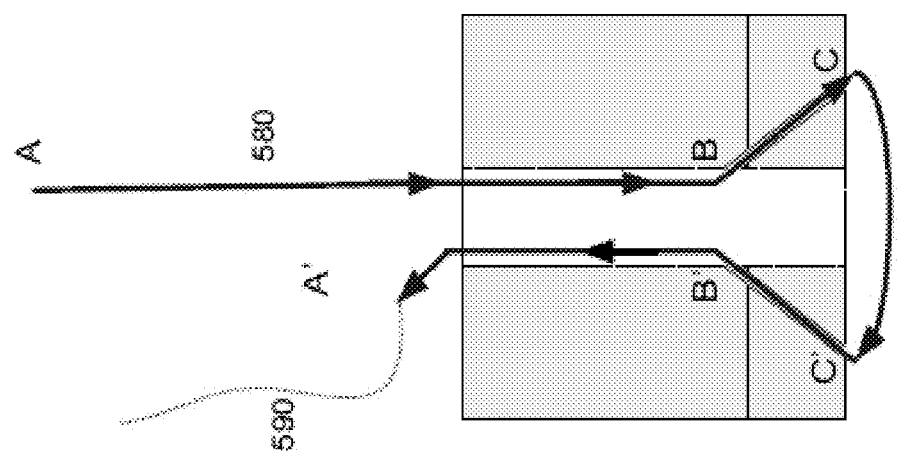

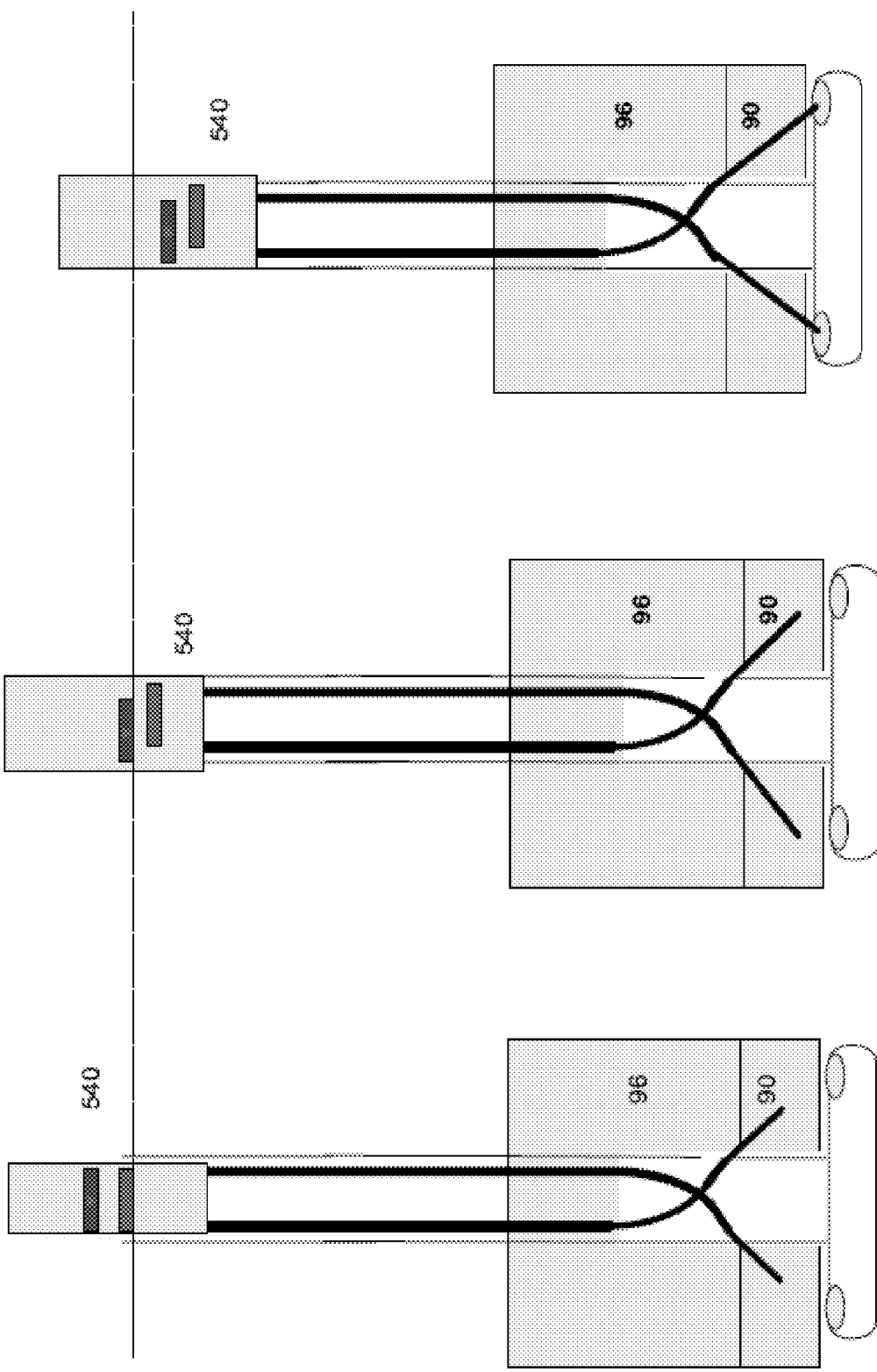

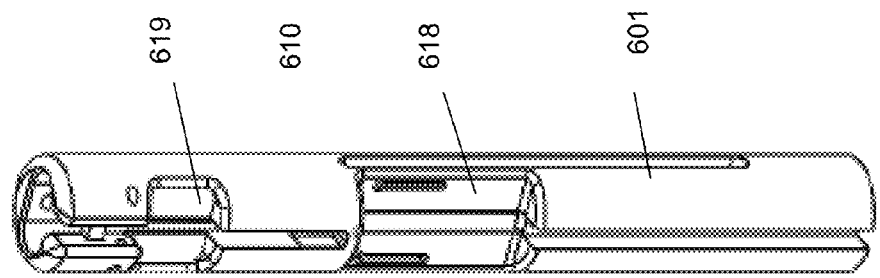
FIG. 66
FIG. 65
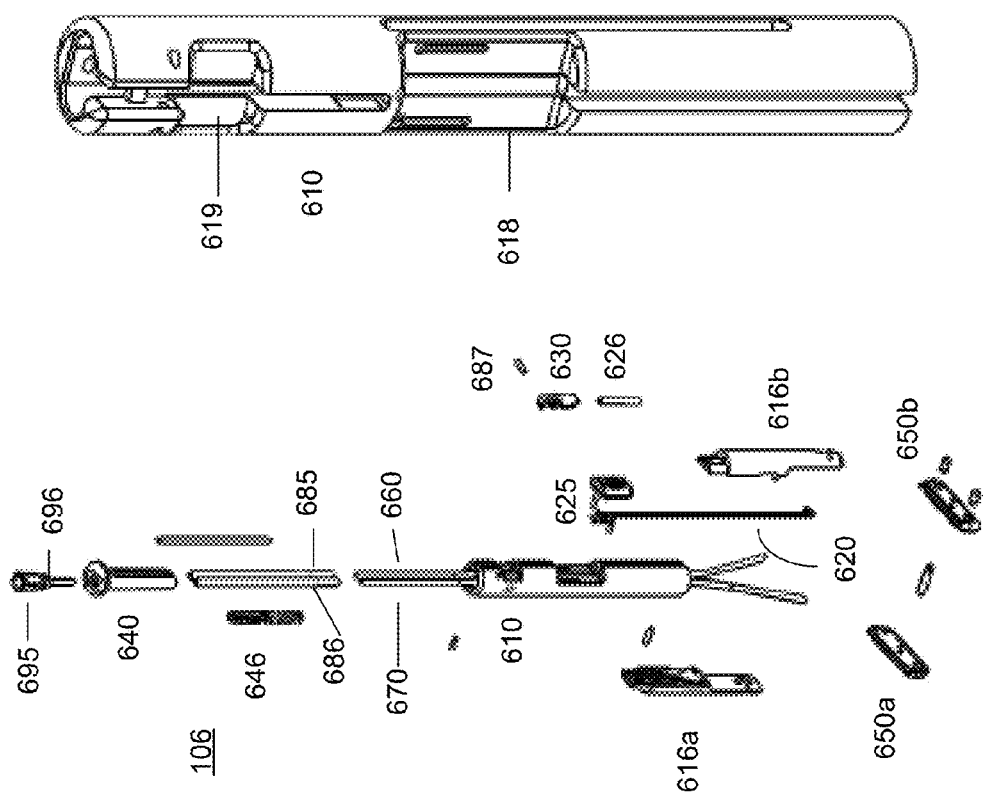
FIG. 64

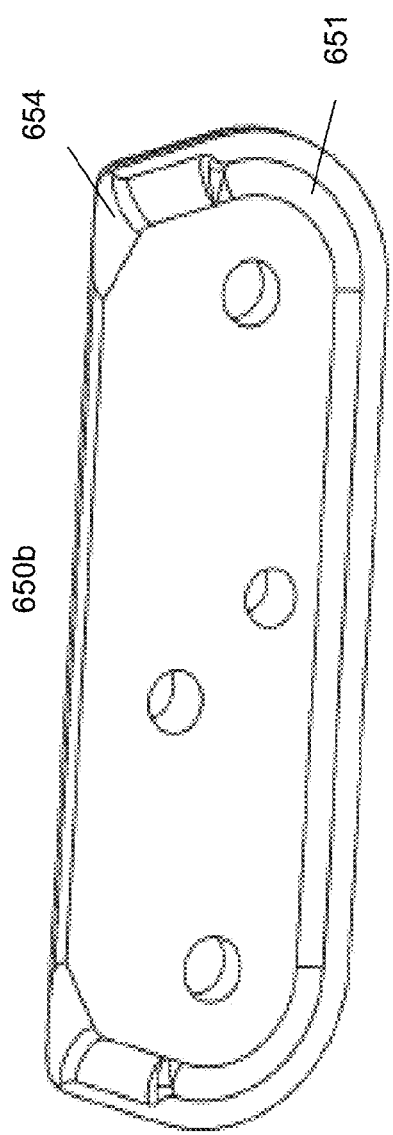
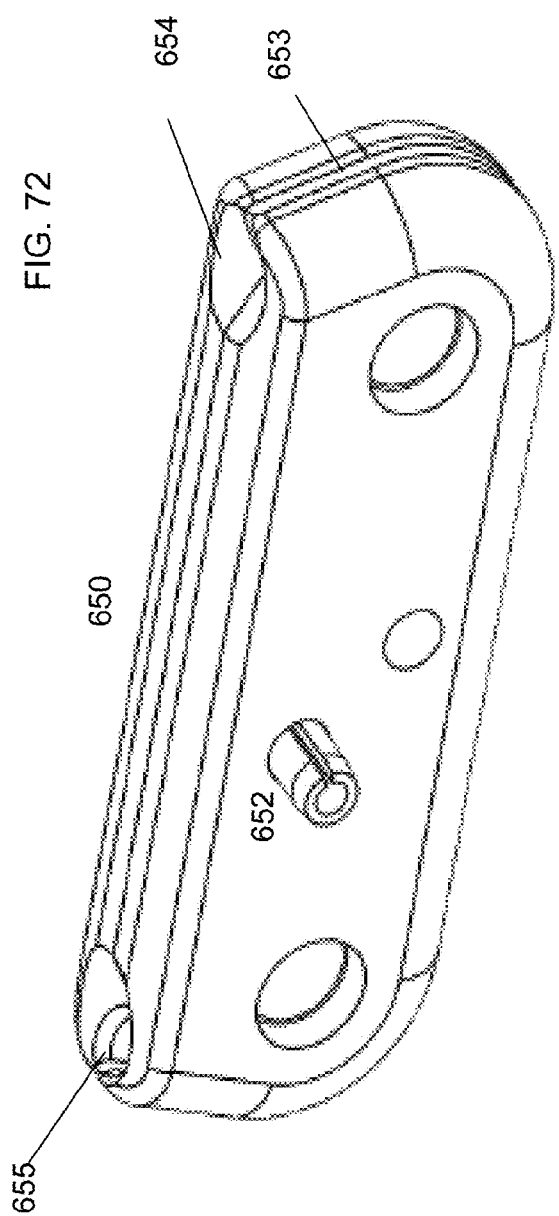
FIG. 72
FIG. 73

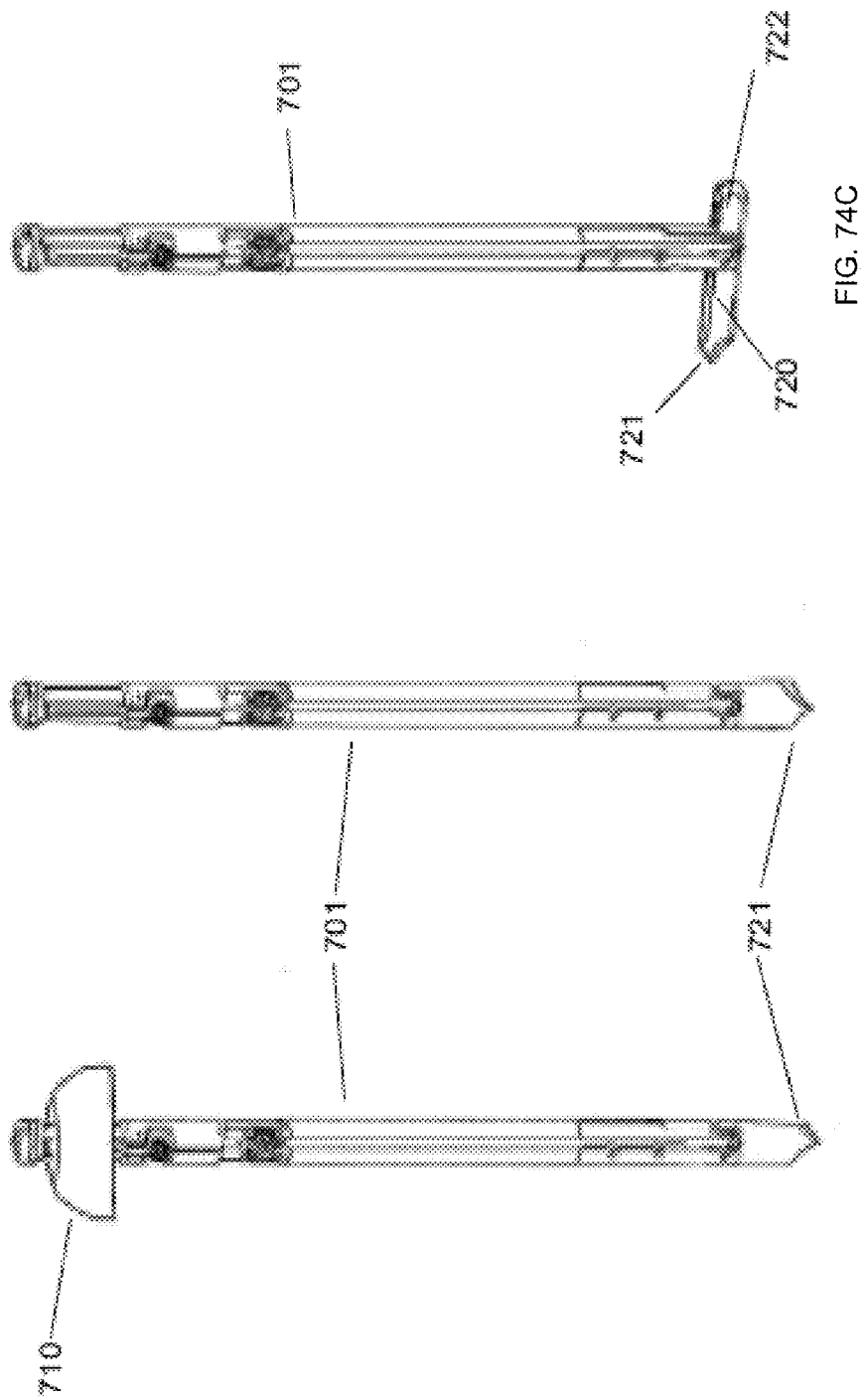

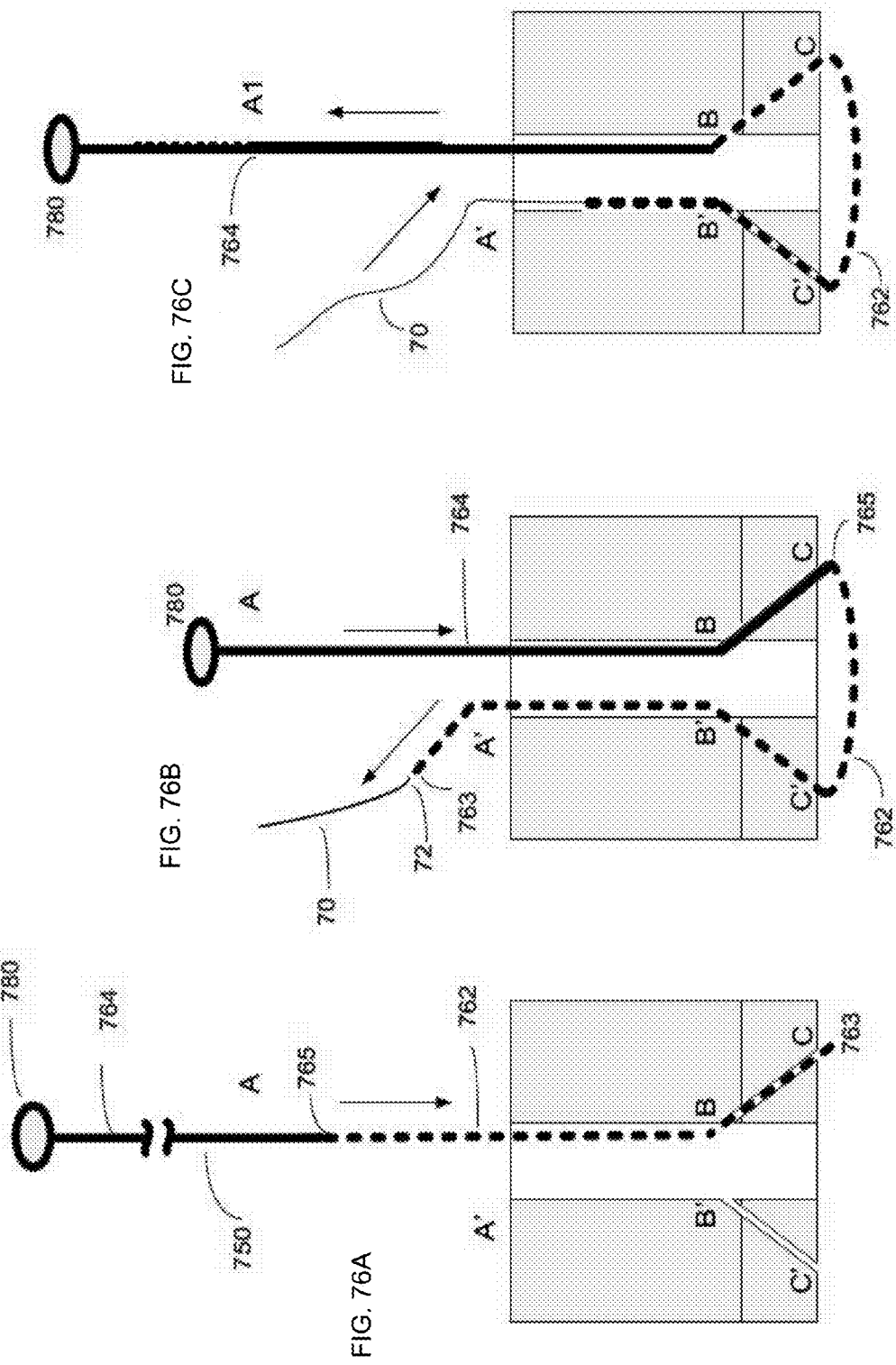

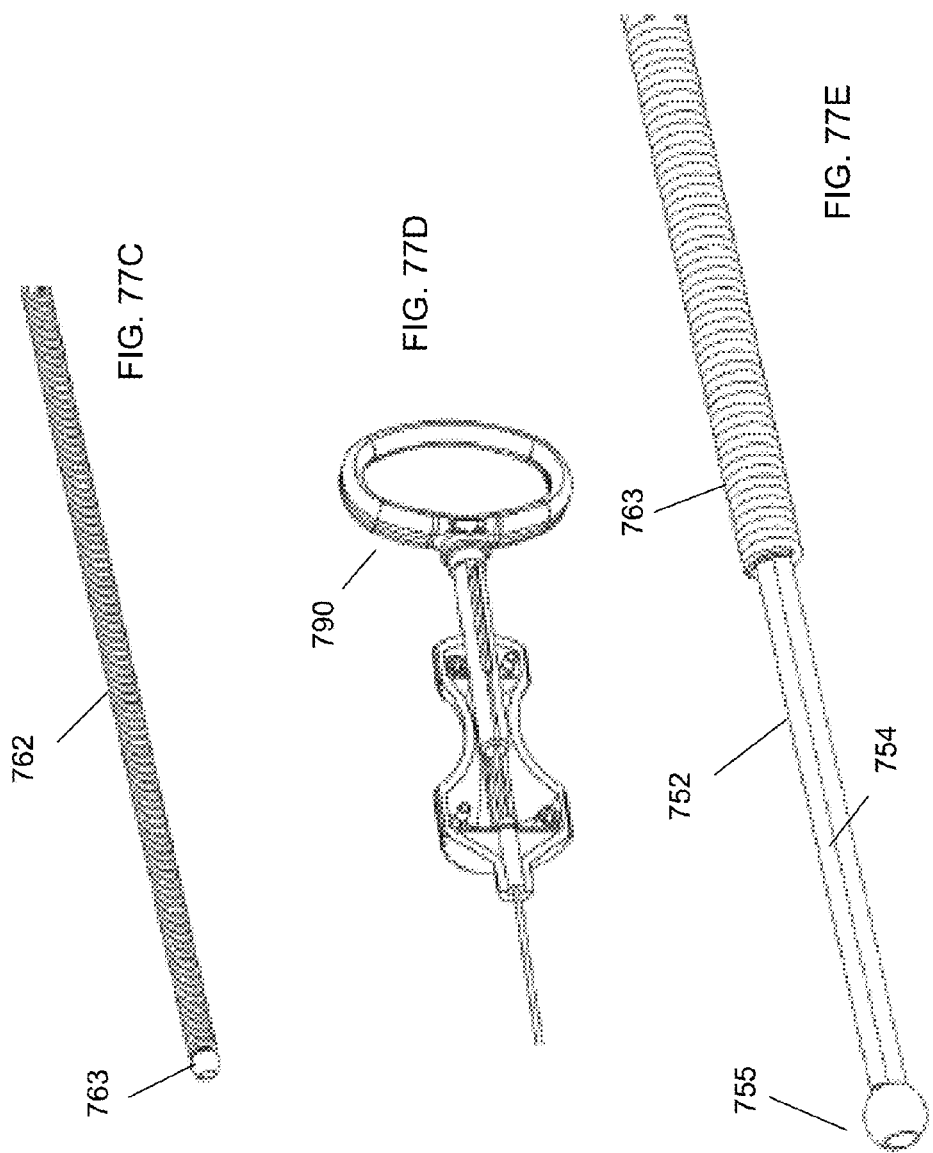

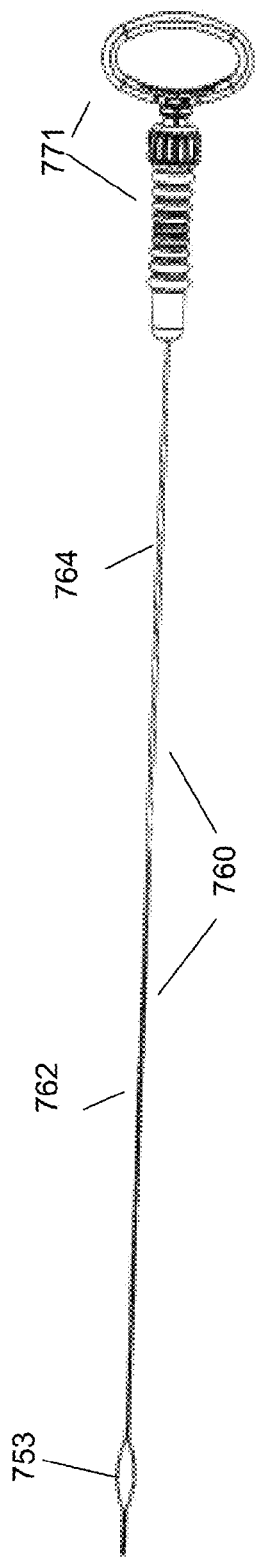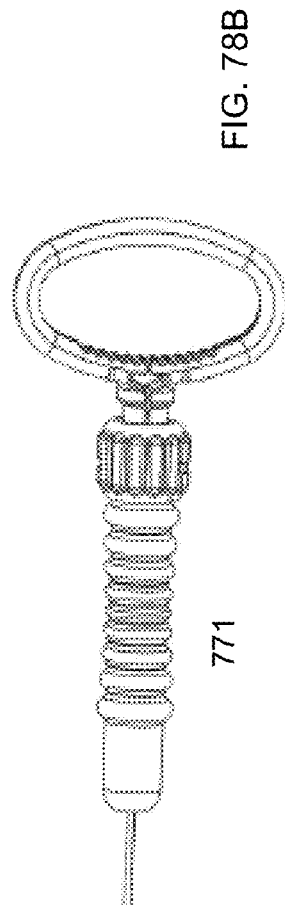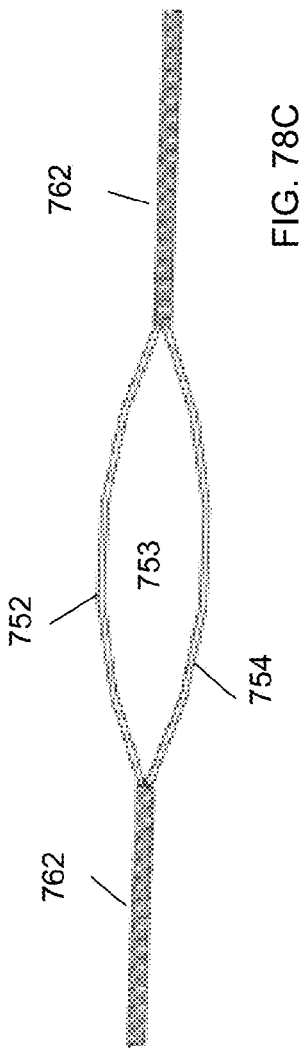

APPARATUS AND METHOD FOR FASCIAL CLOSURE DEVICE FOR LAPAROSCOPIC TROCAR PORT SITE AND SURGERY

RELATED APPLICATIONS

This US non-provisional patent application is related to U.S. Provisional Patent Application No. 61/826,058 filed May 22, 2013, which is incorporated by reference, and claims the benefit of that filing date. This patent application is also related to U.S. Provisional Patent Application No. 61/837,114 filed Jun. 19, 2013 and U.S. Provisional Patent Application No. 61/873,325 filed Sep. 3, 2013, both incorporated by reference, and claims the benefit of those filing dates.

BACKGROUND

1. Field of Invention

This invention generally relates to laparoscopic surgery and trocar port placement. More particularly, the invention relates to tissue closure devices, including surgical suturing devices as well as such devices that can be used for intra-abdominal suturing and suturing of puncture wounds generated by surgical laparoscopic trocar ports and other puncturing devices.

2. Prior Art

Apparatus and methods are provided for treating tissue opening, for example an endoscopic trocar port opening used in a minimally invasive surgical procedure. A suture placement device is provided to rapidly, safely, efficiently and effectively close tissue defects created to access the intra-abdominal cavity during laparoscopic surgical procedures in a human body. The device as described is able to obtain adequate tissue adjacent to the tissue defect to provide a strong closure, to maintain pneumoperitoneum needed for appropriate visualization of the peritoneal contents during the closure process, and to protect the vital structures within the abdominal cavity in the vicinity and the healthcare provider for risk of injury.

The prior art discloses various methods of routing and presenting a suture so that suture ends can be tied to close an opening in tissue after a cannular device is removed from the tissue. Representative prior art devices are discussed below and shown in FIGS. 1-6.

FIGS. 1A-1B show a prior art device of U.S. Pat. No. 7,060,077 to Gordon et al. In one embodiment provides needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the selected tissue, for example, in the interior wall of the body cavity. The needles are removed from the ends of the suture, and the suture material is tied to complete the approximation of the tissue.

FIG. 2 is a prior art device described in US Patent Application No. 20120035623 to Bagaoisan et al. In one example, a closure device includes a longitudinally extending body having a proximal portion and a distal portion. The distal portion includes a suture holding portion extending a first distance laterally from a first axial position on the body. The body further includes a substantially straight, suture-receiving passageway extending at an angle to a central axis of a body. The passageway includes an entrance opening and an exit opening on the body distal of the entrance opening and it is substantially aligned with the suture holding portion. The exit opening on the body is positioned proximally at a second axial position relative to the first axial position and spaced therefrom a second distance.

FIG. 3 is a prior art device described in US Patent Application No. 2008/0033459 to 20080033459 to Shafi et al. The physician then uses a needle actuator to drive two diametrically opposed flexible nitinol needles housed in the shaft of the instrument out of the ports on the body of the device. The flexible needles are driven in opposite directions through the tissue layers the physician is interested in closing, towards the distal ends of the pivoting extensions. The flexible needles are driven out at a predetermined height and angle to ensure that an adequate amount of tissue is used to close the tissue defect. The flexible needles need to be flexible enough to be manipulated within the body of the device and driven to an adequate distance away from the body of the device to obtain enough tissue for a strong closure. The flexible needles are also configured to have the appropriate stiffness to pierce through the tissue of interest without buckling. The flexible needles will be driven into the coupling channel to be received in the pivoting extensions by a set of couplers attached to the same suture that would be used otherwise to close the port sites. The distal ends of the flexible needles are configured to mate with the couplers and pull the suture back through the tissue adjacent to the tissue defect. The physician then releases the lock on the pivoting extensions and uses the pivoting extension actuator to bring the pivoting extensions back into profile with the body. The device is then pulled out of the tissue defect, leaving a looped suture through the tissue adjacent to the tissue defect. The physician can then tie the sutures as he or she would normally do in the standard procedure.

FIGS. 4A and 4B are a prior art device shown in U.S. Pat. No. 8,109,943 to Boraiah et al. The patent describes systems and methods for suture anchor deployment. A trocar port system includes a cannula assembly and an obturator assembly, the cannula assembly providing a needle assembly and the obturator assembly providing a needle actuation mechanism. The obturator assembly may be at least partially inserted into the cannula assembly and arranged to operatively couple the needle actuation mechanism to the needle assembly. The needle assembly includes at least one needle, each needle having disposed near its distal tip a suture anchor. A method includes steps for deploying and/or depositing at least one suture anchor in or through an organ of the human body.

FIGS. 5A and 5B are illustrations of a portion of a prior art Neat Stitch™ closure device showing a pair of needle guides which are released from a cartridge and positioned against the bottom of the fascia. The needle guides contain needles (not shown). As the needles are released and forced through the fascia and into the shaft of the device, a pre-loaded suture is routed through the fascia. When the device is removed, the two ends of the suture may be pulled and tied to close the incision.

FIGS. 6A-6B are a prior art device described in US Patent Application No. 2013/0165956 to Sherts et al. The '956 application describes a suture passer guide that includes an elongate member having a longitudinal axis and defining a first proximal opening and a first distal opening. The first proximal and distal openings are substantially aligned with one another such that a suture passer can be extended through the first proximal and distal openings at an acute angle relative to the longitudinal axis of the elongate member. The suture passer guide can be configured to be passed through a central lumen of an endoscopic port.

TAP Block

It is desirable in endoscopic and robotic surgery to perform a TAP block (transverse abdominal plane) and/or to inject an anti-inflammatory agent in proximity to a trocar port in order to provide short term or prolonged postoperative pain relief for a patient.

FIG. 56 is a prior art illustration of a TAP block. In this method, an ultrasound probe is used to determine when a needle tip is in a desired position between internal oblique muscle (IO) and the transversus abdominis (TA) so that a local anasthetic (I) may be injected. This intramuscular region between the internal oblique muscle (IO) and the transversus abdominis (TA) is also the desired injection site for steroids or NSAIDs (non-steroidal anti-inflammatory drugs).

FIG. 57A is a prior art illustration, from above downwards, of skin; subcutaneous tissue; fat; and the external oblique (EO), internal oblique muscle (IO), the transversus abdominis (TA) muscles. The peritoneum and bowel loops may also be visualized deeper to the muscles.

FIG. 57B is a prior art illustration showing the desired positioning of a TAP block between the internal oblique muscle (IO), and the transversus abdominis (TA) muscles. Upon reaching the desired plane with ultrasound guidance, 2 ml of saline is injected to confirm correct needle position, after which 20 ml of local anesthetic solution is injected. The TAP plane is shown expanding with the injection, as indicated by the ultrasound.

In the present invention, an endoscopic trocar port closure device may be configured to inject or otherwise deliver one or more substances at a desired intra-muscular layer.

SUMMARY OF INVENTION

A suture placement device is used to used to position a suture for intra-abdominal suturing and suturing of puncture wounds generated by surgical laparoscopic trocar ports and other puncturing devices.

FIG. 54A is a cross section schematic of a trocar port 85 positioned in a trocar insertion site 80 though fat layer 96 and fascia 90. When the trocar port is removed, it is desirable to close the insertion site by tying a suture with a knot which is tied above the fascia, and to have the suture pass through the abdominal wall about 1 cm from the edge of the insertion site or outside diameter of the trocar port.

FIG. 54B is a cross section schematic of the trocar insertion site 80 when the trocar port is removed. A desired suture path A-B-C-C'-B'-A' 900 includes suture path segments A-B 910, B-C 920, C-C' 930, C'-B' 940, and B'-A' 950 so that suture can be grasped at points A and A' in order to tie a knot.

FIG. 54S shows a suture 590 which has been routed through the desired suture path, and the the suture placement device is withdrawn. FIG. 54T shows the suture 590 tied with a knot 591 so that the trocar insertion site is re-approximated.

In order to create these path segments, it is necessary to remove the trocar port; to raise the bottom of the trocar port above B and B'; or to provide slots or other access through the trocar port wall. In the examples below, the trocar port is removed after inserting a suture placement device, and the suture placement device is used to create a suture path so that a suture can be loaded into the path without loss of pneumoperitoneum. In other examples, the trocar may be partially raised, or slots may be provided in the trocar.

Prior art approaches typically use needles or suture passers to deliver a suture to points C and C', or to capture a pre-loaded suture from the proximity of points C and C'. In the embodiments described below, there are no exposed sharps, as the suture path is created and the suture is loaded through the suture path.

In the embodiments described below, suture path segment C-C' is created by provided by an extension mechanism, such as a pivot bar or a pair of wings.

In the embodiments described below, suture path segments B-C and B'-C' are created by stylet guides which are deployed to penetrate the fascia and to provide stylet guide suture path segments between B-C and B'-C'.

In the example of FIGS. 54A-54T, the extension mechanism is a pivot bar and the stylet guides are flexible guides which are deployed from within the housing of the suture placement device. Other structural elements and methods may be used to create the suture path segments, and several examples are described in this summary and in the detailed description.

In this example, a suture placement device 100 comprises an elongated body with its features in profile to allow use through a trocar port device 85 which can be removed over the suture placement device. The suture placement device comprises an elongated cannula having proximal and distal ends.

An extension mechanism, in this example a pivot bar, may be rotated from a first position aligned with the elongated cannula as shown in FIG. 54C, to a second extended position perpendicular to the elongated cannula.

In the extended position as shown in FIGS. 54D-I, the upper surface of the pivot bar has a first receptor port 554 which is located a desired distance from the outside of the housing, typically 1 cm, and a diametrically opposed second receptor port 554 which is located a desired distance from the outside of the housing on the opposite side of the housing. A pivot bar suture path segment 551 is provided through the pivot bar between the first receptor port and the second receptor port.

The extended pivot bar permits the suture placement device to be held in place while the trocar port is removed, and protects the abdominal cavity from exposure to sharps.

A pair of hollow bore stylet guides 960 and 970 is provided in the housing. In a first, retracted position, the stylet guides are positioned in the housing. FIG. 54F illustrates a first stylet guide 960 in a retracted position. In a second deployed position, the stylet guides are pushed downwardly through the fascia and muscle until the lower ends of the stylet guides are pushed into the receptor ports.

FIG. 54G shows the stylet guides partially deployed through the fascia. A partially deployed position may be used to inject anesthetic or anti-inflammatory agents to a precise intra-muscular layer. In one example, the partially deployed position is established by a first mechanical stop on a plunger. In this example, the plunger and stop comprise the first injection tube depth positioning element. An analgesic, anti-inflammatory agent, or other substance may be injected through one or both partially deployed stylet guides. The stylet guides can then be fully deployed to complete the suture path and route a suture as described below.

When deployed as shown in FIG. 54H, the stylet guides provide stylet guide suture path segments. In this example, the stylet guides provide suture path segments from the receptor ports through the suture placement device, so that the combination of the stylet guide suture path segments and the pivot bar suture path segment provide a complete suture path 900.

FIG. 54J illustrates a stylet 580 used to place a suture 590 in the suture path. In this example, one end of the suture is affixed to the distal end of a stylet; and the proximal end of the stylet is fed through a first stylet guide, down through the first receptor port, through the pivot bar suture path, up through the second stylet port, up through the second stylet guide and out of the housing. The first end of the stylet is then pulled out of the housing until the suture emerges from the housing, and the suture is removed from the second end of the stylet.

In FIG. 54J, the second stylet guide is routed through the proximal end of the device. In FIG. 54L, the second stylet guide is routed through the side of the device so that path C-C'-B'-A' is shorter than path A-B-C. This difference in length facilitates the use of a suture loading tool that has a leading flexible portion which is inserted into path A-B-C; and a plunger section which quickly drives the flexible portion through path C-C'-B'-A' as plunger is pushed through the path A-B-C.

A suture may be carried with the leading edge of a stylet or suture loading tool, or the suture may be attached to the proximal end of the stylet and pulled backward through the suture path as illustrated by FIGS. 54M and 54N. The first end of the stylet is fed through the stylet guides and pivot bar suture path as described above; and the end of the suture is attached to the proximal end of the stylet when the proximal end emerges from the housing. The stylet is then pulled backward until the suture emerges from the proximal end of the first stylet guide, and the suture is removed from the first end of the stylet.

After the suture is routed, the stylet guides are retracted back into the housing, leaving portions of the suture in place in the fascia between the housing and the first receptor port, and between the housing and the second receptor port as illustrated in FIG. 54O.

The pivot bar is rotated back to a vertical position as illustrated in FIG. 54P. A suture release slot is provided along the pivot bar suture path so that the suture is released from the pivot bar slot as the pivot bar is rotated back to alignment with the vertical axis of the cannula.

As the suture placement device is removed, the suture complex is thus deployed across the tissue defect site from within the abdominal cavity to secure the free ends of the suture outwardly from the inside of the peritoneal cavity via the laparoscopic port site. In one example, the device is configured to be utilized through a 10 mm or larger laparoscopic port, and is operative to position the suture at the tissue defect site such that the suture extends in a diametrically-opposed configuration at least 1 cm or greater across opposed edges of the tissue defect site which is caused by the laparoscopic trocar port device.

When the suture placement device is withdrawn from the laparoscopic trocar port site or other tissue defect site, the suture is securely attached to the innermost peritoneal cavity tissue layer, fascia, and muscle—incorporating at least 1 cm of the adjacent area surrounding the tissue defect site. Once the surgical suture(s) has been placed, a knot can be placed above the fascia to seal the tissue opening by reapproximating the edges of the defect created by the laparoscopic trocar device.

In the example above, the suture path segment C-C' is provided as a single path through an elongated pivotal element.

The suture path segment C-C' may be established with a dual path technique as illustrated in FIGS. 55A and 55B. The path C-D-E-E'-D'-C' collapses to C-C' as the suture is pulled or as the suture placement device is removed and the suture at points E and E' drops to the bottom of the trocar insertion site. Segments D-E and E'-D' are typically either open or provided with a suture release slot to permit the suture to fall out as the suture placement device is removed as illustrated in FIG. 55B.

One way to create the suture path is to insert the first end of a stylet through points A-B-C-D-E, and then to direct the first end of the stylet through points E'-D'-C'-B'-A' so that the two ends of the suture can be grasped at points A and A'. The re-direction of the stylet between points E and E' may be accomplished by grasping the stylet as it exits the suture placement device at point E, and then reinserting the stylet into the suture placement device at point E'.

Another way to create the suture path is to direct the first end of the suture through points E-D-C-B-A, and to direct the other end of the suture through points E'-D'-C'-B'-A' so that the two ends of the suture can be grasped at points A and A'.

In the examples described below, a "stylet" is inserted into the suture path and used to pull an end of a suture through suture path segments.

In this specification, the term "stylet" means any mechanical element or assembly that is flexible and strong enough to be pushed or pulled through the suture path segments. In various examples, the "stylet" can be a classic configuration of a thin wire core within an outer wire loop; a leading section wire loop, with or without a thin wire cord, and a trailing plunger section with greater rigidity; and an assembly of a flexible leading portion, a more rigid plunger section, and a handle. The stylet may include features for grasping a portion of the suture.

General Method of Suture Placement

FIG. 7 is a flow chart which summarizes a general method of using a suture placement device to create suture paths and channels, and to use stylets to pull suture through the paths or channels.

At step 1000, a suture placement device is provided in a cannular housing. In one embodiment, the suture placement device comprises a pair of deployable stylet guides which assist in creating suture paths or channels within the body tissue. A pivot bar or other extension mechanism is provided on the distal end of the suture placement device to prevent the deployable elements from piercing intestines or internal organs, and to establish a suture path below the fascia.

At step 2000, a suture path is created.

In one embodiment, a single suture path is illustrated by FIGS. 54D and 54E:

through the upper portion of the cannular housing down the first stylet guide, through the fascia to the first receptor port on the pivot bar, through the first receptor port, across the pivot bar, to the second receptor port on the pivot bar, and up through the second stylet guide through the fascia, and through the cannular housing.

In other embodiments, a dual suture path is illustrated by FIGS. 54F and 54G.

The suture is not required to be preloaded into the cannular housing, and any desired suture can be used.

In the examples described below, the portions of suture path that is through fascia is created by penetrating the fascia in a downward direction with a flexible or rigid guide; or by penetrating the fascia in an upward direction by a curved guide, a telescoping curved guide, or a long flexible conduit.

At step 3000, a stylet is inserted into the suture path, and the stylet is used to pull a suture through the suture path segments.

At step 4000, the stylet is removed from the suture path. The suture falls free of the cannular housing as the suture placement device is removed, and the suture ends are tied to form a knot in or above the fascia in order to close a lower portion of the tissue opening.

At step 5000, the suture placement device is removed. In one embodiment, stylet guides are retracted back into the cannular housing and a pivot bar element is rotated back to a retracted position before the suture placement device is removed.

At step 6000, the suture ends are tied.

Method of Modifying Port Site Closure Device to Provide TAP Block

Prior art methods, such as the ultrasound-guided approach described above, attempt to locate the desired injection site by measuring from above the site. Variations between patients' fat layer thickness make it difficult to know the exact depth of the desired injection site.

While fat layer thickness varies substantially between patients, the distance between the abdominal wall and the desired injection site is much more constant. A fascial plane reference element such as wings, a pivot bar, needle guides, or other deployable element can locate the abdominal wall so that an injection depth positioning device can properly position one or more injection tubes for delivering a substance to a desired inter-muscular layer.

In one embodiment, the injection depth positioning device comprises a fascial plane reference element such as such as a pivot bar or wings; a first injection tube (stylet guide) having a distal end; and an first injection tube depth positioning element. These elements can be provided in suture placement devices.

Examples of injection tube depth positioning elements include fixed mechanical stops, adjustable mechanical stops; and visual indicators such as color bands and scales.

In some examples, a suture placement device facilitates the placement or injection of a substance or substances in proximity to a trocar port at a controlled depth.

FIG. 55 is a flow chart which summarizes a general method of modifying a port site closure device to inject a substance at a desired depth within the fascia muscle layers.

At step 1050, a modified port closure device is provided. In one embodiment, the modified port closure device comprises a housing; a fascial plane reference element; a first injection tube having a distal end; a first injection tube depth positioning element; and a pair of deployable stylet guides which assist in creating suture paths or channels within the body tissue.

At step 1100, the modified port closure device is inserted into a trocar port or into a trocar port site after a trocar port has been removed.

At step 1200, the trocar is removed if it has not been previously removed

At step 1300, the location of the facial plane is established with the fascial plane reference element of the modified port closure device. In various examples, the fascial plane reference element is a pivotal bar, one or more wings, fixed hooks, needle guides, or other element.

At step 1400, the injection tube depth positioning element is used to position the injection tube distal end at a first tissue depth relative to the location of the fascial plane. In various examples, the injection tube depth positioning element is a fixed mechanical stop; an adjustable mechanical stop; color coded depth bands; an alphanumeric scale; an encoder and signal; or other element.

At step 1500, the substance is injected or otherwise introduced through the injection tube. In various examples, the injection tube is a flexible stylet guide, a fixed stylet guide, a fixed straight needle, a flexible needle, a curved needle, a telescoping guide or needle, or other element. The injection tube may serve a dual purpose as a suture passer or stylet guide.

In various examples, a single injection tube may be used to make a single injection or multiple injections, or multiple injection tubes may be used.

At step 1600, injection tube may be positioned at a second tissue depth, such as to place a suture or to position a stylet guide.

Suture Placement Devices

Example suture placement devices are described below.

180 Degree Stylet Guides (FIGS. 8-13)

In one embodiment, a first suture path and second suture path are created by a pair of 180 degree specialized stylet guides which are deployed from within a cannular housing. These specialized guides are designed to penetrate tissue by having a sharp bevel-shaped tip and are designed to create a channel or tunnel path for a stylet by having a hollow-bore tunnel built within the guide. A slot on the lateral aspect of each guide allows the suture to be removed from the device after placement. In one example, a metal guide is configured as a C-shaped curved tunnel on cross sectional imaging. After deploying an extension mechanism, a pair of wings, the guides are rotated through the wings to penetrate the fascia from a distance of about 1 cm from the outside of the cannular housing and extend back to openings in the side of the cannular housing. A stylet is then directed down the cannular housing through the first 180 degree stylet guide, back through an opening in the side of the cannular housing, and up through the cannular housing. In this example, one or both of the pair of wings serves as a fascial plane reference element and one or both stylet guides serves as an injection tube. The desired depth of the distal end of the stylet guide(s) may be set with a fixed mechanical stop or an adjustable mechanical stop, or manually with the help of a user guide such as one or more color coded bands or a ruling. A single mechanical plunger may be used to set the depth of both stylet guides. An adapter may be provided to simultaneously introduce a substance or mixture to both stylet guides.

140 Degree Stylet Guides (FIGS. 33-42)

In another embodiment, a first suture path and second suture path are created by a pair of 140 degree specialized stylet guides which are deployed from within a cannular housing. These specialized guides are designed to penetrate tissue by having a sharp bevel-shaped tip and are designed to create a channel or tunnel path for a stylet by having a hollow-bore tunnel built within the guide. The guide has an opening on the lateral aspect of the guide to allow the suture to be removed from the device after placement. In one example, a metal guide is configured as a C-shaped curved tunnel on cross-sectional imaging. As an extension mechanism is deployed, the guides are rotated to penetrate the fascia from a distance of about 1 cm from the outside of the cannular housing and extend back to openings in the side of the cannular housing. In one example, gaps in the suture path are bridged by a flexible conduit in order to provide a continuous stylet path prior to the insertion of a stylet. In another example, the gaps may be bridged directly by pushing a stylet through the guide segments and through tissue in the gaps Telescoping Curved Guides (Accordian Guides)

In another embodiment, the first path and second path for the stylet(s) are created by sets of two or more telescoping curved stylet guides. After deploying an extension mechanism, each set of telescoping guides penetrate the fascia from a distance of about 1 cm from the outside of the cannular device and extend back to openings in the side of the cannular housing. A stylet is then directed down the cannular housing through the telescoping guides, back through the opening in the side of the cannular housing, and up through the cannular housing.

Fixed Hook Stylet Guides (FIGS. 14-32)

In this example, the suture placement device comprises a cannular housing with an extension mechanism, which is pair of fixed hook guides with an initial closed orientation. The fixed hooks may be extended outwardly from the cannular housing by squeezing the handles together after the device is inserted into a trocar port. The extended hook guides provide suture paths through the cannular housing to tissue insertion points. Flexible conduits are used as stylet guides to complete a suture path from a first tissue insertion point to a first side opening in the cannular housing, and from a second tissue insertion point to a second side opening in the cannular housing. In this example, the hook guides serves as a fascial plane reference element and one or both stylet guides serves as an injection tube. The desired depth of the distal end of the stylet guides may be set with a fixed mechanical stop or an adjustable mechanical stop, or manually with the help of a user guide such as one or more color coded bands or a ruling. A single mechanical plunger may be used to set the depth of both stylet guides.

Flexible Stylet Guides Deployed from Housing (FIGS. 43-53 and 61-73)

In another embodiment, a single suture path is created by a pair of stylet guides which are deployed downwardly and outwardly from two sides of a cannular housing. These guides are designed to penetrate tissue by having a sharp bevel-shaped tip and are designed to create a suture path segment for a stylet by having a hollow-bore tunnel built within the guide.

An extension mechanism, a pivot bar, is deployed from the housing, and positioned below the fascia. A channel is provided in the pivot bar, and extends from a receptor port on each side of the pivot bar, such that the receptor ports are located about 1 cm from opposed sides of the outside of the cannular housing. When the stylet guides are fully deployed, the distal end of each stylet guide engages a receptor port, thereby creating a suture path through the first stylet guide, into the first receptor port, through the channel, through the second receptor port, and through the second stylet guide. A stylet is then directed through the suture path to pull the first end of a suture through the path. After routing the suture, the stylet guides are refracted, leaving the suture routed through the fascia. The pivot bar has a suture release slot, and the suture is released through the suture release slot as the pivot bar is rotated back to a folded position. The suture placement device is withdrawn and the suture is tied.

One or both stylet guide may have a partially deployed position so that the distal end of the guide is precisely positioned relative to the fascia. An anesthetic or anti-inflammatory agent is injected through one or both guides to improve post-surgery comfort of a patient.

In one example, the stylet guides have openings at the proximal end of the housing. In another example, a first stylet guide has an entry opening at the proximal end of the housing, and a second stylet guide has an exit opening below the proximal end of the housing so that the exit path is shorter than the inlet path.

In one example, the device is a disposable plastic device. In another example, the device is a reusable metal or plastic device. In other examples, the device comprises a re-usable metal housing and a disposable guide assembly which may include a replaceable pivot bar.

In this example, the pivot bar serves as a fascial plane reference element and one or both stylet guides serves as an injection tube. The desired depth of the distal end of the stylet guide(s) may be set with a fixed mechanical stop or an adjustable mechanical stop, or manually with the help of a user guide such as one or more color coded bands or a ruling. A single mechanical plunger may be used to set the depth of both stylet guides.

In one example, the stylet guides have openings at the proximal end of the housing. In another example, a first stylet guide has an entry opening at the proximal end of the housing, and a second stylet guide has an exit opening below the proximal end of the housing so that the exit path is shorter than the inlet path. A luer fitting or o-ring may be provided on the entry opening so that a syringe may be used to inject a substance through the first stylet guide.

Rigid Stylet Guides Aligned by Housing

In this example, an extension mechanism, such as a pivot bar or pair of wings, is deployed as described above to position receptor ports below the fascia. A suture path segment is provided between the receptor ports.

A pair of rigid stylet guides are deployed at a downward angle through alignment slots provided in the housing. The guides penetrate tissue and create a suture path segment for a stylet. After routing the suture, the stylet guides are retracted, leaving the suture routed through the fascia. The suture is released from the housing alignment slot by suture release slots provided on the housing, and released from the extension mechanism as the pivot bar or wings are rotated back to a folded position and the suture placement device is withdrawn.

One or both stylet guide may have a partially deployed position so that the distal end of the guide is precisely positioned relative to the fascia. An anesthetic is injected through the guide(s) to improve post-surgery comfort of a patient.

In these examples, the pivot bar or wings serve as a fascial plane reference element and one or both stylet guides serves as an injection tube. The desired depth of the distal end of the stylet guide(s) may be set with a fixed mechanical stop or an adjustable mechanical stop, or manually with the help of a user guide such as one or more color coded bands or a ruling.

DESCRIPTION OF FIGURES

These and other features, aspects, and advantages of the present invention will become better understood with regard to the following description, appended claims, and accompanying drawings where:

FIGS. 4A and 4B are a prior art device shown in U.S. Pat. No. 8,109,943 to Boraiah et al.

FIGS. 6A and 6B are a prior art device shown in in US Patent Application No. 2013/0165956 to Sherts et al.

FIG. 8 is a front view of the lower portion of a suture placement device inserted into a tissue opening with the wings closed.

FIG. 9 is a front view of the lower portion of the suture placement device of FIG. 8 with the wings deployed to an extended orientation laterally.

FIG. 10 is a front view of the lower portion of the suture placement device of FIG. 8 with the wings deployed to an extended orientation and curved guides rotated 90 degrees.

FIG. 11A is a front view of the lower portion of the suture placement device of FIG. 8 with the wings deployed to an extended orientation and curved guides rotated 90 degrees, penetrating through tissue, and connecting to the opening on the side of the cannular housing device.

FIG. 11B is a front view of the lower portion of the suture placement device of FIG. 8 showing a first stylet guide entry tube and exit tube.

FIG. 11C is a front view of the lower portion of the suture placement device of FIG. 8 showing guide extensions.

FIG. 12 is a front-oblique perspective view of the lower portion of the suture placement device of FIG. 8 with the wings oriented in an initial folded position and curved guides in an initial downward, longitudinal orientation.

FIG. 13 is a side view of the lower portion of the suture placement device of FIG. 8 with the wings oriented in an initial folded position and curved guides in an initial downward, longitudinal orientation.

FIG. 33 is a front cross section view of another embodiment of a suture placement device positioned for insertion into a tissue defect within the abdominal wall.

FIG. 34 is a front cross section view of the suture placement device of FIG. 33 inserted into a defect within the tissue with a first rotatable guide in the initial orientation.

FIG. 42B is a front cross section view of the suture placement device of FIG. 33 showing the first guide segment in the fully deployed orientation and a bridge segment.

FIG. 44A is a side perspective view showing a stylet partially inserted into the first guide of the embodiment of the suture placement device of FIG. 43A.

FIG. 44B is a side perspective view showing a stylet inserted into the first guide and pivot bar channel of the embodiment of the suture placement device of FIG. 43A.

FIG. 44C is a side perspective view showing a stylet inserted into the first guide, pivot bar channel, and second guide of the embodiment of the suture placement device of FIG. 43A.

FIG. 44D is a side perspective view showing a stylet pulling the end of a suture into the first guide of the suture placement device of FIG. 43A.

FIG. 44E is a side perspective view showing a stylet pulling the end of a suture through the first guide and channel of the suture placement device of FIG. 43A.

FIG. 44F is a side perspective view showing a stylet pulling the end of a suture through the first guide, channel, and second guide of the suture placement device of FIG. 43A.

FIG. 44G is a side perspective view showing a suture positioned through the first guide, channel, and second guide of the suture placement device of FIG. 43A, and the pivot bar wing in a retracted position.

FIG. 44H is a side perspective view showing the suture of FIG. 43G as the suture placement device is partially removed.

FIG. 45 is a side perspective view showing a first half of a pivot bar wing for the suture placement device of FIG. 43A.

FIG. 46A is a top perspective view of a plunger for the suture placement device of FIG. 43A.

FIG. 46B is a bottom perspective view of the plunger of FIG. 46A.

FIG. 49A is a side perspective view of the outside of a first body section for the suture placement device of FIG. 43A.

FIG. 49B is a side perspective view of the inside of a second body section for the suture placement device of FIG. 43A.

FIG. 49C is a side view of the inside of the first body section of FIG. 49B.

FIG. 49D is a bottom perspective view of the inside of the second body section of FIG. 49A.

FIG. 50A is a side perspective view of a first actuation arm for the suture placement device of FIG. 43A.

FIG. 50B is a side perspective view of a second actuation arm for the suture placement device of FIG. 43A.

FIG. 51 is a side perspective view of the suture placement device of FIG. 43A with the pivot bar wing in a retracted position.

FIG. 52 is a side perspective view of the suture placement device of FIG. 43A with the pivot bar wing in a retracted position.

FIG. 53 is a top perspective view of the suture placement device of FIG. 43A with the pivot bar wing in a retracted position.

FIG. 54G is a cross section schematic of the suture placement device of FIG. 54E showing a distal suture path through the pivot bar, and stylet guides partially deployed.

FIG. 54H is a cross section schematic of the suture placement device of FIG. 54E showing stylet guides fully deployed.

FIG. 54I is a cross section schematic of the suture placement device of FIG. 54H showing stylet path segments.

FIG. 54M is a cross section schematic of the suture placement device of FIG. 54L showing a suture attached to the stylet.

FIG. 54N is a cross section schematic of the suture placement device of FIG. 54M showing the suture pulled through the suture path.

FIG. 60A shows shows a guide plunger partially depressed according to a first color band or scale reading on the housing.

FIG. 60B shows the guide plunger partially depressed according to a second color band or scale reading on the housing.

FIG. 60C shows the guide plunger fully depressed so that the stylet guide tips are fully deployed.

FIG. 64 is an exploded side perspective view of the suture placement device of FIG. 61.

FIG. 65 is a front view of the upper body portion of the plastic suture placement device of FIG. 61.

FIG. 66 is a side perspective view of the upper body portion of the plastic suture placement device of FIG. 61.

FIG. 72 is a front perspective view of a pivot bar section of the suture placement device of FIG. 61.

FIG. 73 is a front perspective view of an assembled pivot bar of the suture placement device of FIG. 61.

FIG. 74A shows a suture placement device that is configured to be used as an obturator.

FIG. 74B shows the suture placement device/obturator of FIG. 74A with the head removed so that the device is configured to be used as a suture placement device.

FIG. 74C shows the pivot bar 720 deployed when the device of FIG. 74B is inserted into a trocar port.

FIG. 75A is a cross section view of a stylet inserted into a 8 mm trocar port.

FIG. 75B is a cross section view of the stylet of FIG. 75A inserted into a stylet guide of a suture placement device.

FIG. 75C is a cross section view of the stylet of FIG. 75A withdrawn into the stylet guide of the suture placement device of FIG. 75B.

FIG. 76A is a cross section illustration of a portion of a suture loading device partially inserted into a suture placement device.

FIG. 76B is a cross section illustration of the suture loading device of FIG. 76A fully inserted into a suture placement device with a suture attached to the distal end of the suture loading device.

FIG. 76C is a cross section illustration of the suture loading device of FIG. 76A partially withdrawn from the suture placement device.

FIG. 76D is a cross section illustration of the suture loading device of FIG. 76A almost fully withdrawn from the suture placement device.

FIG. 76E is a cross section illustration of the suture loading device of FIG. 76A fully withdrawn from the suture placement device and detached from the suture.

FIG. 77A is a front perspective view of a suture loading device.

FIG. 77B is a detailed cross section view of a handle assembly of the suture loading device of FIG. 77A.

FIG. 77C is a detailed view of the distal end of the suture loading device of FIG. 77A in its normally-closed orientation.

Figure 77A:
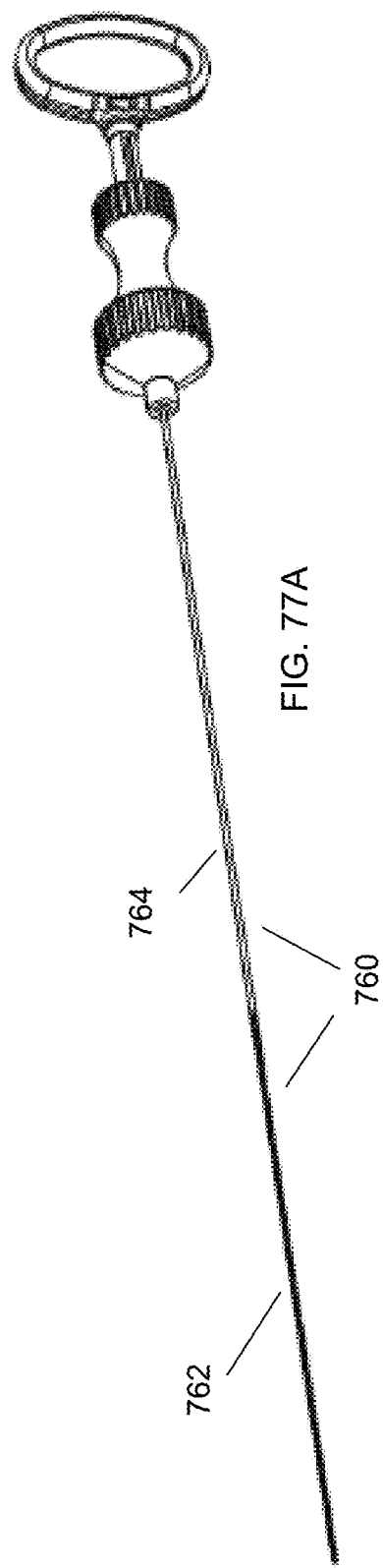

FIG. 77D is a detailed cross section view of a handle assembly of the suture loading device of FIG. 77A in a suture capture/release orientation.

FIG. 77E is a detailed view of the distal end of suture loading device of the suture loading device of FIG. 77A with the device in a suture-capture orientation.

FIG. 78A is a front perspective view of another suture loading device.

FIG. 78B is a detailed cross section view of a handle assembly of the suture loading device of FIG. 78A.

FIG. 78C is a detailed view of the distal end portion of the suture loading device of FIG. 78A.

Figure 79:
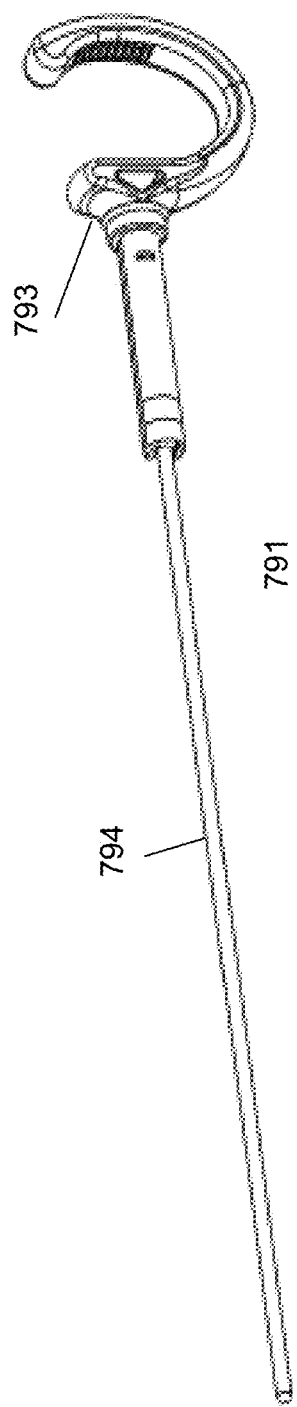

FIG. 79 is a front perspective view of a plunger suture loading device.

DESCRIPTION OF EMBODIMENT

Suture Placement Device with Curved Rotatable Guides and Wings

FIG. 8 is a front view of the lower portion of the cannular housing 110 of a suture placement device 102 inserted into a tissue opening 82 through the fascia 90 and fat 96 layers.

In this embodiment, the suture placement device 102 includes an extension mechanism, a pair of wings 120 and 130, which unfold to extended positions, and curved guides which rotate along guide recesses and slots in the wings, through the fascia layer, and back to the cannular housing.
Wings The suture placement device 102 is inserted with the pair of wings 120 and 130 oriented in an initial folded position so that the wings are aligned with the longitudinal axis 108 of the cannular device. Each wing has a recessed guide travel area 122, 132 which provide a suture path segment across the wing; a proximal end 124, 134; and a distal end 126, 136. The wings may be unfolded to a deployed to an extended orientation with a wing deployment mechanism. In this example, the deployed wings are perpendicular to the longitudinal axis of the cannular device.

FIG. 9 is a front view of the lower portion of a cannular housing of the suture placement device 102 with the wings 120 and 130 deployed to an extended orientation. In one example, the wing deployment is achieved with a wing deployment mechanism which pushes the wings from a folded to an extended orientation. Once fully deployed, the wings are perpendicular to the longitudinal axis of the cannular device.

Stylet Guides

A pair of curved stylet guides 140 and 150 are initially retracted within the housing and wings as shown in FIG. 8. Each stylet guide is hollow with a suture release slot 141, 151 on the inside arc of the guide. Each stylet guide provides an unobstructed path between a proximal opening 142, 152 and a distal opening 143, 153, with a curved section 144, 154 between the proximal opening and the distal opening. Each stylet guide is mounted on a pivot arm 145, 155 which has a pivot arm proximal end 146, 156 that rotates on a pivot element 147, 157 and a distal end tip 148, 158 connected to the proximal opening of a stylet guide. The guides, their arms, pivot elements, and a guide deployment form guide assemblies. As the guide assemblies are pushed downward by a guide deployment mechanism, the stylet guides begin to rotate outwardly with respect to the cannular housing.

FIG. 10 is a front view of the lower portion of the suture placement device with wings 120 and 130 deployed to a partially extended orientation where each guide is positioned within a wing.

The outside of the lower portion of the device is omitted in the FIGS. 8-11 to show the exposed guide mechanisms. The pair of stylet guides 140 and 150 have been rotated 90 degrees by pushing downward with the guide deployment mechanism (not shown).

In this example, the wings 120 and 130 are located within the abdominal cavity, below the fascia 90 and peritoneal layers of the abdominal wall 91. Stylet guide 140 is rotated in a recess area 128 on wing 120, so that the tip 148 of stylet guide 140 is positioned at a first tissue insertion point 92. As stylet guide 140 is rotated further, the tip 148 of the guide will penetrate fascia 90 tissue in an arced path back toward an opening 111 in the cannular housing 110. The stylet guide 140 thus provides a first suture path below the cannular housing, through tissue, and back to the cannular housing.

Stylet guide 150 is rotated in a recess area 138 on wing 130, so that the tip 158 of stylet guide 150 is positioned at a second tissue insertion point 93. As stylet guide 150 is rotated further, the tip 158 will penetrate tissue 90 in an arced path back toward an opening 112 in the cannular housing. The stylet guide 150 thus provides a second suture path below the cannular housing, through tissue, and back to the cannular housing.

FIG. 11A is a front view of the lower portion of the suture placement device with stylet guides 140 and 150 rotated 180 degrees deployed to a fully extended orientation by continuing to push downward with the guide deployment mechanism (not shown).

Stylet guide 140 has created a portion of the first suture path from the first tissue insertion point 92 through opening 111 in the cannular housing 110.

Stylet guide 150 has created a portion of the second suture path from the second tissue insertion point 93 through opening 112 in the cannular housing 110.

FIG. 12 is a front-oblique perspective view of the lower portion of a cannular housing of the suture placement device with the wings 120 and 130 oriented in an initial folded position and stylet guides 140 and 150 in an initial downward, longitudinal orientation. Recessed guide travel areas 122 and 132 on wings 120 and 130 provide room for the guides to be rotated outwardly from the cannular housing. The recessed guide travel areas also serve to confine a stylet so that the stylet can be routed from the first stylet guide 140 to the second stylet guide 150.

FIG. 13 is a side view of the lower portion of a cannular housing of the suture placement device with the wings 120 and 130 oriented in an initial folded position and stylet guides 140 and 150 in an initial downward, longitudinal orientation. The recessed guide travel areas 122 and 132 on wings 120 and 130 provide both lateral and vertical clearance for the guides to be rotated outwardly from the cannular housing.

Example

Dual Suture Path

After deploying the extension mechanism, the pair of wings, the guide segments are rotated through the wings to penetrate the fascia from a distance of about 1 cm from the outside of the cannular housing and extend back to openings in the side of the cannular housing.

In the example of FIG. 11B, a dual suture path is created. A stylet may be routed:
- down a first stylet entry tube 160;
- into proximal end 142 of guide segment 140;
- through guide segment 140;
- out distal end of guide segment 143 to first stylet exit tube 170;
- down a second stylet entry tube 162 (not shown);
- into proximal end 152 of guide segment 150;
- through guide segment 150; and
- out distal end of guide segment 150 to second stylet exit tube 172 (not shown).

The first and second exit tubes may be omitted so that the stylet travels up the inside of the cannular housing.

The distal ends 143 and 153 may be capped and an exit slot provided on the upper portions of the distal ends to direct a stylet upward into exit tubes or upward through the cannular housing.

Example

Single Suture Path

In the example of FIG. 11C, a single suture path is created. A stylet may be routed:
- down a first stylet entry tube 174
- into proximal end 142 of guide segment 140;
- through guide segment 140;
- out distal end of guide segment 140;
- through first wing channel 122 and guide extension 180;
- through guide extension 182 and second wing channel 132;
- into proximal end 153 of guide segment 150;
- through guide segment 150;
- out distal end of guide segment 150 to second stylet exit tube 175

In this example, a stylet may be routed directly from the first wing channel 122 to the first wing channel 132. The second exit tube may be omitted so that the stylet travels up the inside of the cannular housing.

TAP or Other Substance Introduction

In this example, one wing or the pair of wings serves as a fascial plane reference element and one or both stylet guides serves as an injection tube. A single mechanical plunger may be used to set a partially deployed depth of both stylet guides. The desired depth of the distal end of the stylet guide(s) may be set with a fixed mechanical stop or an adjustable mechanical stop on the plunger, or manually with the help of a user guide such as one or more color coded bands or ruling on the suture placement housing that correspond to distance or a range of distance of the stylet guide tip(s) above the the pair of wings. In some cases, a single stylet guide can provide a single injection, and the injected substance will spread or migrate completely around a trocar port site. In other cases, a two stylet guides can be used to inject a substance on opposite sides of a trocar port site. An adapter may be provided to simultaneously introduce a substance or mixture to both stylet guides.

DESCRIPTION OF EMBODIMENT

Suture Placement Device with "140 Degree" Rotatable Guides

FIGS. 33-41 show another embodiment of a suture placement device. For clarity, the figures show only a first curved stylet guide segment 430 of a pair of curved stylet guide segments. The guide segment 430 is mounted on pivot arm 450, and the combination of the guide segment and pivot arm serve as an extension mechanism that positions the tip 434 of the guide segment 430 at a first tissue insertion point 92 as the pivot arm is rotated. When rotated into the extended position, the guide segment 430 provides a partial path for a stylet or flexible conduit.

Figure 37:
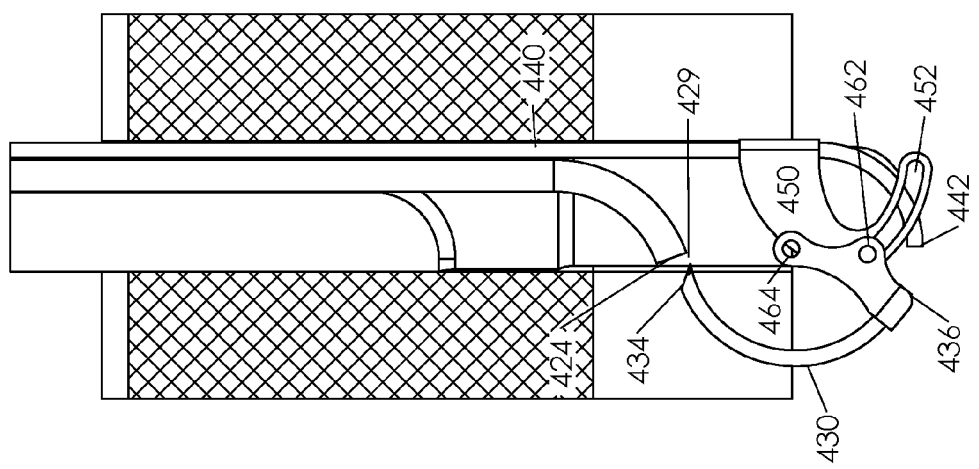
FIG. 37 is a front cross section view of the suture placement device of FIG. 33 showing the first guide segment in the fully deployed orientation.

Referring to FIG. 37, there may be a gap between the tip 434 of guide segment 430 and the open distal end 424 of the first stylet exit guide 420. There may also be a gap between the proximal end 436 of the guide segment 430 and the open distal end 442 of first stylet entry guide 440. As discussed below, these gaps may be bridged by a flexible conduit in order to provide a continuous stylet path prior to the insertion of a stylet; or the gaps may be bridged directly by pushing a stylet through the guide segments and through tissue in the gap(s). The curved guide segments thus serve directly or indirectly as stylet guides.

In this example, curved guides with an arc greater than 90 degrees and less than 180 degrees are provided. The guides are rotated into into position by rotating the extension mechanism and penetrating portions of the fascia from points about 1 cm apart from opposing sides of the the housing of the suture placement device so that a stylet and suture can be placed through the guides.

Figure 40:
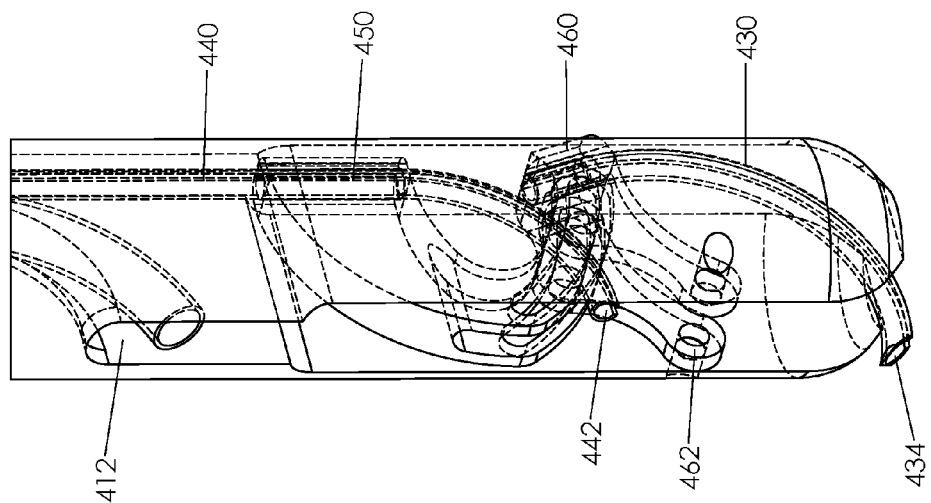
FIG. 40 is a first side perspective detailed view of the suture placement device of FIG. 33 showing the first guide segment in an initial (resting) orientation.
Figure 41:
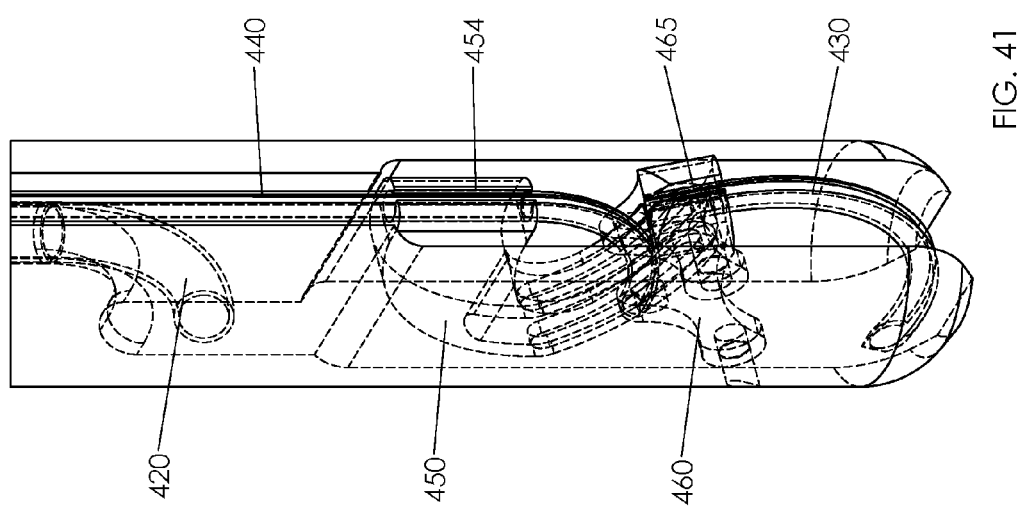
FIG. 41 is a second side perspective detailed view of the suture placement device of FIG. 33 showing the first guide segment in an initial (resting) orientation.

FIG. 33 is a front cross section view of the lower portion of the cannular housing 410 of a suture placement device 104 which is positioned for insertion into a tissue opening through the fascia and fat layers. FIG. 34 is a front cross section view of the suture placement device inserted into the hole in tissue with the first curved stylet guide segment 430 in an initial orientation. FIG. 40 is a first side perspective detailed view of the guide segment 430 in an initial orientation. FIG. 41 is a second side perspective detailed view of the guide segment 430 in an initial orientation.

In this embodiment, the suture placement device 104 includes a pair of curved stylet guide segments which rotate out of the cannular housing, through the fascia layer, and back toward the cannular housing.

In some examples, the device may include protective wings, such as described above. In the example of FIGS. 33-42, the guide segment 430 has an arc of approximately 140 degrees. The guide segment 430 is initially presented in a downward, longitudinal orientation.

The guide segment 430 is hollow with a suture release slot 433 is provided on the outside arc of the guide. The guide segment provides an unobstructed internal suture path between a proximal opening 435 and a distal opening 434 with a curved section 432 between the proximal opening and the distal opening.

Figure 36:
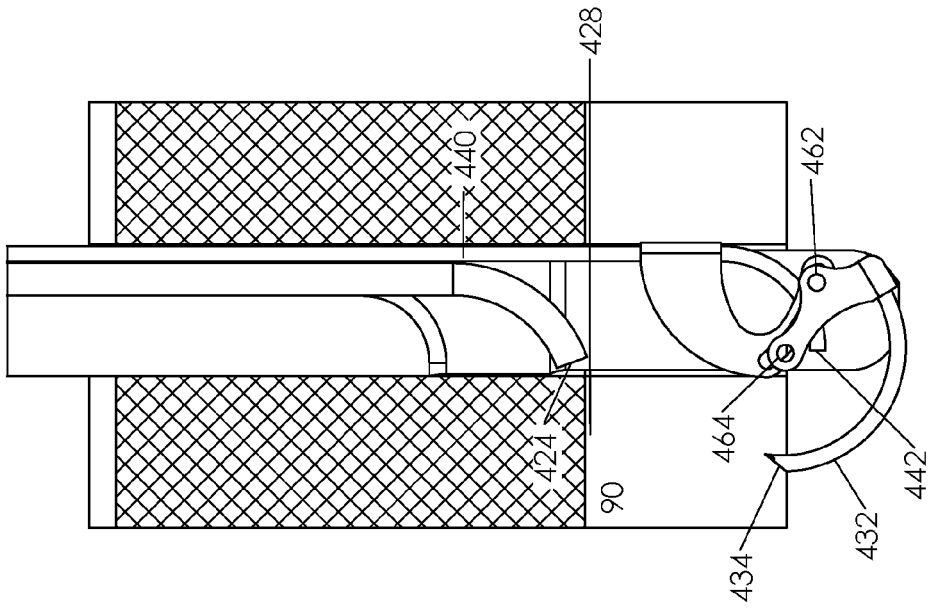
FIG. 36 is a front cross section view of the suture placement device of FIG. 33 showing the first guide segment in a second partially deployed orientation.
Figure 35:
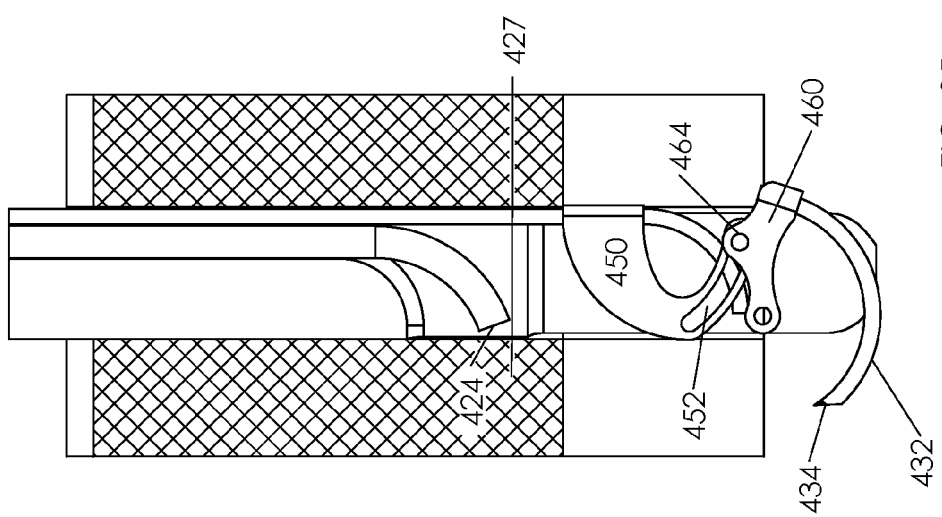
FIG. 35 is a front cross section view of the suture placement device of FIG. 33 inserted into the defect in the tissue showing a first rotatable curved stylet guide segment in a partially deployed orientation.
Figure 38:
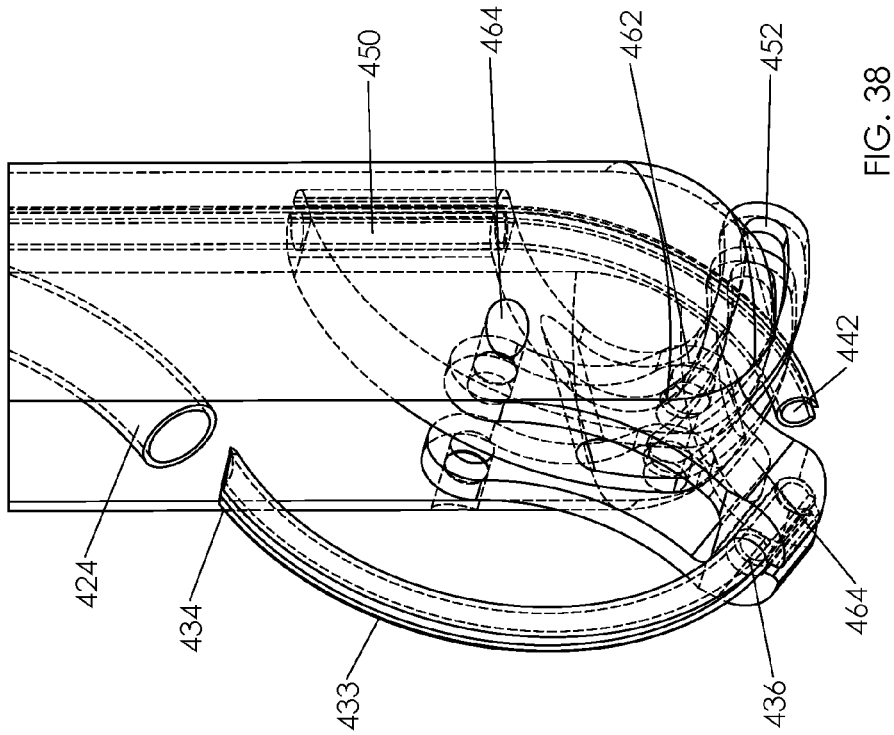
FIG. 38 is a first side perspective detailed view of the suture placement device of FIG. 33 showing the first guide segment in the fully deployed orientation.
Figure 39:
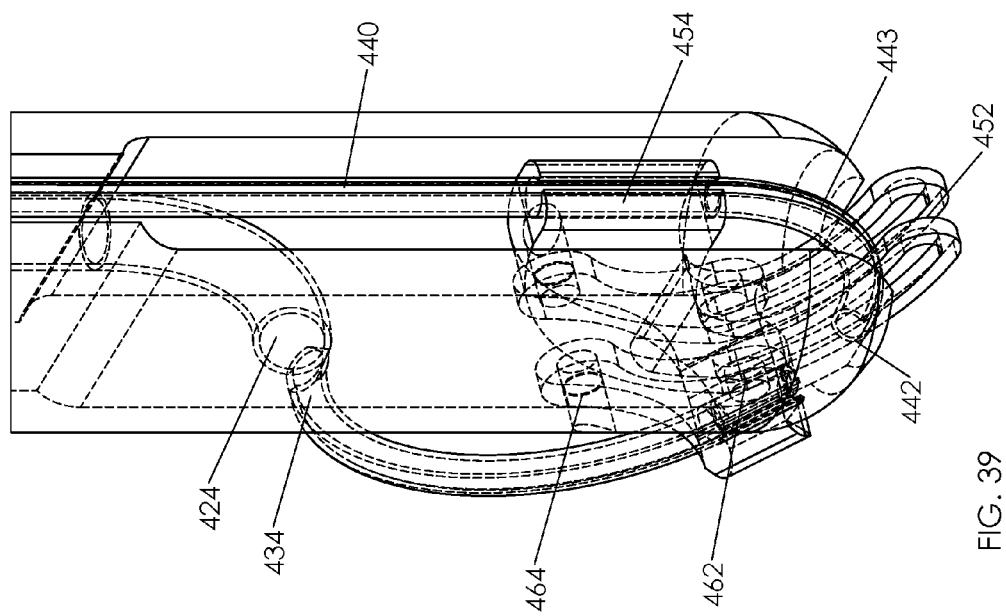
FIG. 39 is a second side perspective detailed view of the suture placement device of FIG. 33 showing the first guide segment in the deployed orientation.

FIGS. 35-37 are front cross section views of the suture placement device 104 as the first guide segment 430 is rotated into a deployed orientation. FIGS. 38-39 are first and second side perspective detailed views of the the first guide segment 430 in a deployed orientation.

Guide segment 430 is rotated that the tip 434 of guide segment 430 is positioned at a first tissue insertion point 92. As the guide segment 430 is rotated further, the tip 434 of the guide segment will penetrate fascia 90 tissue in an arced path back toward an opening 412 in the cannular housing 410. The guide segment 430 thus provides a first suture path below the cannular housing, through tissue from the first tissue insertion point 92 through opening 412 in the cannular housing 410.

As the first stylet entry guide 440 and the first stylet exit guide 420 are lowered, the guide segment 430 is deployed. FIG. 33 shows the initial position of the first stylet entry guide 440 and the first stylet exit guide 420; and FIGS. 34-36 show partially lowered positions 426, 427, and 428 of the first stylet exit guide 420. FIG. 37 shows the fully lowered position 429 of the first stylet exit guide 420.

The guide segment 430 is affixed to a pivot arm 460 which travels in a slot 452 provided on a pivot arm bracket 450. The pivot arm bracket is attached to the first stylet entry guide 440, so that as the first entry guide 440 is lowered with respect to the cannular housing 410, the first entry guide 440 rotates the pivot arm 450. The first entry guide 440, the pivot arm bracket 460, the pivot arm 450, and the first curved guide 430 form a first guide assembly 482. As the first guide assembly is pushed downward by a guide deployment mechanism, the guide segment 430 begins to rotate outwardly with respect to the cannular housing.

As the first stylet entry guide 440 is lowered, it forces guide segment 430 and pivot arm 460 to rotate about pivot pin 462. As the guide segment 430 rotates, the pivot pin 462 and the pivot arm 460 travel upwardly in slot 452, while pin 464 of the pivot arm travels upwardly along the outside of pivot arm bracket 450.

When the guide segment 430 is fully rotated, the tip 434 of the guide segment 430 is located near the side opening 412 in the cannular housing, so that the tip 434 is aligned with opening 424 of the first stylet exit guide 420. This alignment permits a stylet or flexible conduit to complete a first suture path from the curved guide to the first stylet exit guide.

The first stylet entry guide 440 has an outside suture release slot 443; and the guide segment 430 has an outside suture release slot 433. The suture release slots permit a suture to remain in place after the flexible conduit and/or stylet is removed and the suture placement device is withdrawn from the hole.

Example

Bridging Gaps with Flexible Conduit or Stylet

In one example, a flexible conduit is pushed through the curved stylet guide segment and back to an opening in the cannular housing. The flexible conduits serve as stylet guides to provide a path for a suture-carrying stylet which is inserted into the flexible conduit. These flexible conduits are designed with an accordion body to allow it to configure into any shape and angle so that any gaps in the suture path are bridged by the flexible conduits.

In other examples, the leading tip of a stylet is used to bridge narrow gaps in the suture path.

Figure 42A:
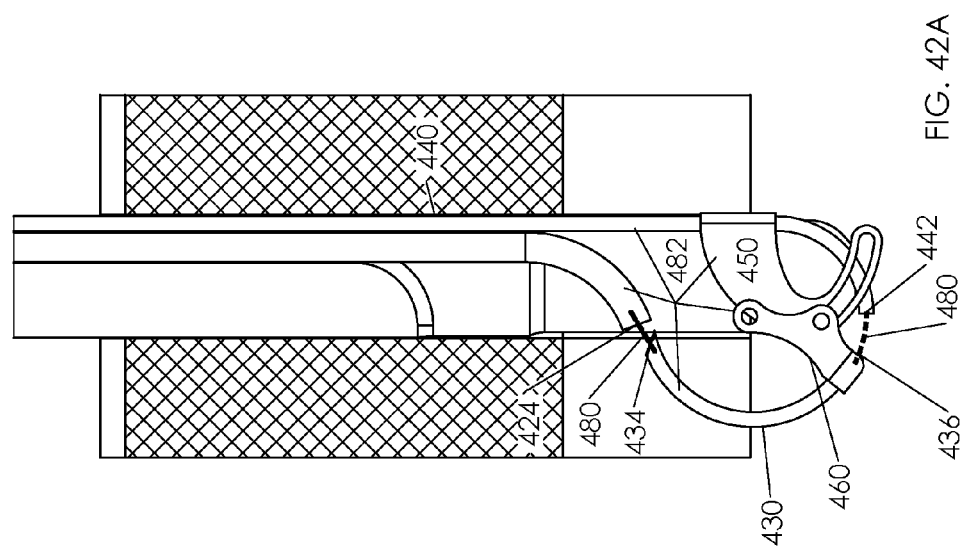
FIG. 42A is a front cross section view of the suture placement device of FIG. 33 showing the first guide segment in the fully deployed orientation and labeling the first suture path.

Referring to FIG. 42A, the flexible conduit may be routed in a dual suture path:
  down the first stylet entry guide 440;
  out open distal end 442 of the first stylet entry guide 440;
  across the gap between the first stylet entry guide and the first curved stylet guide segment;
  into the proximal end 436 of the first guide segment 430;
  through the first guide segment 430;
  out the distal end 434 of the first guide segment 430;
  across the gap between the the first guide segment 430 and the first stylet exit guide;
  into the open distal end 424 of the first stylet exit guide 420;
  up the first stylet exit guide 420; and
  out of the cannular housing;
  down the second stylet entry guide (not shown);
  out open distal end of the second stylet entry guide;
  across the gap between the second stylet entry guide and the second guide segment;
  into the proximal end of the second guide segment;
  through the second guide segment;
  out the distal end of the second guide segment;
  across the gap between the second guide segment and the second stylet exit guide (not shown);
  into the open distal end of the second stylet exit guide 420;
  up the second stylet exit guide; and
  out of the cannular housing;

The flexible conduit routing may be reversed by the flexible conduit down the first stylet exit guide 420 and out the first stylet entry guide 440, then down the second stylet exit guide and out the second stylet entry guide.

Referring to FIG. 42B, the flexible conduit may be routed in a single suture path if a straight bridge segment 470 is provided between first opening 442a in a first direction and a second opening 442b in the opposite direction. In this case, the flexible conduit routing becomes:
  down the first stylet exit guide 420;
  out the open distal end 424 of the first stylet exit guide 420;
  across the gap between the first curved stylet guide segment and the first stylet exit guide;
  into the distal end 434 the first guide segment 430;
  through the first guide segment 430;
  out the proximal end 436 of the first guide segment 430;
  across the gap between the the first guide segment 430 and first opening 442a of bridge segment 470;
  into first opening 442a of bridge segment 470;
  through bridge segment 470 and out second opening 442b;
  across the gap between the second opening 442b of bridge segment 470 and the second guide segment;
  into the proximal end 436 of the second guide segment;
  through the second guide segment;
  out of the distal end the second guide segment;
  across the gap between the second guide segment t and the second stylet exit guide;
  up the second stylet exit guide; and
  out of the cannular housing.

The tangents to the distal end portions of the curved stylet guide segments are aligned with side openings in the cannular housing so that as the tip of the flexible conduit or stylet is pushed out of the distal end, the tip penetrates tissue from the exit port back to the opening in the side of the cannular housing; or from the cannular housing back to the exit port.

DESCRIPTION OF EMBODIMENT

Suture Placement Device with Protective Shield

In this embodiment, a pair curved guides with an arc of between 90 and 180 degrees are deployed such as described above. A protective shield is deployed as the guides are deployed, or before the guides are deployed. The protective shield prevents the deployable elements from piercing intestines or internal organs.

DESCRIPTION OF EMBODIMENT

Suture Placement Device with Telescoping Curved Guides

In this embodiment, each guide comprises two or more telescoping curved guide segments which may be expanded to form a suture path from the cannular housing of the suture placement device, through a tissue insertion point, and back to an opening in the cannular housing. After a suture is drawn through the telescoped guide segments, the guide segments may be collapsed back into the cannular housing.

In this example, one wing or the pair of wings serves as a fascial plane reference element and one or both stylet guides serves as an injection tube for a TAP block. A mechanical plunger may be used to set the depth of one or both both stylet guides.

DESCRIPTION OF EMBODIMENT

Suture Placement Device with Fixed Hook Stylet Guides

Figure 1B:
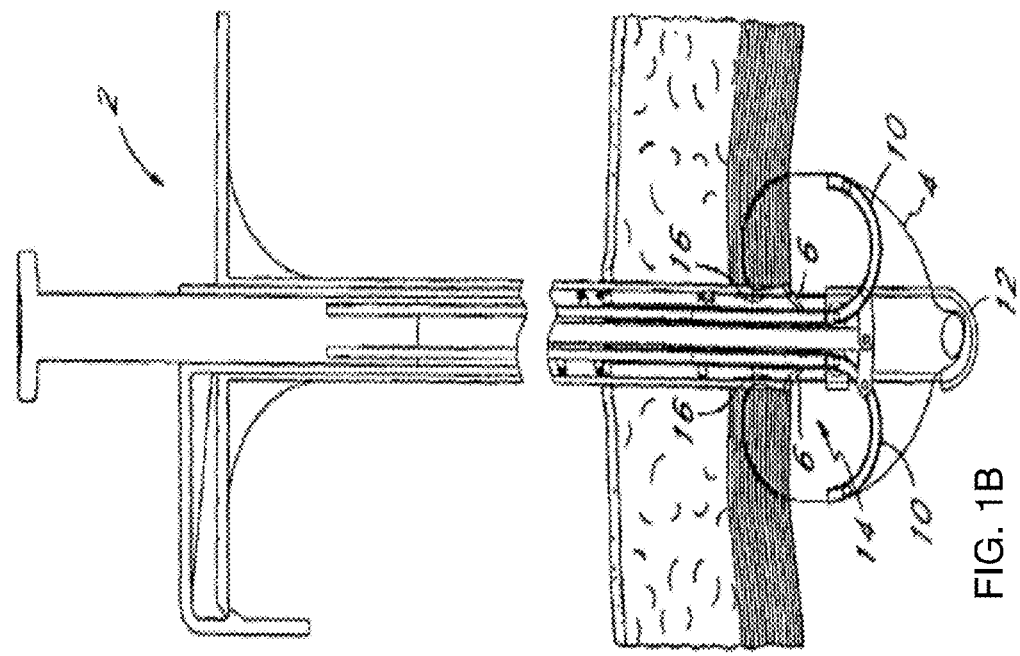
FIGS. 1A-1B show a prior art device of U.S. Pat. No. 7,060,077 to Gordon et al.
Figure 1A:
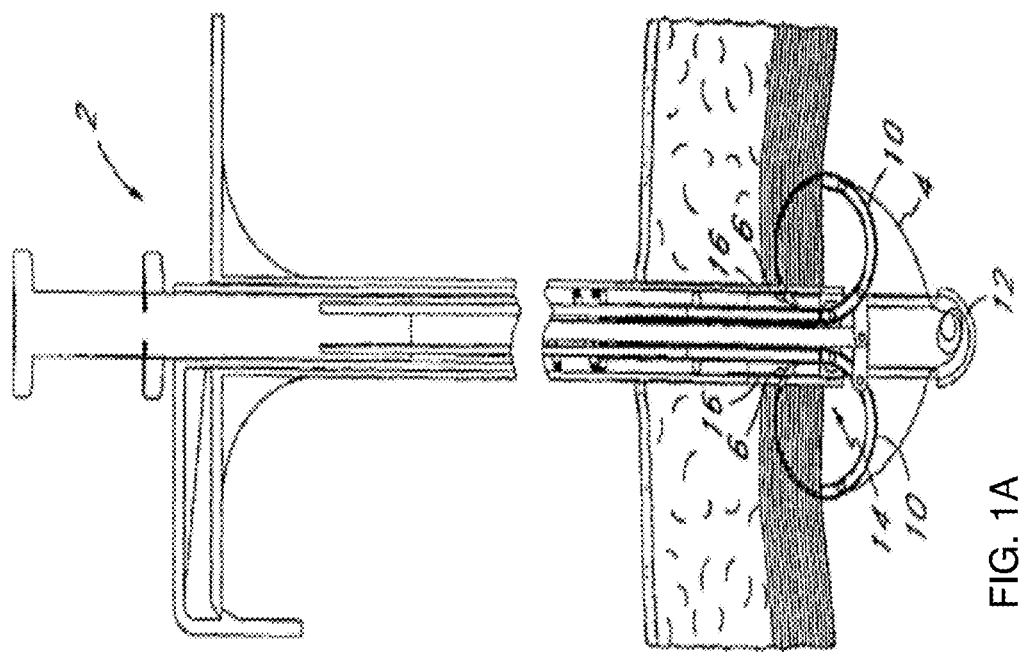
Figure 3:
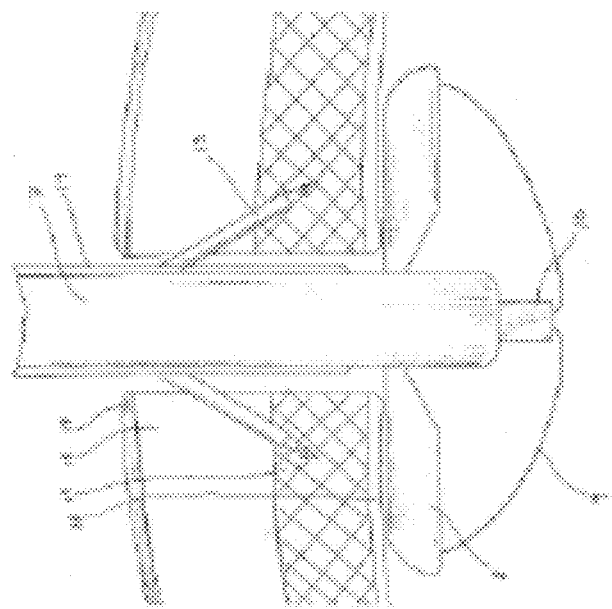
FIG. 3 is a prior art device described in US Patent Application No. 2008/0033459 to 20080033459 to Shafi et al.
Figure 2:
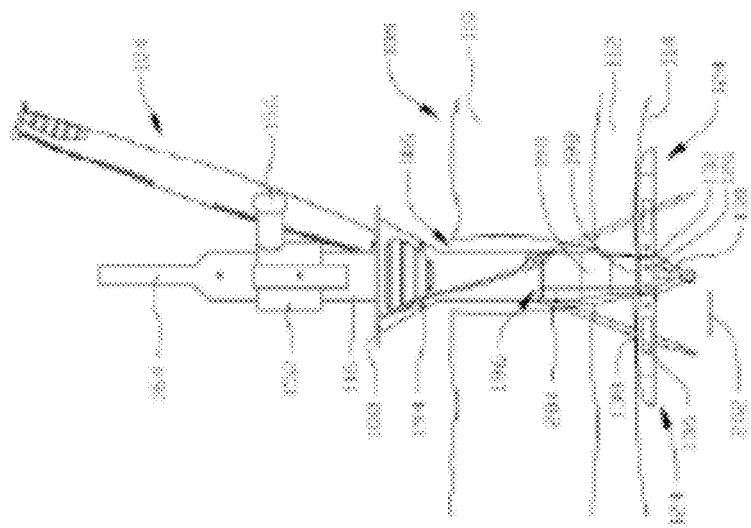
FIG. 2 is a prior art device described in US Patent Application No. 20120035623 to Bagaoisan et al.
Figure 5B:
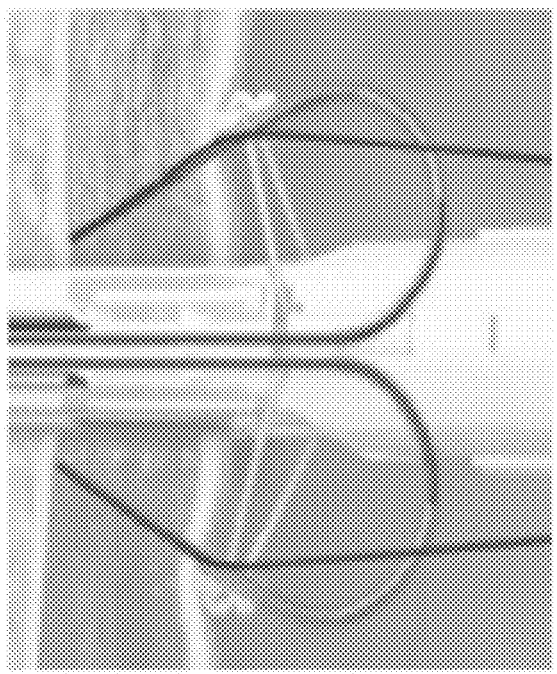
FIGS. 5A and 5B are illustrations of a portion of a prior art Neat Stitch™ closure device.
Figure 5A:
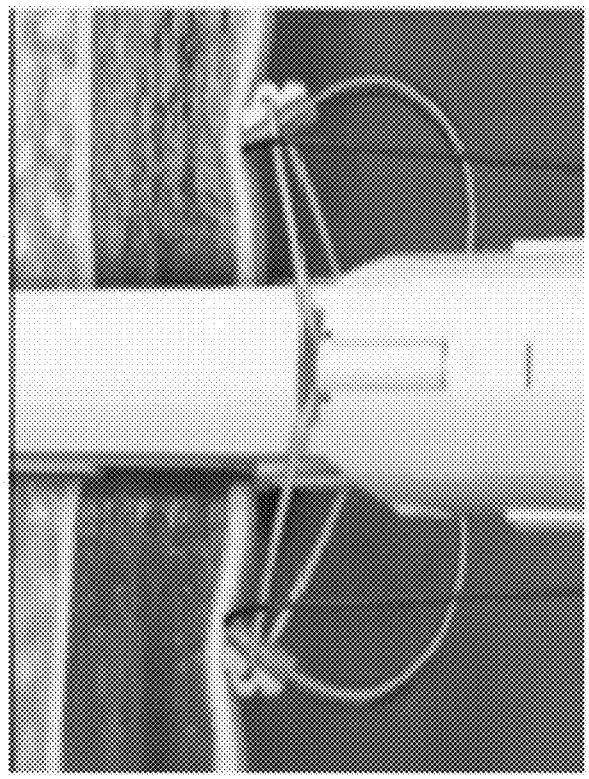
Figure 7:
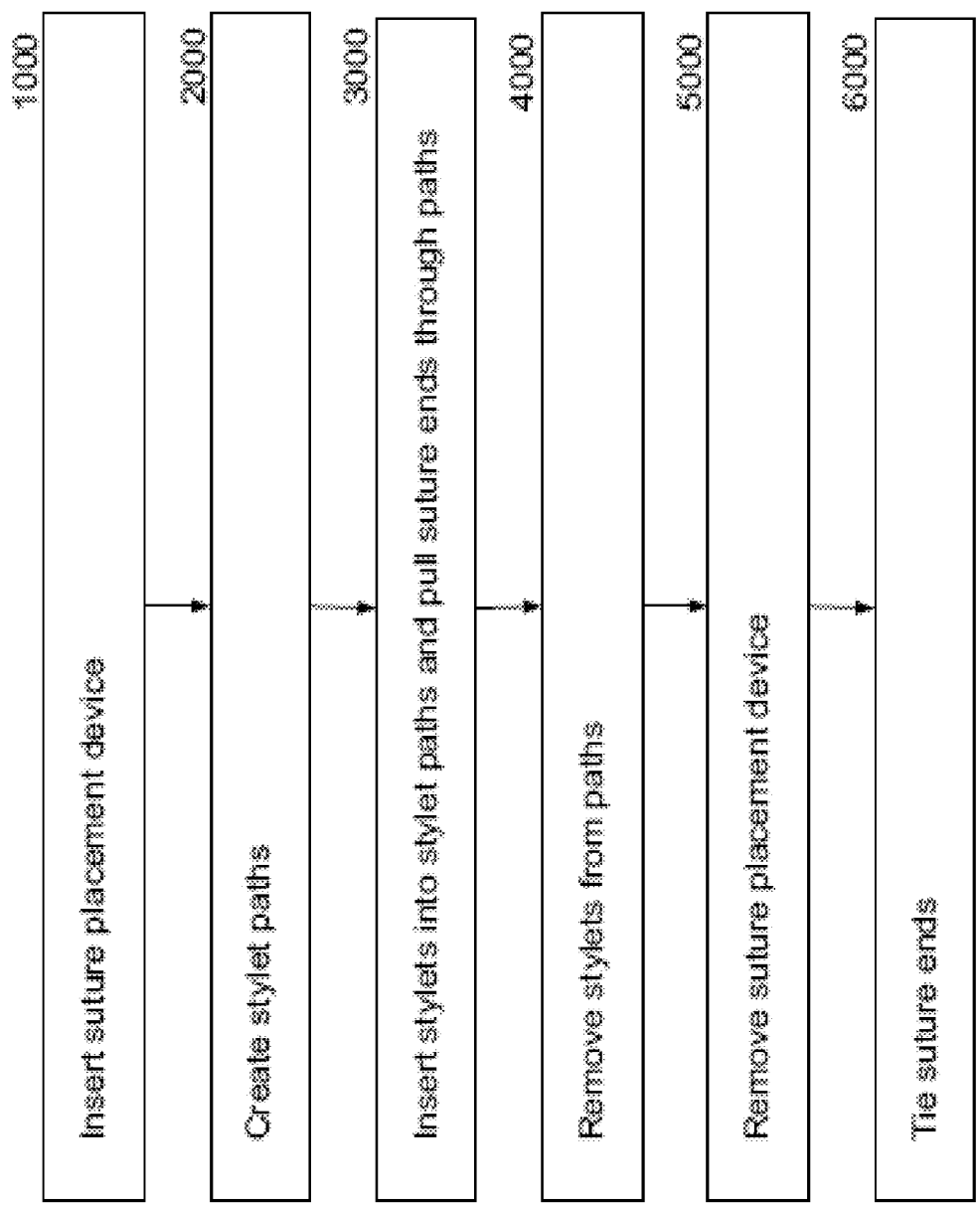
FIG. 7 is a flow chart that summarizes a general method of using a suture placement device to create suture paths, and to use one or more stylets to pull suture through the paths.
Figure 14:
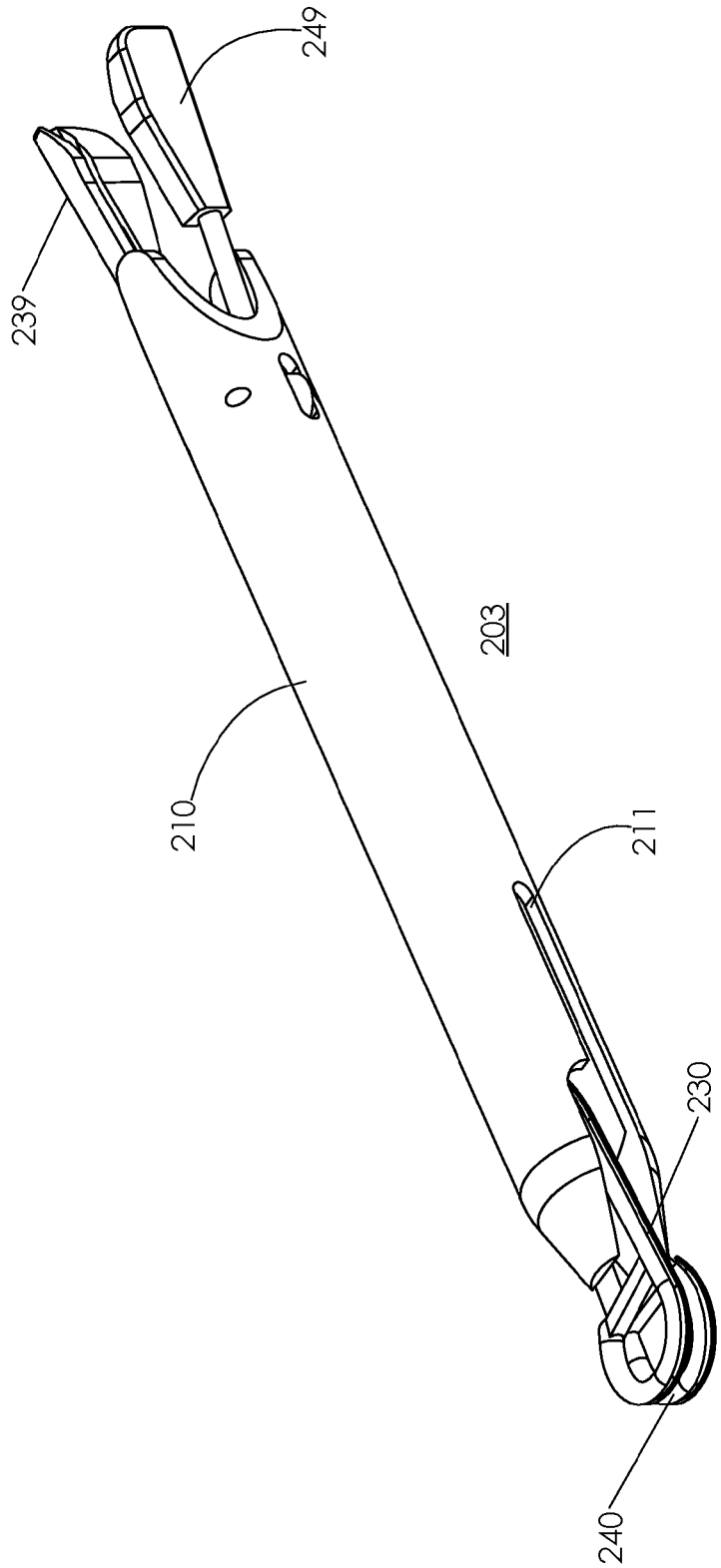
FIG. 14 is a side perspective view of a suture placement device with an extension mechanism which is pair of fixed hooks for guiding tissue-penetrating flexible conduits.

FIG. 14 is a side perspective view of a suture placement device 203. In this example, the suture placement device comprises a cannular housing 210 with an extension mechanism which is pair of fixed hook guides 230 and 240 in an initial closed orientation. The fixed hooks may be extended outwardly from the cannular housing by squeezing the handles 239 and 249 together. The extended provide suture paths through the cannular housing to tissue insertion points. A flexible conduit is used to complete the path from a first tissue insertion point to a first side opening 211 in the cannular housing.

Figure 15:
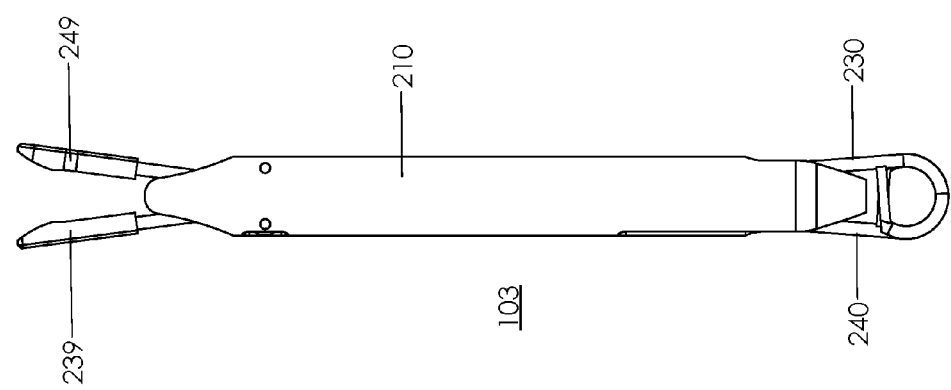
FIG. 15 is a front view of the suture placement device of FIG. 14 with the fixed hook guides in an initial closed orientation.

FIG. 15 is a front view of the suture placement device 203 of FIG. 14 with the fixed hook guides 230 and 240 in an initial closed orientation.

Figure 16:
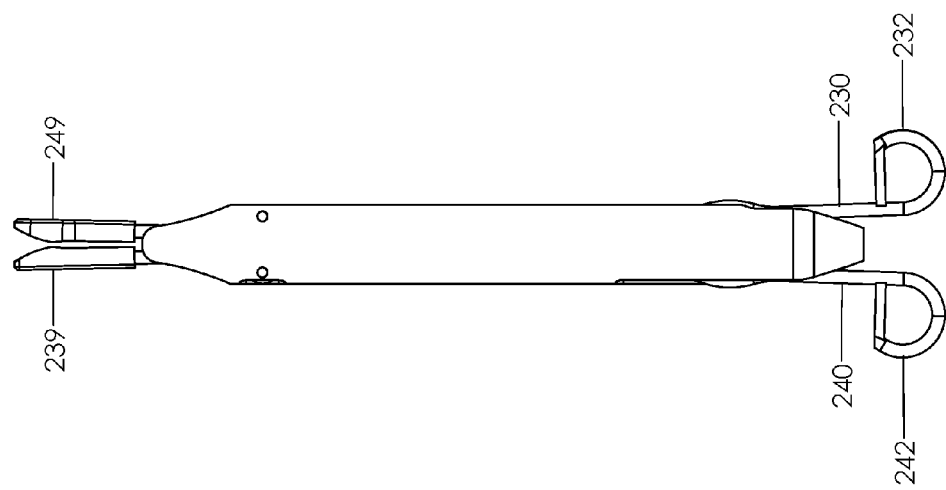
FIG. 16 is a front perspective view of the suture placement device of FIG. 14 with the fixed hook in a deployed orientation.

FIG. 16 is a front perspective view of the suture placement device 203 of FIG. 14 with handles 239 and 249 pushed together to extend the lower hook portions 232 and 242 of extension mechanism fixed hook guides 230 and 240 into a deployed orientation.

Figure 17:
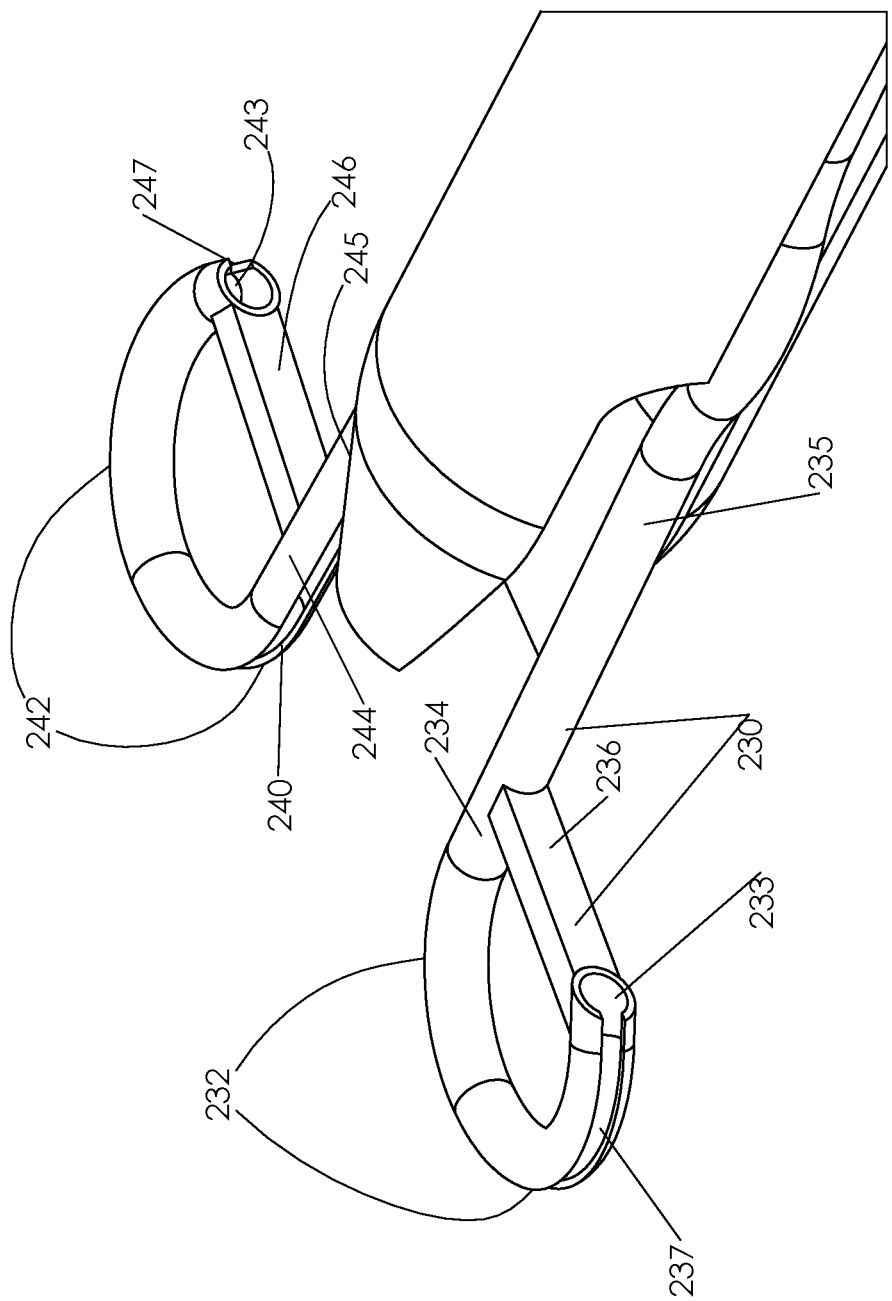
FIG. 17 is a side perspective close-up view of the lower hook portions of the fixed hook of FIG. 16 in an extended deployed orientation.

FIG. 17 is a side perspective close-up view of view of the lower hook portions 232 and 242 of fixed hook guides 230 and 240. Fixed hook guide 230 includes a longitudinal section 235, a lower hook portion 232, and a cross member 236 which extends from the distal end 233 of the hook portion to a proximal end 234 connected to the longitudinal section 235. The longitudinal section 235 and the lower hook portion 232 form a portion of a suture path. The hook portion 232 includes a suture release slot 237 which extends along the outside of the hook portion from the distal end 233 of the hook section to the longitudinal section 235. The cross member 236 provides a relatively large surface area so that the device can be pulled upward against the fascia.

Fixed hook guide 240 includes a longitudinal section 245 a lower hook portion 242 and a cross member 246 which extends from the distal end 243 of the hook portion to a proximal end 244 connected to the longitudinal section 235. The longitudinal section 245 and the lower hook portion 242 form a portion of a second suture path. The hook portion 242 includes a suture release slot 247 which extends along the outside of the hook portion from the distal end 243 of the hook section to the longitudinal section 245.

Figure 18:
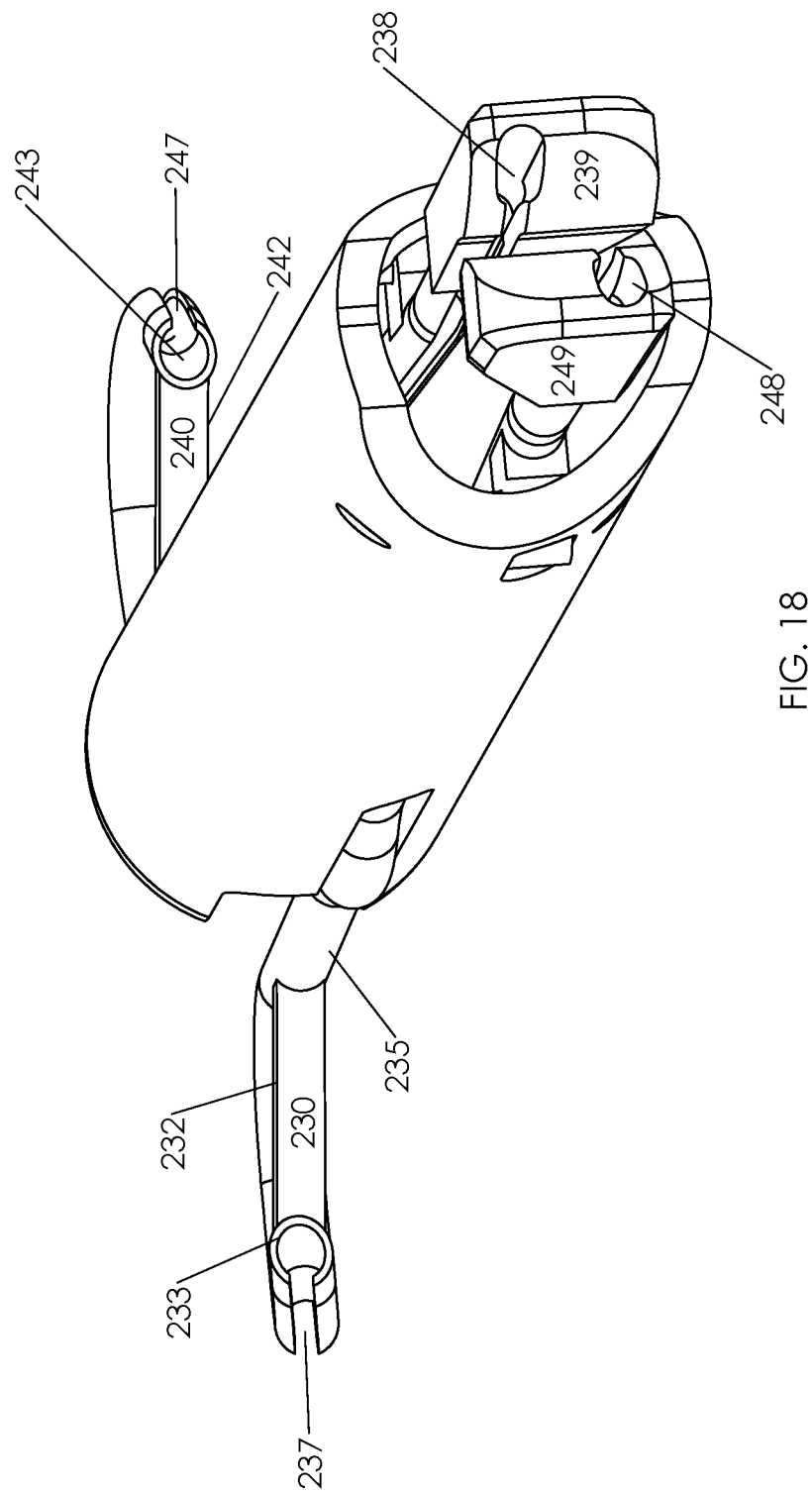
FIG. 18 is a top perspective view of the suture placement device of FIG. 14.

FIG. 18 is a top perspective view of the suture placement device of FIGS. 14-17. Fixed hook guide 230 has a proximal opening 238 in proximity to handle 239. Fixed hook guide 230 provides a path for a stylet or flexible conduit from the proximal end opening 238 through longitudinal section 235 and through hook portion 232. The hook portion 232 includes a suture release slot 237 which extends along the outside of the hook portion from the distal end 233 of the hook section to the longitudinal section 235.

Fixed hook guide 240 has a proximal end opening 248 in proximity to handle 249. Fixed hook guide 240 provides a path for a stylet or flexible conduit from the proximal end opening 248 through longitudinal section 245 and through hook portion 242. The hook portion 242 includes a suture release slot 247 which extends along the outside of the hook portion from the distal end 243 of the hook section to the longitudinal section 245.

Figure 19B:
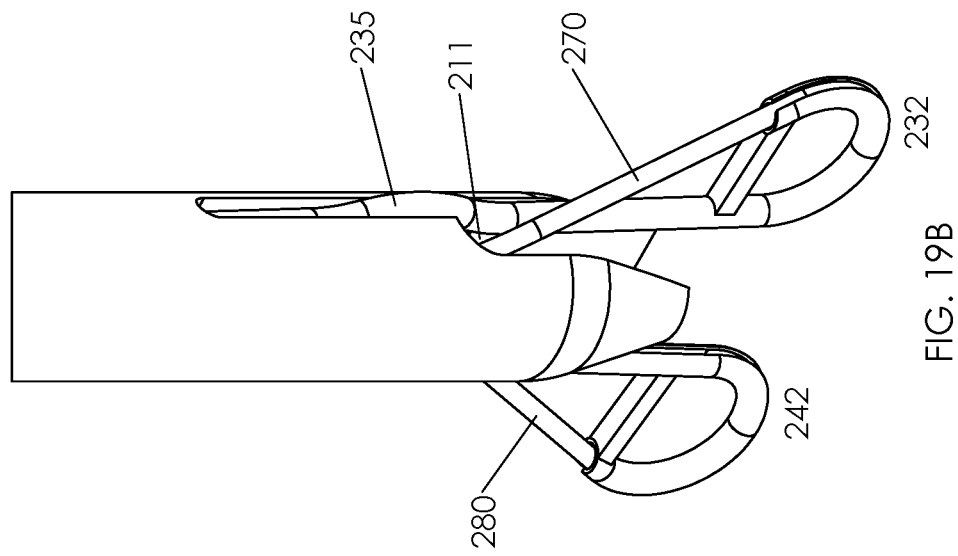
FIG. 19B is a side perspective view of the lower portion of the fixed hook guides of FIG. 16.
Figure 19A:
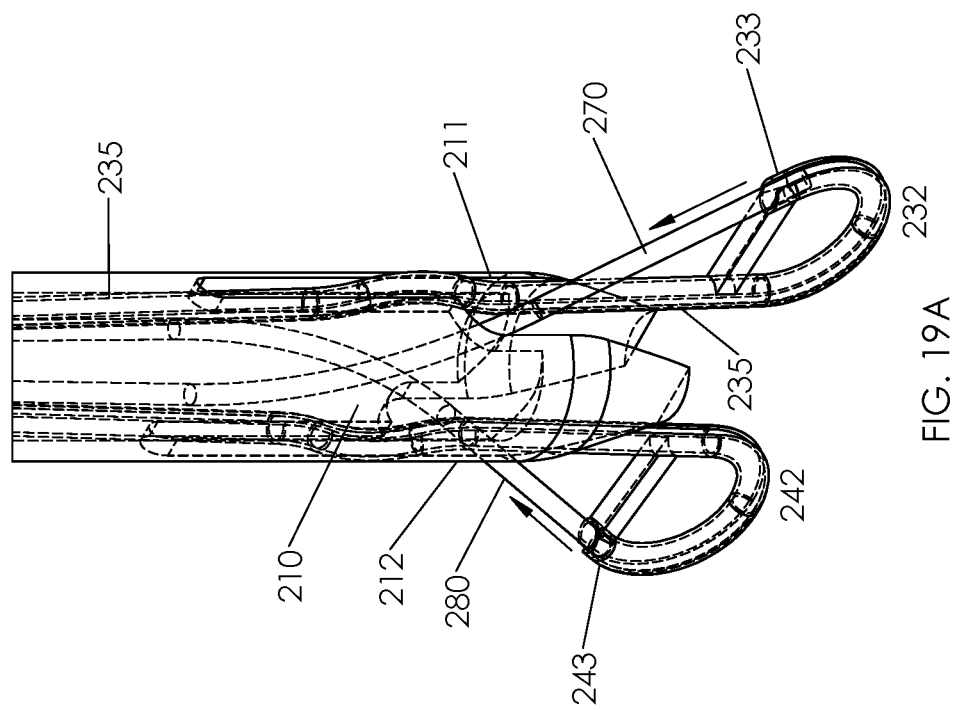
FIG. 19A is a side perspective hidden line view of the lower portion of the fixed hook guides of FIG. 16.

FIG. 19A is a side perspective hidden line view of the lower portion of fixed hook guides 230 and 240 in an extended orientation. FIG. 19B is a side perspective view of the lower portion of guides 230 and 240 in an extended orientation. The tip of a first flexible conduit 270 is inserted down the longitudinal section 235 of guide 230 and through the hook portion 232. The tip and leading portion of the first flexible conduit 270 exits the distal end 233 of hook portion 232 and is pushed into the first side opening 211 in the cannular housing 210. The tip of the first flexible conduit is pushed through the first side opening 211 and up the inside of the cannular housing until the tip rests between the first side opening 211 and the proximal end of the cannular housing. As described below, a first stylet is inserted into the first flexible conduit in order to pull the first end of a suture through the guide 230.

The tip of a first flexible conduit 280 is inserted down the longitudinal section 245 of guide 240 and through the hook portion 242. The tip and leading portion of the first flexible conduit 270 exits the distal end 243 of hook portion 242 and is pushed into the second side opening 212 in the cannular housing 210. The tip of the first flexible conduit is pushed through the second side opening 212 and up the inside of the cannular housing until the tip rests between the first side opening 212 and the proximal end of the cannular housing. As described below, a second stylet is inserted into the first flexible conduit in order to pull the first end of a suture through the guide 240.

Method of Use

Figure 20:
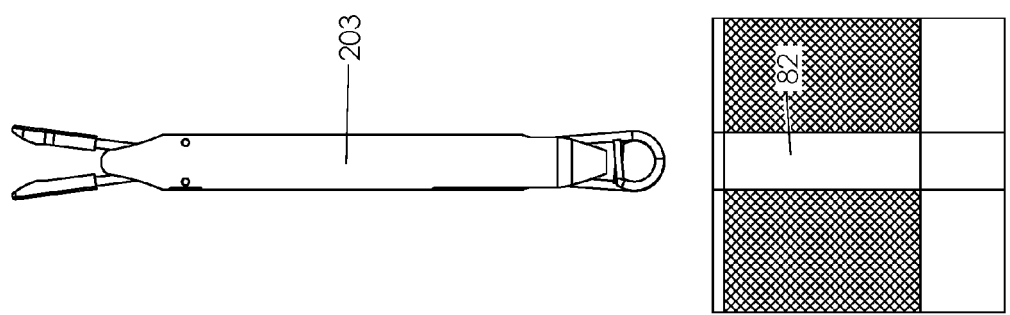
FIG. 20 is a front view of a suture placement device of FIG. 14 insertion into a tissue defect made by the trocar device.

FIG. 20 is a front view of a suture placement device 203 positioned for insertion into a hole 82 in tissue.

Figure 21:
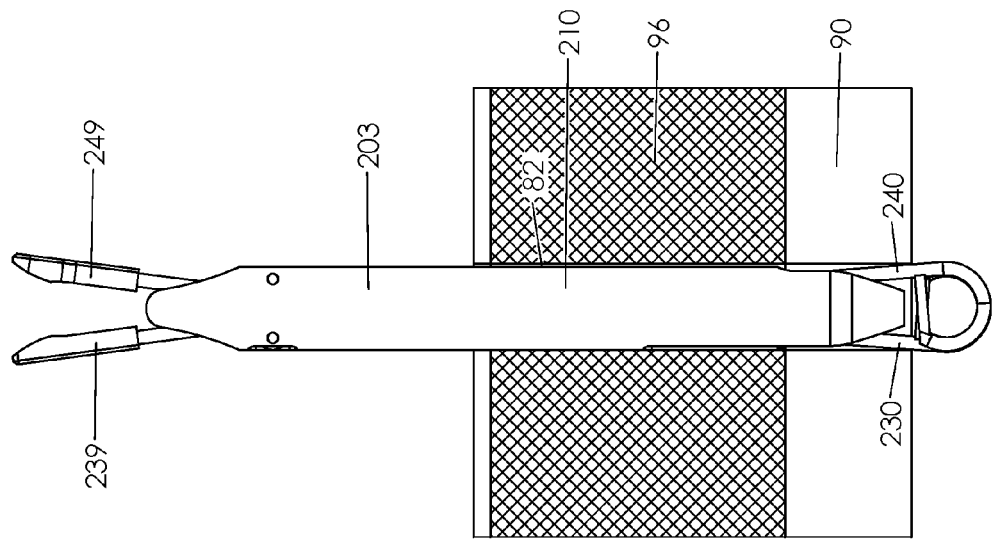
FIG. 21 is a front view of the suture placement device of FIG. 14 inserted into a tissue defect in the abdominal wall with the device in an initial closed orientation.

FIG. 21 is a front view of a suture placement device 203 inserted into a hole 82 in tissue. A fat layer 96 and fascia 90 are shown. In this example, the suture placement device comprises a cannular housing 210 with a pair of fixed hook guides 230 and 240 in an initial retracted orientation to permit the cannular housing to be inserted into the hole 82.

Figure 22:
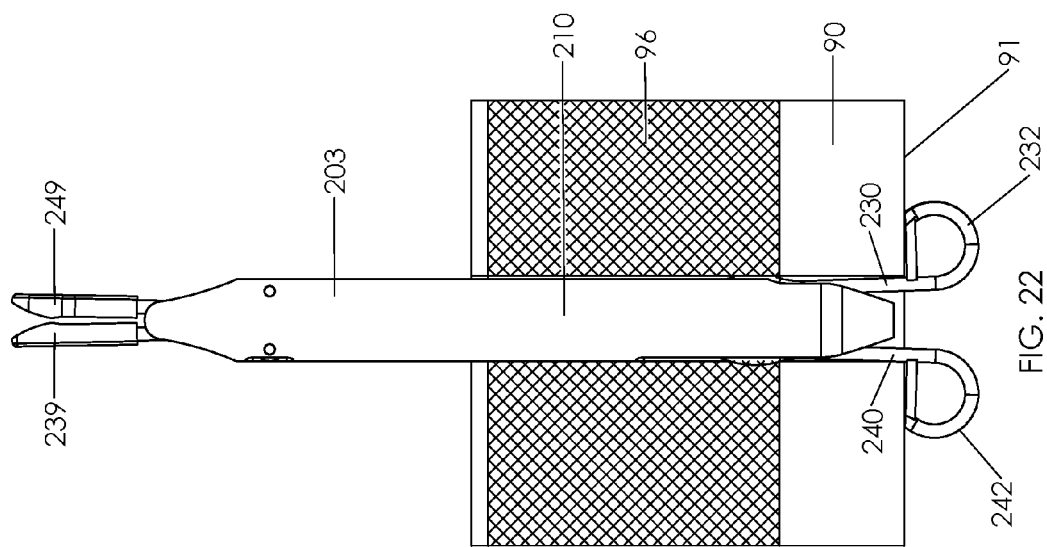
FIG. 22 is a front perspective view of the suture placement device of FIG. 20 with the pair of fixed hook guides in a deployed orientation.

FIG. 22 is a front view of the suture placement device 203 with the pair of fixed hook guides 230 and 240 in a deployed orientation. In this example, when handles 239 and 249 are squeezed together, the hook portions 232 and 242 of stylet guides are deployed outwardly in a scissoring movement from a closed orientation to the deployed orientation of the extension mechanism.

Cross members 236 and 246 engage the abdominal wall so that the surgeon can pull the suture placement device upwardly.

Figure 23:
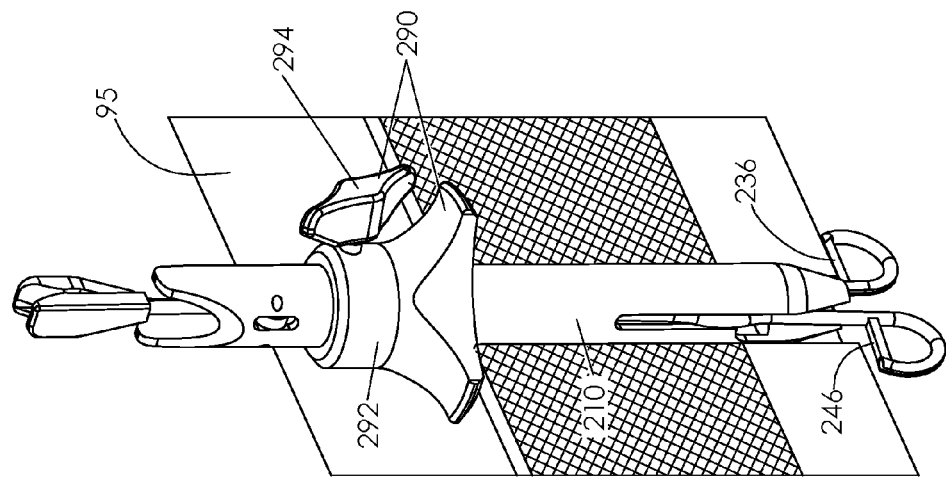
FIG. 23 is a front perspective view of suture placement device of FIG. 20 with an adjustable clamp mechanism.

FIG. 23 is a front perspective view of suture placement device 203 and an adjustable clamp mechanism 290 which is provided to secure the cannular housing in the hole 82. The adjustable clamp fits over the cannular device and can be adjusted to stabilize the closure device by acting as a clamp to squeeze the abdominal wall contents while the stylet is placed through the innermost layers of the abdominal cavity. In this example, the clamp mechanism 290 includes a clamp 292 which may be lowered along the outside surface 210 of the cannular housing until the clamp 292 is brought into contact with the skin 95. The clamp locking element 294 is then engaged to hold the clamp against the skin. The combination of the clamp against the skin and the cross members 236 and 246 hold the suture placement device 103 in place so that the surgeon's hands are free.

In another example, the adjustable clamp can be slid over the cannular device and adjusted into place with a "worm-gear" mechanism to tighten the abdominal wall around the closure device; the clockwise turn of the knob will bring the clamp down onto the skin surface (thereby tightening the abdominal wall contents between the wings and the clamp); and counter-clockwise turn of the knob will bring the clamp away from the skin surface (thereby loosening the grip held between the wings and the clamp surface).

Flexible Conduit

In one example, a first flexible conduit 270 is used to establish a path from the distal end 233 of the fixed hook guide 230 through the fascia and back to the cannular housing. The first end of a first flexible conduit is inserted into proximal end opening 238 of the first guide 230 and pushed through the longitudinal section 235 until it emerges from distal end 233. A continued pushing of the flexible conduit pierces the fascia and directs the first end of the flexible conduit into a first side opening 211 in the side of the cannular housing, and then up the inside of the cannular housing. In one example, the tip of the flexible conduit emerges from the proximal end of the cannular housing. In another example, the tip of the flexible conduit is stopped in the cannular housing between the side opening 211 and the proximal end of the cannular housing and a stylet inserted through the flexible conduit will emerge through the proximal end of the cannular housing.

This process is repeated with a second flexible conduit 280 inserted into the proximal end opening 248 of the second guide 240.

A first suture end is removable affixed to a first stylet, and the first stylet is pushed into the first flexible conduit. The first stylet 300 travels in the flexible conduit through the longitudinal section 235 of the guide, through the distal end 233 of the guide, and to the cannular housing. A continued pushing of the stylet forces the stylet through the flexible conduit and through the tip of the flexible conduit until the stylet emerges from the proximal end of the cannular housing. The first end of the suture is removed from the first stylet.

A second stylet 310, without any suture attached, is inserted into the proximal end of the second flexible conduit 280 until the leading end of the stylet emerges from the proximal end of the cannular housing. The first end of the suture is attached to the leading end of the stylet, the stylet is withdrawn from the second flexible conduit 280 until the first end of the suture emerges from the second flexible conduit, and the first end of the suture is removed from the second stylet. In this example, the first stylet 300 may also serve as the second stylet 310.

The suture is held while the first flexible conduit 270 and the second flexible conduit 280 are removed from the housing and pulled over the second and first ends of the suture, respectively.

Dual Flexible Conduit

Figure 24:
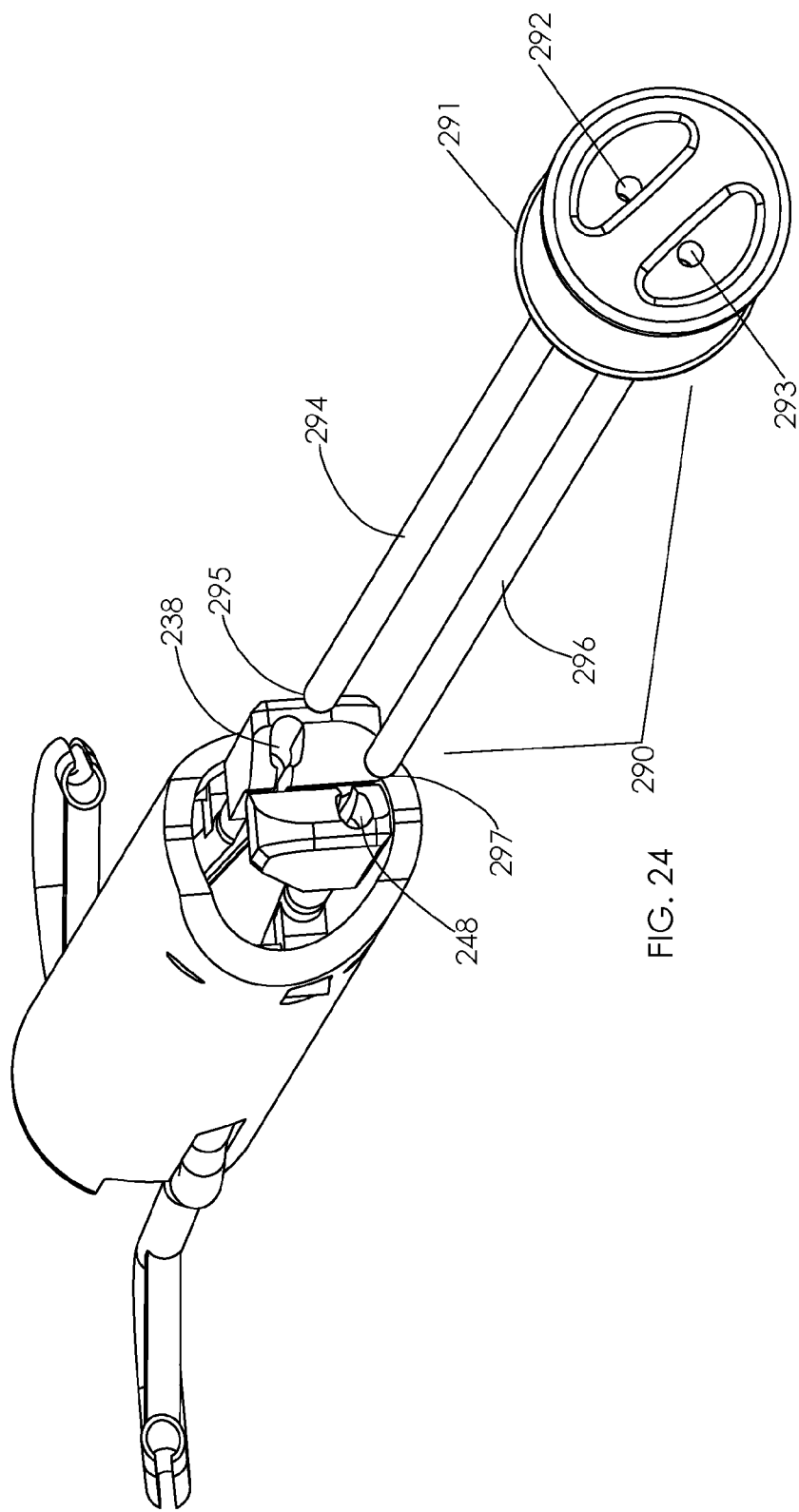
FIG. 24 is a top perspective view of the suture placement device of FIG. 20 with a dual flexible conduit.

FIG. 24 shows a dual flexible conduit 290 comprising a proximal end 291 with a first stylet entry port 292 and a second stylet entry port 293.

A first flexible conduit shaft 294 extends from the first stylet entry port 292 to a tip 295. A second flexible conduit shaft 296 extends from the second stylet entry port 293 to a tip 297. Tips 295 and 297 are configured to be inserted into the proximal openings 238 and 248 of stylet guides 230 and 240 respectively.

Figure 32:
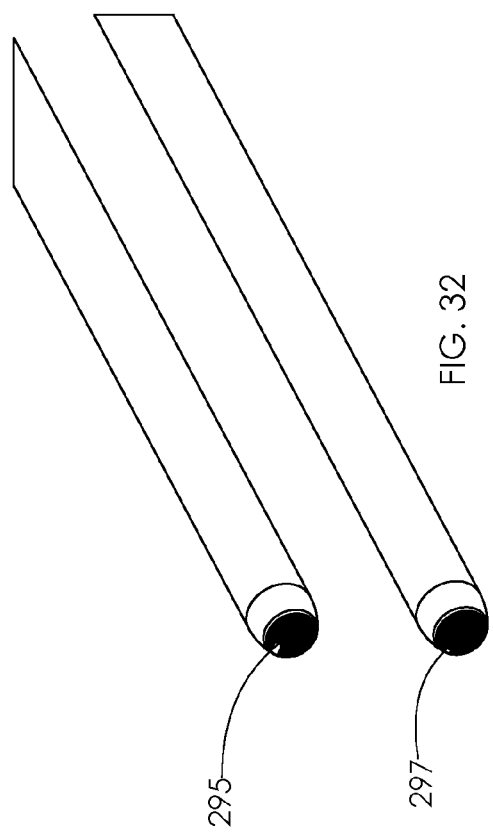
FIG. 32 is a detailed side perspective view of the tapered ends of a dual flexible conduit with a groove on the lateral aspect.

FIG. 32 is a closeup side perspective view of a portion of the first flexible conduit shaft 294 and the second flexible conduit shaft 296 with tips 295 and 297.

Figure 25:
FIG. 25 is a front view of the suture placement device of FIG. 24 with the dual flexible conduit positioned to be inserted into the fixed hook guides.

FIG. 25 is a front view of the dual flexible conduit 290 positioned for insertion into fixed hook guides 230 and 240.

Figure 26:
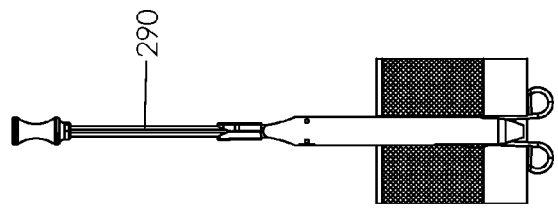
FIG. 26 is a front view of the suture placement device of FIG. 25 with a dual flexible conduit and a pair of stylets partially inserted into the stylet guides.

FIG. 26 is a front view of the suture placement device of FIG. 25 with a dual flexible conduit and a pair of stylets partially inserted into the stylet guides.

Figure 27:
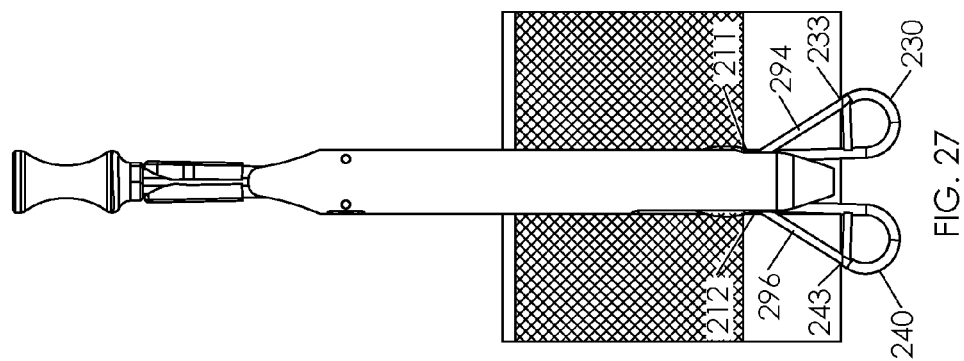
FIG. 27 is a front view of the suture placement device of FIG. 26 with the dual flexible conduit fully inserted into the stylet guides.

FIG. 27 is a front view of the suture placement device of FIG. 26 with the dual flexible conduit fully inserted into the stylet guides. First flexible conduit shaft 294 has penetrated the fascia from the distal end 233 of the hook portion of guide 230 and provides a suture path through guide 230 and back to the first side opening 211 in the cannular housing 210. Second flexible conduit shaft 296 has penetrated the fascia from the distal end 243 of the hook portion of guide 240 and provides a suture path through guide 240 and back to the first side opening 212 in the cannular housing 210.

Figure 28:
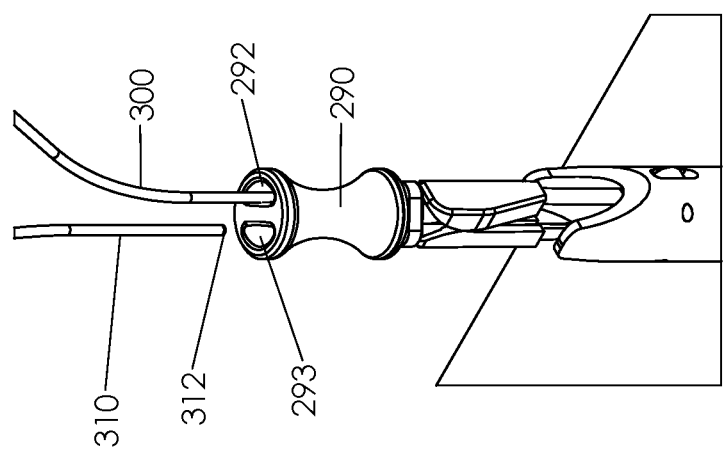
FIG. 28 is a top perspective view of the suture placement device of FIG. 27 with the dual flexible conduit and a pair of stylets.

FIG. 28 is a top perspective view of the suture placement device of FIG. 27 with the dual flexible conduit 290 and a pair of stylets 300 and 310. Stylet 300 has been inserted into the first stylet entry port 292 of the flexible conduit, and tip 312 of stylet 310 is positioned for insertion into the second stylet entry port 293 of the flexible conduit.

Figure 29:
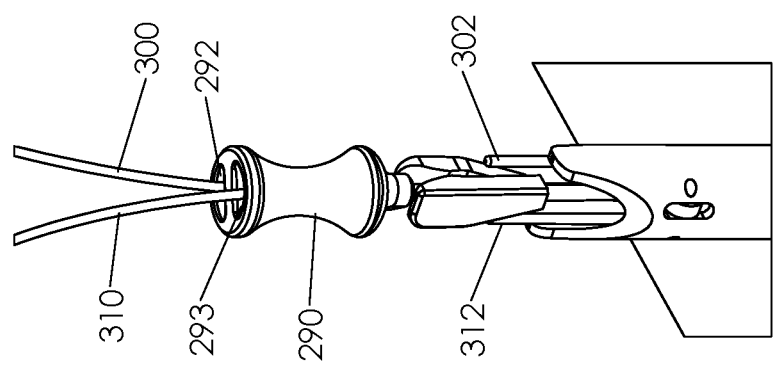
FIG. 29 is a side perspective view of the suture placement device of FIG. 27 with a pair of stylets inserted into the dual flexible conduits until the tips of the stylets emerge from the proximal end of the cannular housing.

FIG. 29 is a side perspective view of the suture placement device of FIG. 29 with the pair of stylets 300 and 310 inserted into the dual flexible conduit shafts until the tips 302 and 312 of the stylets have emerged from the proximal end of the cannular housing.

At this point, the stylet tips 302 and 312 may be grasped by fingertip and squeezed against the handles 339 and 349 while the dual flexible conduit 290 is pulled upward over the stylets 300 and 310.

Figure 30:
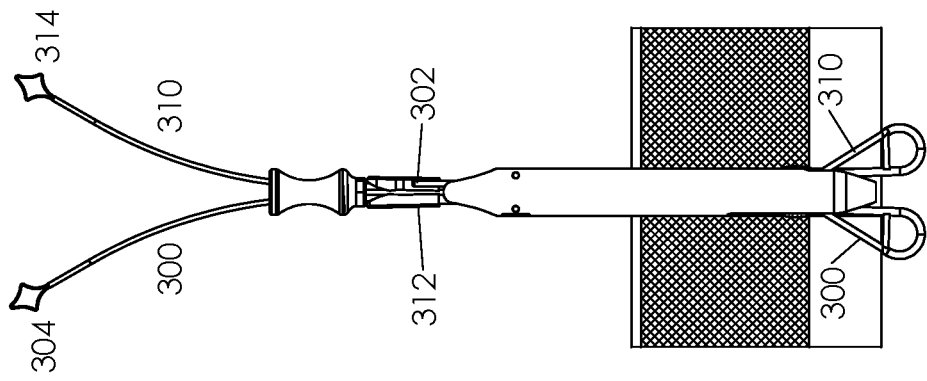
FIG. 30 is a side perspective view of the suture placement device of FIG. 27 with the dual flexible conduit removed.

FIG. 30 is a side perspective view of the suture placement device of FIG. 29 with the dual flexible conduit removed. Portions of stylets 300 and 310 are shown extending from the distal ends of the stylet guide hook portions back to the openings 211 and 212 in the cannular housing. The stylets are routed up the cannular housing until their tips emerge from the housing. At this point, the stylets may be pushed or pulled further through the guides in order to pull the ends of a suture through the guides.

A first suture end is removable affixed to end 304 of first stylet 300, and end 303 of stylet 300 is pulled through the device until the first stylet 300 and the first suture end are pulled out of the housing. The first suture end is then attached to end 312 of the second stylet, and the second stylet is removed from the device by pulling end 304.

The suture may be pulled through the device with the stylets in this manner before the dual flexible conduit 290 is removed, and the dual flexible conduit can be removed over the suture.

Device Removal

Figure 31:
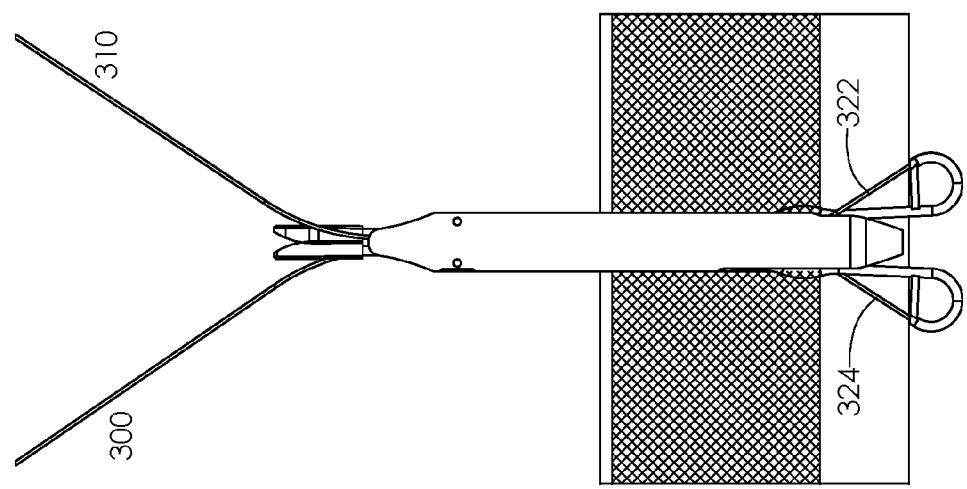
FIG. 31 is a front view of the suture placement device of FIG. 30 with suture extending through the proximal end of the cannular housing.

FIG. 31 is a front view of the suture placement device of FIG. 30 with a suture 320 extending through the proximal end of the cannular housing. Suture segments 322 and 324 have been routed through the fascia.

The suture placement device is withdrawn by moving the extension mechanism fixed hook guides 230 and 240 back to their initial closed orientation by spreading handles 239 and 249 apart and removing the device. The suture is then tied.

TAP or Other Substance Introduction

In this example, one or both fixed hook guides 230 and 240 serves as a fascial plane reference element and one or both stylet guides serves as an injection tube. A mechanical plunger may be used to set the depth of the stylet guides. The desired depth of the distal end of the stylet guides may be set with a fixed mechanical stop or an adjustable mechanical stop on the plunger, or manually with the help of a user guide such as one or more color coded bands or ruling on the suture placement housing that correspond to distance or a range of distance of the stylet guide tips above the the pair of fixed hooks. In some cases, a single stylet guide can provide a single injection, and the injected substance will spread or migrate completely around a trocar port site. In other cases, a two stylet guides can be used to inject a substance on opposite sides of a trocar port site. An adapter may be provided to simultaneously introduce a substance or mixture to both stylet guides.

DESCRIPTION OF EMBODIMENT

Suture Placement Device with Pivot Bar and Stylet Guides Deployed Downwardly from Housing In this embodiment, a pair of flexible stylet guides are deployed downwardly and outwardly from opposite sides of a cannular housing. The distal end of each guide engages a receptor port on a pivot bar element which is deployed from the housing. The stylet guides penetrate tissue with sharp bevel-shaped tips that create a suture path segment for a stylet through the hollow guide. When engaged in the receptor ports, the stylet guides hold the suture placement device in position so that the trocar port can be removed over the suture placement device.

An extension mechanism, a pivot bar, is deployed from the housing, and positioned below the fascia. A channel is provided in the pivot bar, and extends from a receptor port on each side of the pivot bar, such that the receptor ports are located about 1 cm from opposed sides of the outside of the cannular housing. When the stylet guides are fully deployed, the distal end of each stylet guide engages a receptor port, thereby creating a suture path through the first stylet guide, into the first receptor port, through the channel, through the second receptor port, and through the second stylet guide. A stylet is then directed through the suture path to pull the first end of a suture through the path. After routing the suture, the stylet guides are refracted, leaving the suture routed through the fascia. The pivot bar has a suture release slot along the bottom of the pivot bar, and the suture is released through the suture release slot as the pivot bar is rotated back to a folded position. The suture placement device is withdrawn and the suture is tied.

Figure 43C:
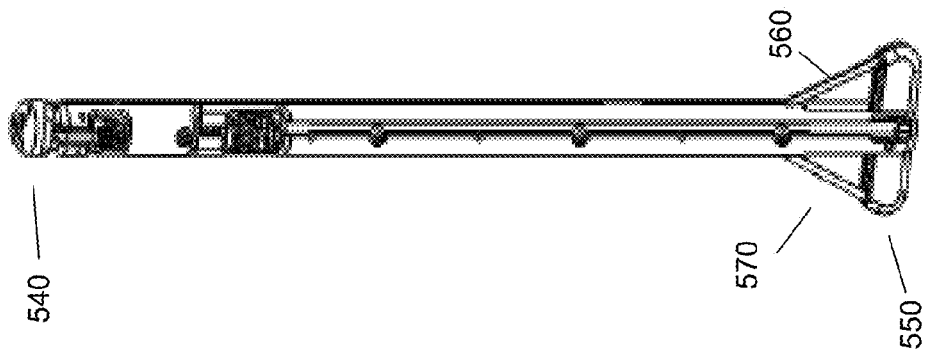
FIG. 43C is a side perspective view of the embodiment of the suture placement device of FIG. 43A with a a first and second guide deployed to engage the pivot bar wing.
Figure 43B:
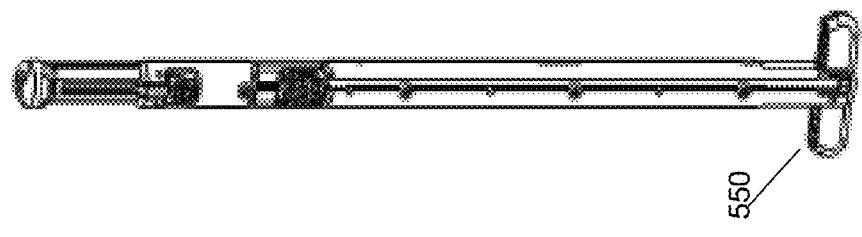
FIG. 43B is a side perspective view of the embodiment of the suture placement device of FIG. 43A with a pivot bar wing deployed.
Figure 43A:
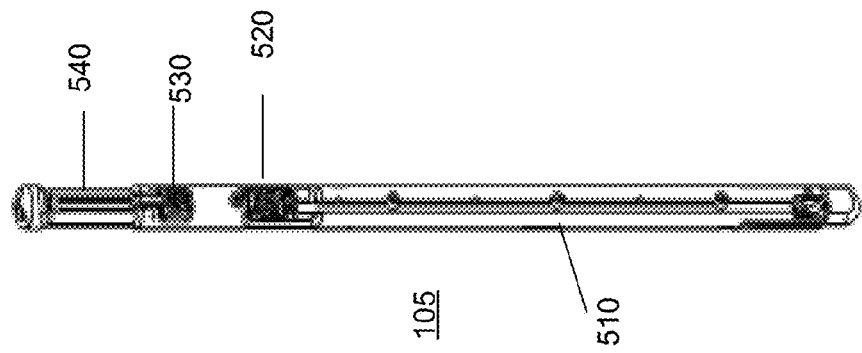
FIG. 43A is a side perspective view of another embodiment of a suture placement device.

FIG. 43A is a side perspective view of suture placement device 105 showing a body 510, a pivot bar actuation slide 520, a guide latch 530, and a guide plunger 540.

FIG. 43B is a side perspective view of the suture placement device with the extension mechanism pivot bar 550 deployed by sliding the pivot bar actuation slide 520.

FIG. 43C is a side perspective view of the suture placement device with a first stylet guide 560 and a second stylet guide 570 deployed engaging receptor ports 554 and 555 on the pivot bar 550. In this example, the first guide and second guide are deployed by pressing the guide plunger 540.

Figure 43D:
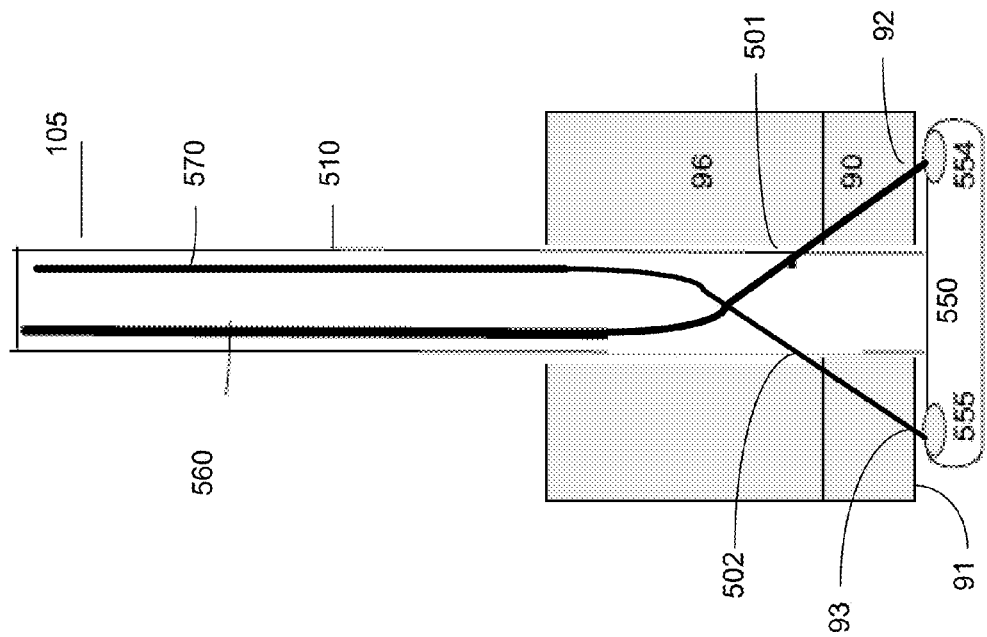
FIG. 43D shows the suture placement device of FIG. 43A inserted into tissue fat and fascia layers.

FIG. 43D shows suture placement device 105 inserted into a tissue opening through the fascia layer 90 and fat layer 96. The first guide 560 and the second guide 570 are deployed through the fascia layer 90. A pivot bar 550 at the lower end of the suture placement device has been pivoted to move the pivot bar to an extended orientation below the fascia layer 91. In this example, the extended pivot bar is perpendicular to the longitudinal axis of the suture placement device.

The first stylet guide 560 has created a suture path through the fascia layer 90 from an opening opening 501 in the cannular housing 510 to point 92 in the fascia above the first side of the pivot bar. The second stylet guide 570 has created a suture path through the fascia 90 from the opening 502 in the cannular housing 510 to point 93 in the fascia.

The pivot bar can engage the fascia 91 so that the surgeon can pull the suture placement device upwardly.

In this example, a clamp is not necessary to secure the suture placement device, and the suture placement device can be operated with a single hand as the deployed guides hold the device in place.

Creating the Suture Path

FIG. 44A shows a stylet 580 partially inserted into the first guide of the suture placement device. FIG. 44B shows the stylet 580 inserted into the extended first guide 560 and pivot bar channel 551 of the suture placement device. FIG. 44C shows further insertion of the stylet to create a suture path through the first guide 560, through the pivot bar channel 551, and through the second guide 570. The first end 581 of the stylet has emerged from the suture placement device. As described below, a suture may be temporarily attached to the first end of the stylet, so that the suture is positioned in the suture path as the stylet is retracted back through the suture path. In other examples, the suture may be temporarily attached to the second end of the stylet, so that the suture is positioned in the suture path as the stylet is pulled through the suture path until the second end of the stylet emerges from the proximal end of second stylet guide 570.

FIG. 44D shows the first end portion of a suture 590 attached to the second end 582 of stylet 580, so that the stylet can pull the suture through the suture path. FIG. 44E shows the stylet 580 pulling the first end of a suture through the first guide 560 and channel 551 of the suture placement device. FIG. 44F shows the stylet pulling the end of a suture through the second guide 570.

FIG. 44G shows the suture 590 positioned after the first guide and second guide are refracted, and the pivot bar is refracted. FIG. 44H shows the suture 590 remaining in place as the suture placement device 105 is partially removed.

In another example, the first end portion of a suture 590 is attached to the first end 581 of the stylet, and the stylet is then retracted until the first end of the stylet and the first end portion of a suture are pulled back through the proximal end of the first stylet guide.

Pivot Bar

FIG. 45 is a side perspective view of a first half 550a of pivot bar 550 showing half of the cross section of channel 551 and half of receptor port features 554 and 555. The outside edge of the channel and the receptor ports have a suture release slot 553. When this half and a second half of the pivot bar are assembled, the pivot bar provides a slotted channel 551 between the first receptor port 554 and the second receptor port 555. The distal end of the first guide engages the first receptor port 554, and the distal end of the second guide engages the second receptor port 555 to create a suture path through the guides, the receptor ports, and pivot bar channel. Suture is pulled through the suture path with a stylet, and is released through the suture release slot 553 as the pivot bar is retracted.

Guide Plunger

FIG. 46A is a top perspective view of the guide plunger 540. FIG. 46B is a bottom perspective view of the plunger 540. The plunger includes stylet ports 542 and 543 and stylet channels 547 and 548. The distal ends of guides 560 and 570 are inserted into lower portion of the stylet channels 547 and 548 so that the guides and be extended or retracted with the plunger. In this example, a stylet is inserted into either of the stylet ports 542 or 543 and routed downward through the corresponding stylet channel into one of the guides, then through the pivot bar channel and back up through the other guide and back upward through the other stylet channel so that the stylet exits the other stylet port. In other examples as described below, a single entry port is provided on the proximal end of the device, and an exit port is provided through the side of the housing. In this example, suture release slots 546 and 547 extend from both stylet channels and stylet ports. In other examples, the suture release slots are not required and the suture remains in position as the device is removed. The guide plunger includes a latch recess 541 and a spring recess 549.

Figure 48:
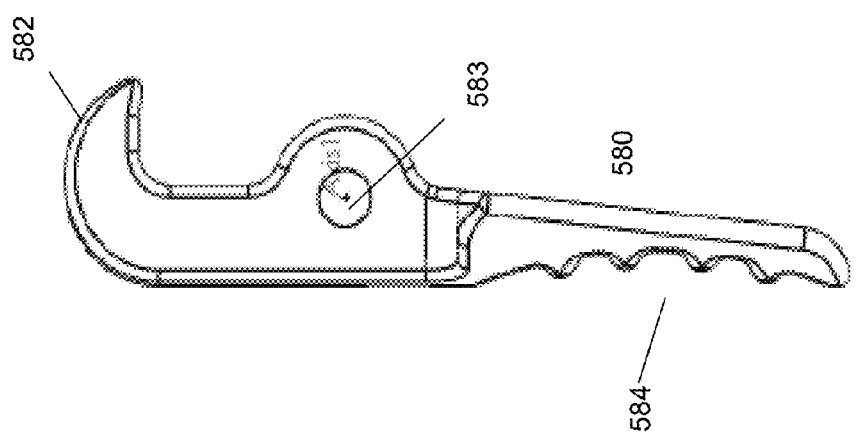
FIG. 48 is a side view of a guide latch for the suture placement device of FIG. 43A.

FIG. 48 is a side view of a guide latch 530 for the suture placement device. The guide latch includes hook 582 for engaging the latch recess 541 of the guide plunger, and pivot hole 583, and a latch grip 584.

Guides

Figure 47C:
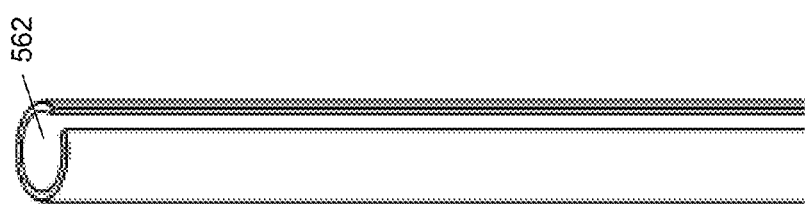
FIG. 47C is a detailed side view of an end of the first guide of FIG. 46A showing a slot on the guide.
Figure 47B:
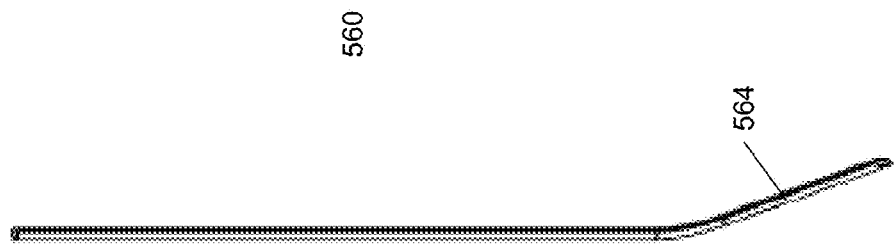
FIG. 47B is a side view of a first guide for the suture placement device of FIG. 43A with the guide in an extended position.
Figure 47A:
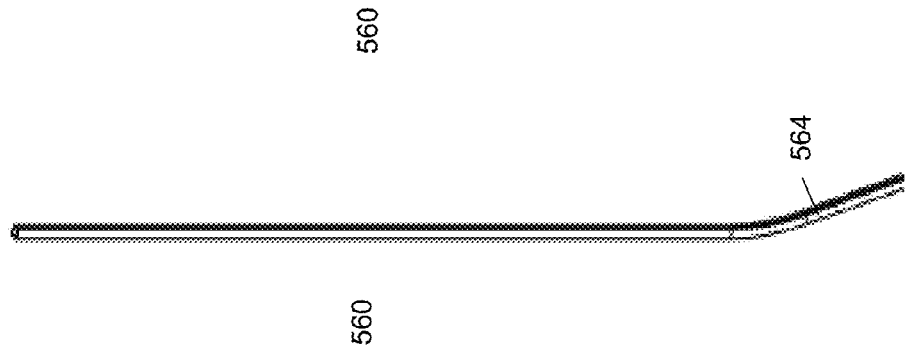
FIG. 47A is a side view of a first guide for the suture placement device of FIG. 43A with the guide in a retracted position.
Figure 54C:
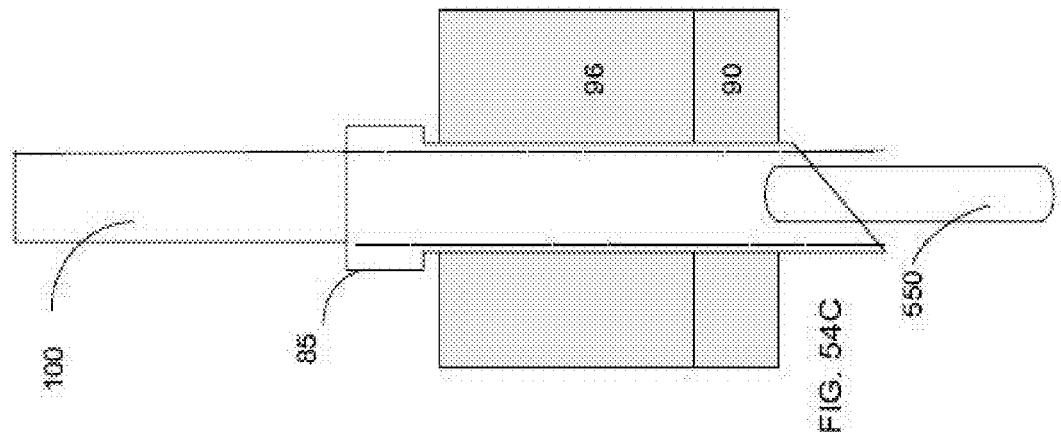
FIG. 54C is a cross section schematic of a suture placement device partially inserted in to the trocar port of FIG. 54A with a pivot bar in a folded position.
Figure 54B:
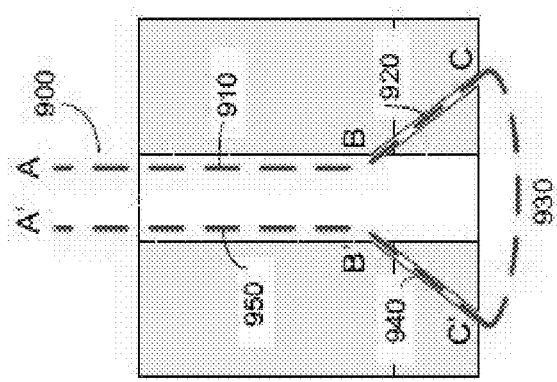
FIG. 54B is a cross section schematic of a trocar insertion site showing ideal suture paths and through the fascia.
Figure 54A:
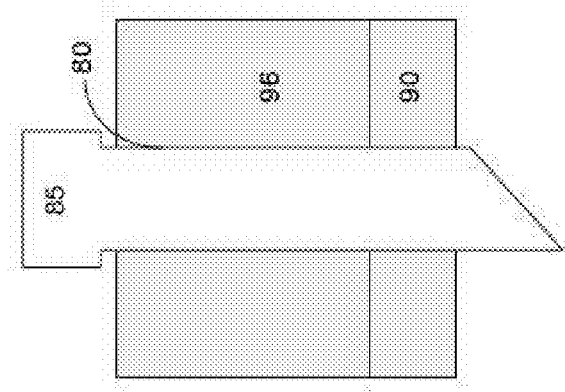
FIG. 54A is a cross section schematic of a trocar port positioned in a trocar insertion site though fat layer and fascia.
Figure 54F:
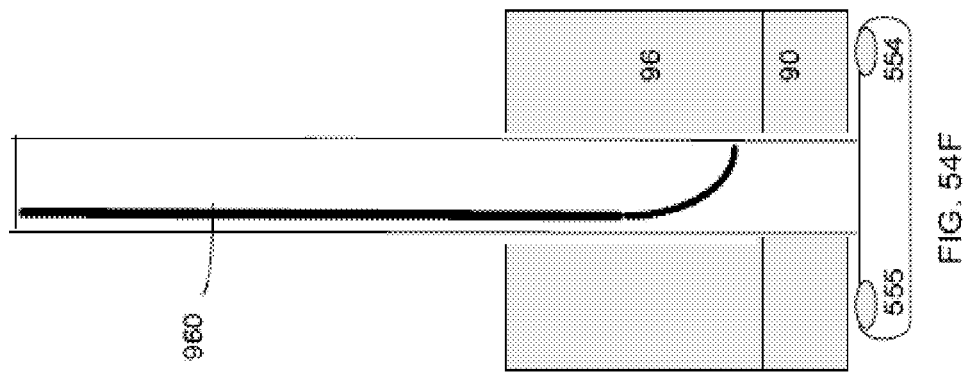
FIG. 54F is a cross section schematic of the suture placement device of FIG. 54E pulled upward against the abdominal wall.
Figure 54E:
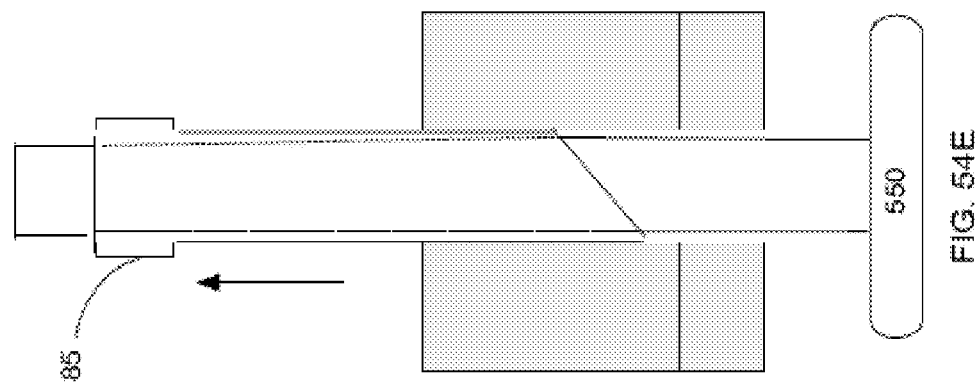
FIG. 54E is a cross section schematic of the suture placement device of FIG. 54D, with the trocar port being removed over the device.
Figure 54D:
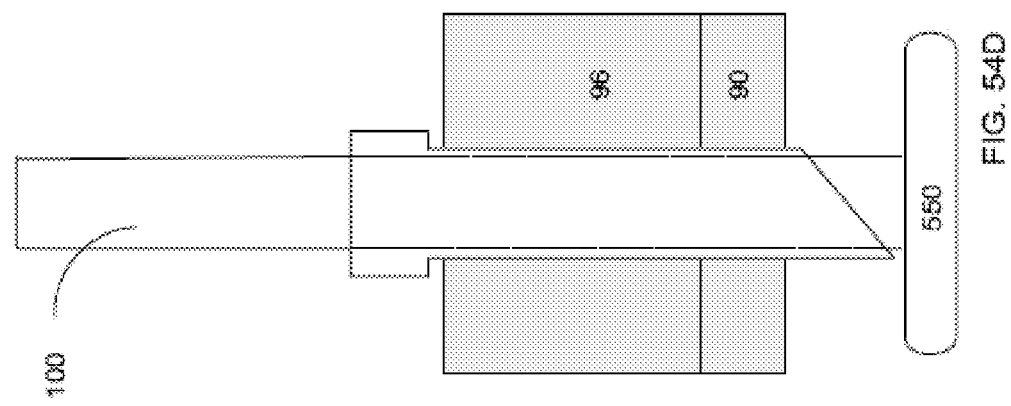
FIG. 54D is a cross section schematic of the suture placement device of FIG. 54C fully inserted in to the trocar port, and the pivot bar in an extended position.
Figure 54L:
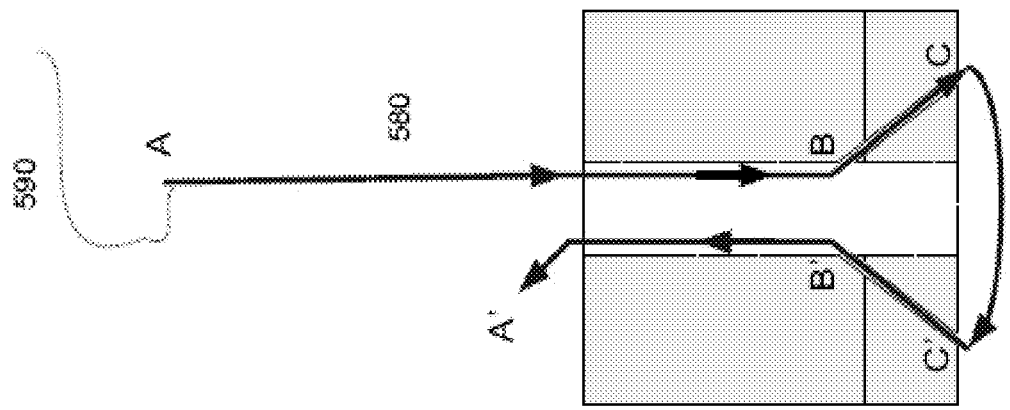
FIG. 54L is a cross section schematic of the suture placement device of FIG. 54I showing a stylet routed through the stylet path segments with an alternative exit path.
Figure 54K:
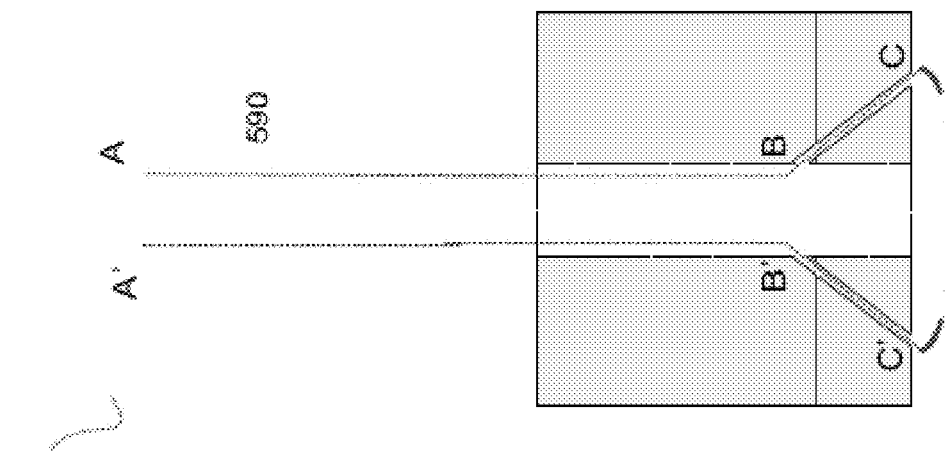
FIG. 54K is a cross section schematic of the suture placement device of FIG. 54J showing a suture pulled through the stylet path segments.
Figure 54J:
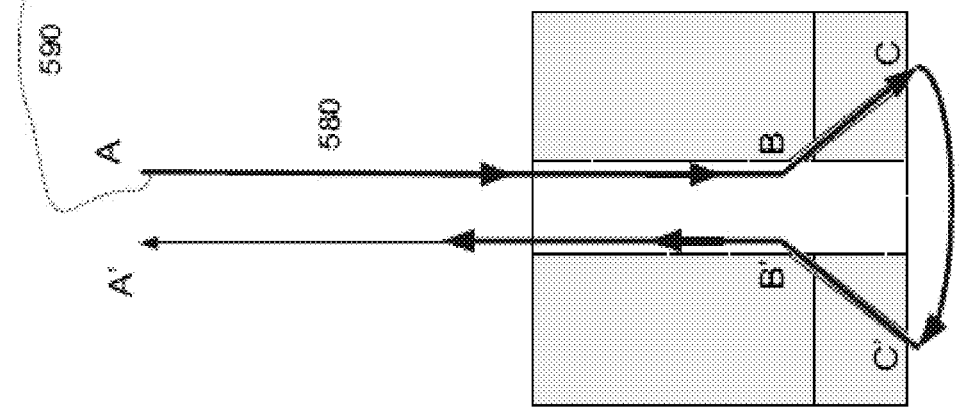
FIG. 54J is a cross section schematic of the suture placement device of FIG. 54I showing a stylet routed through the stylet path segments.
Figure 54P:
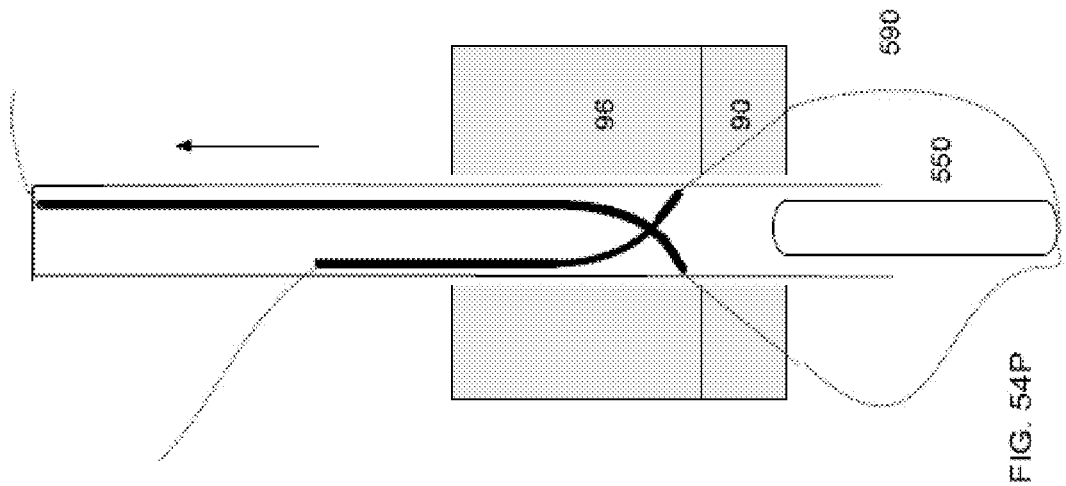
FIG. 54P is a cross section schematic of the suture placement device of FIG. 54O showing the pivot bar folded and the suture released from the pivot bar.
Figure 54O:
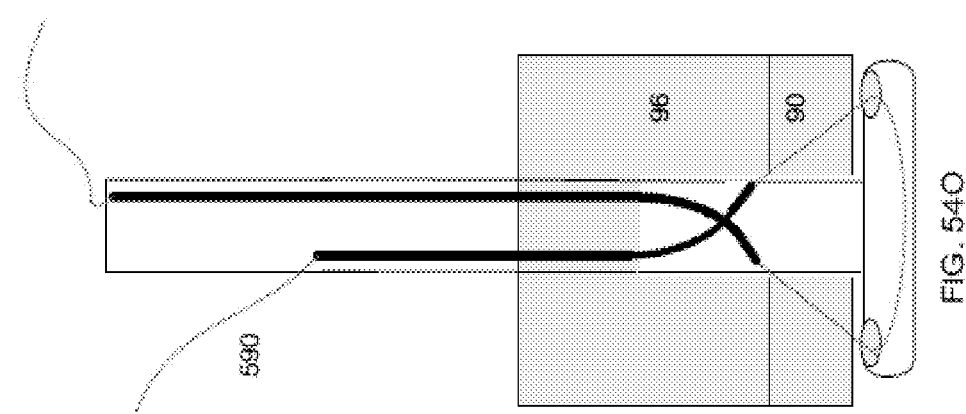
FIG. 54O is a cross section schematic of the suture placement device of FIG. 54M showing the stylet guides retracted.
Figure 54R:
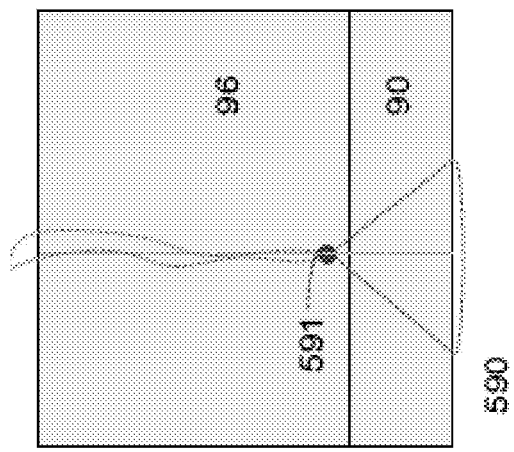
FIG. 54R is a cross section schematic of the suture of FIG. 54S tied to reapproximate the trocar port opening.
Figure 54Q:
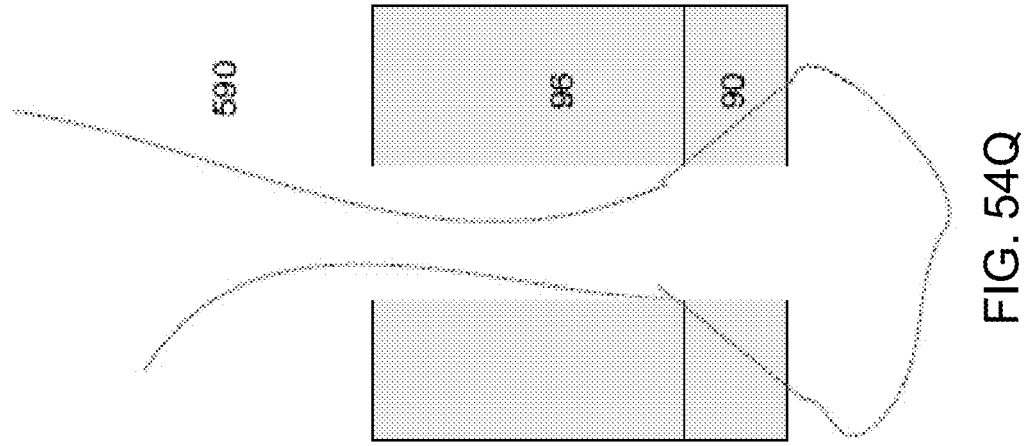
FIG. 54Q is a cross section schematic of the suture placement device of FIG. 54P removed, leaving the suture in place.
Figures 55, 56:
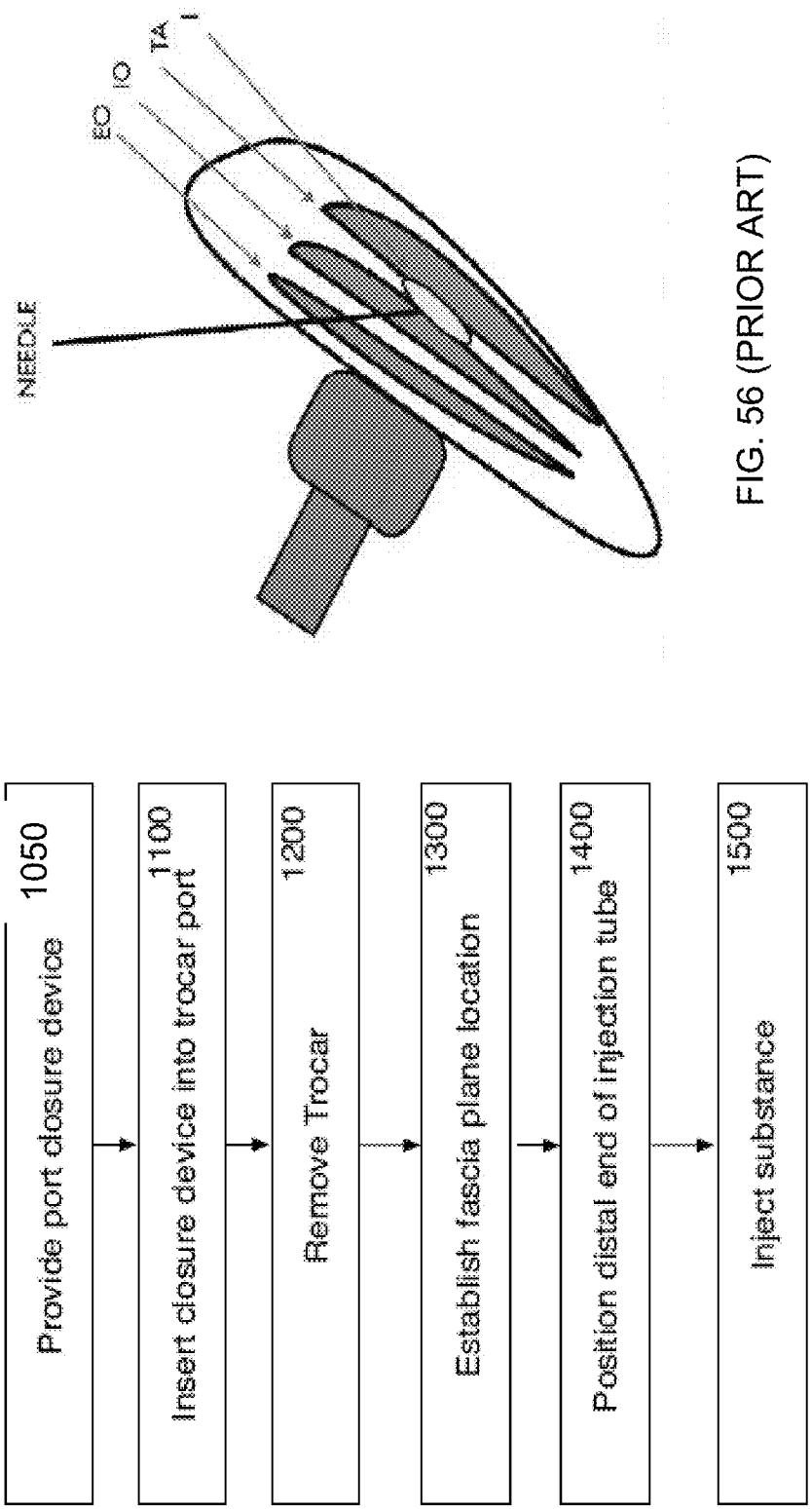
FIG. 55 is a flow chart that summarizes a general method for injecting a substance at a desired depth within the fascia.
FIG. 56 is a prior art illustration of a TAP block
Figure 57A:
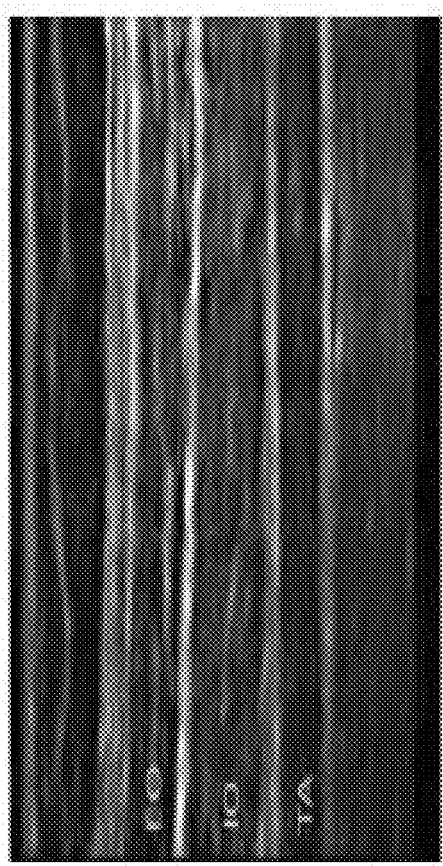
FIG. 57A is a prior art illustration of skin; subcutaneous tissue; fat; and the external oblique (EO), internal oblique muscle (IO), the transversus abdominis (TA) muscles.
Figure 57B:
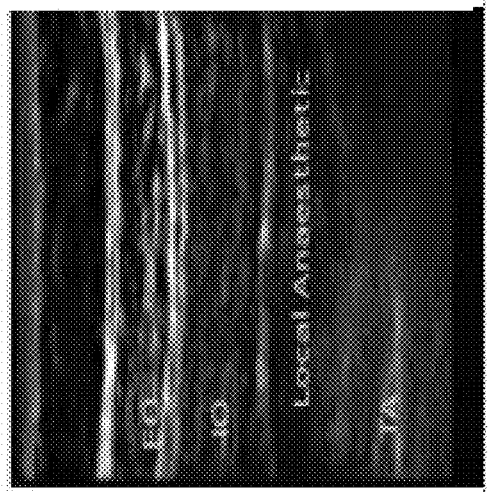
FIG. 57B is a prior art illustration showing the desired positioning of a TAP block between the internal oblique muscle (IO), and the transversus abdominis (TA) muscles.
Figure 58:
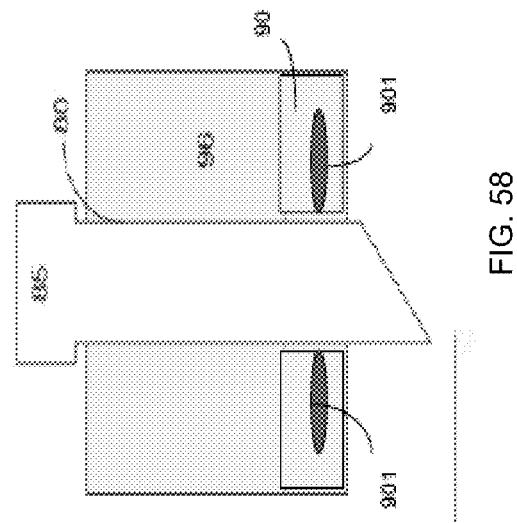
FIG. 58 is a cross section view of a trocar port and trocar port site showing desired injection plane for TAP block.

FIG. 47A is a side view of a first stylet guide 560 for the suture placement with the guide in a retracted position. FIG. 47B is a side view of the first guide 560 in an extended position when the guide plunger is depressed. FIG. 47C is a detailed side view of the proximal end of the first guide 560 showing a slot 562 on the guide. In other examples, slots on the guides are not required and the suture remains in position as the device is removed.

In the refracted position, the distal end portion 564 of the first guide 560 is confined within a directional channel within the body of the suture placement device. When the guide plunger is depressed, the distal portion 564 of the guide is pushed out of the body in a direction that will penetrate fascia and intercept the first receptor port 554 of the pivot bar. After placement of the suture, the first guide is retracted back into the body by the guide plunger so that the suture placement device may be removed. Suture remains in place as the first guide is retracted. In one example, the guide has a suture release slot to facilitate separation the release of the suture from the guide. In other examples, the suture release slot is not necessary, and the suture will remain in place as the guide is retracted.

Guides were initially constructed of nitinol, and subsequent testing has shown that stainless steel guides have worked effectively.

Body

FIG. 49A is a side perspective view of the outside of a first body section 510a for the suture placement device. FIG. 49B is a side perspective view of the inside of a second body section 510a for the suture placement device. FIG. 49C is a side view of the inside of the first body section of FIG. 49B. FIG. 49D is a bottom perspective view of the inside of the first body section of FIG. 49A.

Features for both body sections are similar so that internal features are created by mating the two body portions. The body sections include lower recess portions 511 to house the pivot bar. The pivot bar pivots with respect to pivot hole 518, and is moved by actuation arms with respect to slot 519.

The first guide is housed in a first guide channel 512 which includes first directional channel 513. The second guide is housed in a second guide channel 514 which includes second directional channel 515. In this example, the outside edges of the housing sections are recessed to provide suture release slots 517. In other examples, suture release slots are not provided in along the body, and the suture remains in place as the suture placement device is removed.

Pivot Bar Actuation Slides

FIG. 50A is a side perspective view of a first pivot bar actuation slide 520 which includes a shaft 522 extending from grip 521 to pin retainer 523. As the pivot bar actuation slide is pressed downward with respect to the housing, the shaft 522 forces the in retainer 523 to rotate the pivot bar wing to an open position. FIG. 50B is a side perspective view of a second pivot bar actuation slide 524 which includes a shaft 526 extending from grip 525 to pin retainer 527. In one example, the first and second actuation slides are pinned together so that both slides may be operated by a single thumb of the user.

In one example, the pivot bar is spring loaded in a normally-extended position. The suture placement device is positioned in a trocar port with the pivot bar in a retracted position, aligned with the device. When the pivot bar reaches the cavity below the fascia, the spring-load will force the pivot bar to pivot to an open and extended position, and the actuation arms will move up and provide a visual indication that the suture placement device is in a proper position. The trocar port can then be removed.

Assembled Device

FIGS. 51 and 52 are side perspective views of the suture placement device 105 with the pivot bar 550 in a retracted position.

Suture release slot 517 is shown between body sections 510a and 510b. First guide exit port 501 is shown at the lower end of suture release slot 517. The guide plunger 540 is in a raised position so that the first guide and second guide (not shown) are in retracted orientations inside the body. Pivot bar actuation slides 520 and 524 are shown in a retracted position.

FIG. 53 is a top perspective view of the assembled suture placement device 105 showing pivot bar receptor ports 554 and 555 and suture release slot 553. The guide plunger 540 includes stylet ports 542 and 543.

TAP or Other Substance Introduction

Figure 59C:
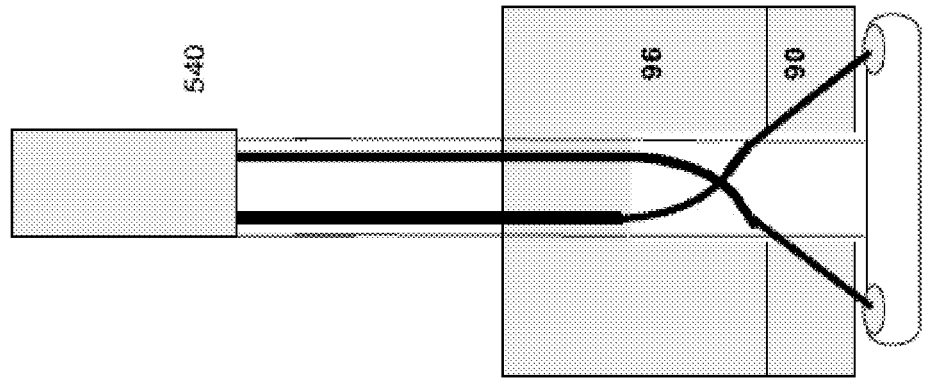
FIG. 59C shows the guide plunger of FIG. 59A fully depressed so that the stylet guide tips are fully deployed.
Figure 59B:
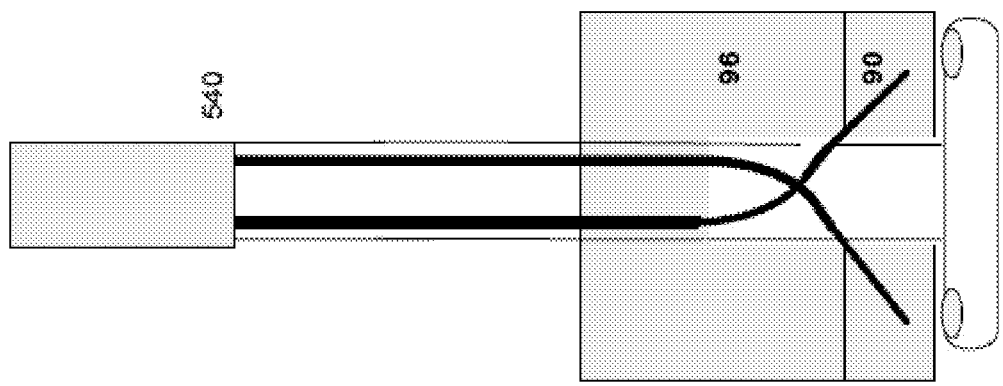
FIG. 59B shows the guide plunger of FIG. 59A partially depressed so that the stylet guide tips are positioned at an optional second distance from the fascial plane reference element.
Figure 59A:
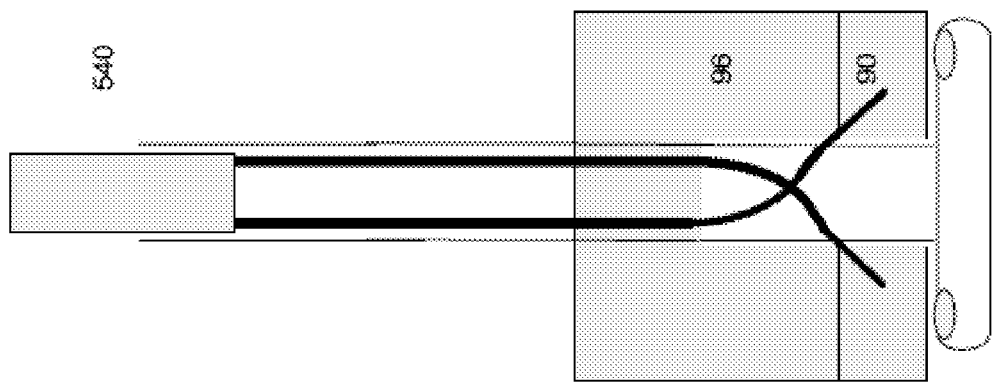
FIG. 59A shows a guide plunger for a suture placement device partially depressed so that stylet guide tips are positioned at a first distance from the fascial plane reference element.

In this example, the pivot bar 550 serves as a fascial plane reference element and one or both stylet guides serves as an injection tube. A single guide plunger 540 may be used to set the depth of both stylet guides. The desired partial deployment depth of the distal end of the stylet guides may be set with a fixed mechanical stop or an adjustable mechanical stop on the guide plunger. FIG. 59A shows the guide plunger 540 partially depressed so that the stylet guide tips are positioned at a first distance from the fascial plane reference element. FIG. 59B shows the guide plunger 540 partially depressed so that the stylet guide tips are positioned at an optional second distance from the fascial plane reference element. FIG. 59C shows the guide plunger 540 fully depressed so that the stylet guide tips are fully deployed.

FIG. 60A shows shows the guide plunger 540 partially depressed according to a first color band or scale reading on the housing, so that the stylet guide tips are positioned at a first distance from the fascial plane reference element. FIG. 60B shows the guide plunger 540 partially depressed according to a second color band or scale reading on the housing, so that the stylet guide tips are positioned at an optional second distance from the fascial plane reference element. FIG. 60C shows the guide plunger 540 fully depressed so that the stylet guide tips are fully deployed.

In some cases, a single stylet guide can provide a single injection, and the injected substance will spread or migrate completely around a trocar port site. In other cases, a two stylet guides can be used to inject a substance on opposite sides of a trocar port site. An adapter may be provided to simultaneously introduce a substance or mixture to both stylet guides.

Example

Reusable Metal Suture Placement Device with Proximal Stylet Ports

FIGS. 43-53 describe a reusable suture placement device that may be provided as a metal housing and metal pivot bar. In this example, the stylet ports 542 and 543 are located at the proximal end of the guide plunger.

Example

Reusable Suture Placement Device with Side Stylet Ports

In this example, the stylet ports are provided on the side of the housing in order to shorten the suture path and decrease the time required to route a stylet through the suture path.

Example

Reusable Suture Placement Device with Proximal and Side Stylet Ports

In this example, an entry stylet port is provided on the proximal end of the device for convenient placement of the stylet, and an exit stylet port is provided on the side of the housing in order to shorten the suture path and decrease the time required to route a stylet through the suture path. In this example, the distance between the proximal stylet entry port to the first receptor port on the pivot bar (path segment A-B-C in FIG. xx) is longer than the distance between the first receptor port and the side stylet exit port (path segment C-C'-B'-A' in FIG. xx). The shorter exit path length facilitates the use of a plunger in suture loading tools as described below.

Example

Disposable Suture Placement Device with Pivot Bar

Figure 63:
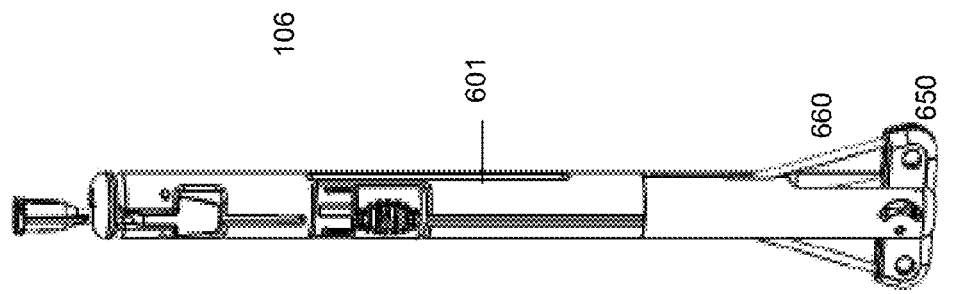
FIG. 63 is a side perspective view of the suture placement device of FIG. 61.
Figure 62:
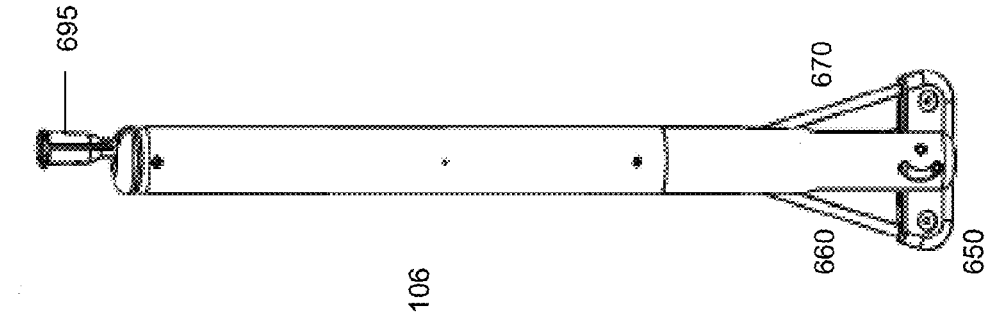
FIG. 62 is a rear view of the suture placement device of FIG. 61.
Figure 61:
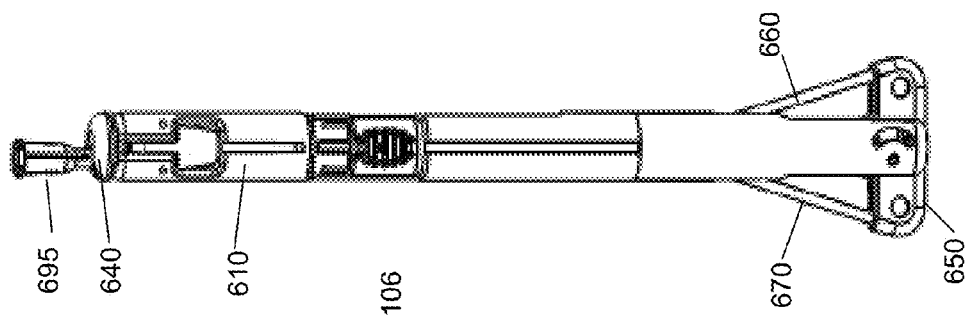
FIG. 61 is a front view of a plastic suture placement device.

FIGS. 61-63 are a front view, rear view, and side perspective view of a plastic suture placement device 106 with a leur fitting 695 for a TAP procedure as described below. A leur lock may be removably or permanently attached to the proximal entry port to permit injection of an analgesic or other substance through the proximal stylet entry port and into a stylet guide.

FIG. 64 is an exploded side perspective view of the suture placement device 106 showing a plunger 640, stylet guides 660 and 670, an upper body 610, lower body sections 616*a* and 616*b*, and pivot bar sections 650*a* and 650*b*.

FIGS. 65 and 66 are a front view and side perspective view of the upper body portion 610 of the plastic suture placement device of FIG. 61. The upper body portion includes recessed area 618 for a pivot bar knob, and recessed area 619 for a guide latch. The stylet exits through a stylet exit port 643 within slot 601.

Figure 68:
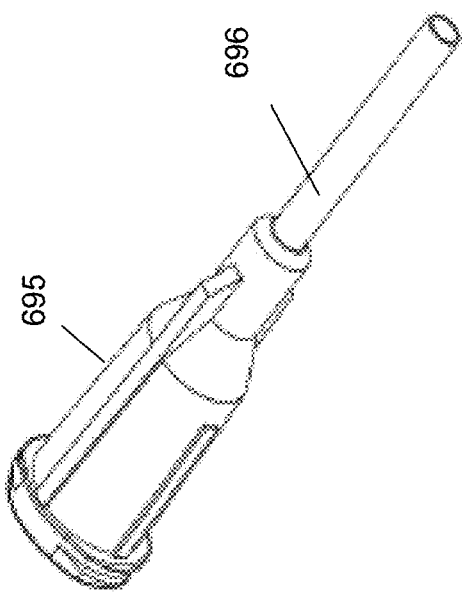
FIG. 68 is a side perspective view of a luer fitting and extension tube which may be inserted into the plastic suture placement device of FIG. 61.
Figure 67:
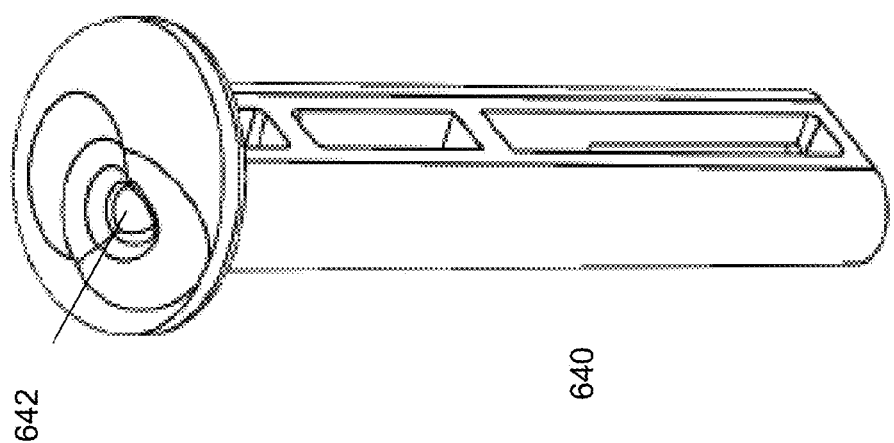
FIG. 67 is a top perspective view of the plunger of the plastic suture placement device of FIG. 61.

FIG. 67 is a top perspective view of the plunger 640 with stylet entry port 642. In this example, a luer fitting 695 with an extension tube 696, as shown in FIG. 68, may be inserted into the stylet entry port 642. Depressing plunger 640 pushes connector tubes 685 and 686 and forces stylet guides 660 and 670 from a retracted to a deployed position. Depressing latch 630 permits plunger return spring 646 and latch spring 688 to push the plunger 640 and force stylet guides 660 and 670 from their deployed position back to a retracted orientation.

Figure 69:
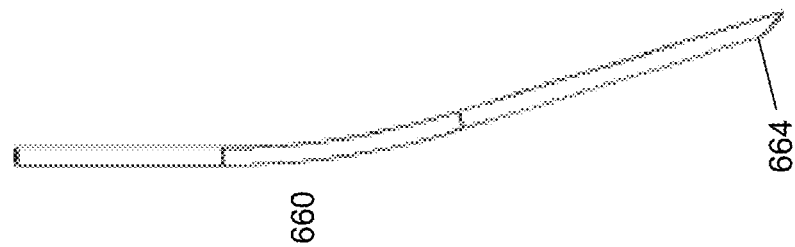
FIG. 69 is a front view of stylet guides of the suture placement device of FIG. 61.

FIG. 69 is a front view of stylet guides 660. FIG. 64 shows a first stylet guide 660 and a first connector tube 685. A connector tube may be used where the bendable portion of the stylet guides are provided in a relatively expensive material such as nitinol. Testing has established that lower cost stainless steel guides are effective, so single piece stylet guides may be used in lieu of the two part stylet guide and connector tube design.

In this example, the distal end 664 of the first stylet guide and the distal end of the second stylet guide are tapered outward with respect to centerline of the housing. This outward tapering has provided consistent mating with the receptor ports on the pivot bar.

Figure 71:
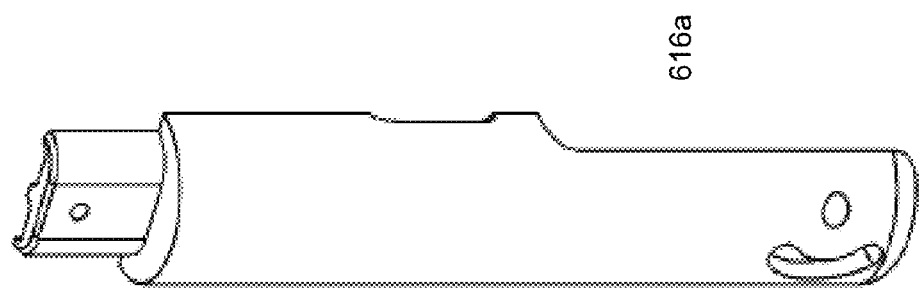
FIG. 71 is a front perspective view of the exterior of lower body section of the suture placement device of FIG. 61.
Figure 70:
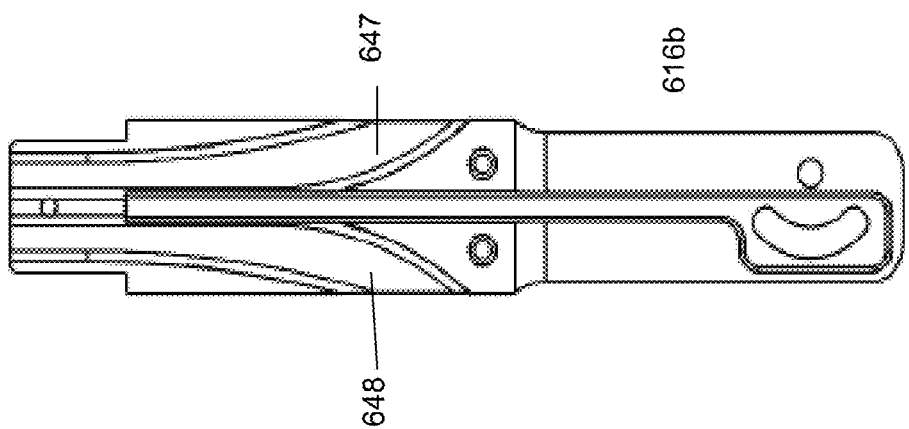
FIG. 70 is a front view of the interior of lower body section of the suture placement device of FIG. 61.

In this example, the lower body is provided in lower body sections 616*a* and 616*b*. FIG. 70 is a front view of the interior of lower body section 616*b*. Stylet guides 660 and 670 are directed through stylet guide channels 647 and 648 so that the distal ends of the guides intercept the receptor ports on the pivot bar. FIG. 71 is a front perspective view of the exterior of lower body section 616*a*.

In this example, the pivot bar is provided in sections 650*a* and 650*b*. FIG. 72 is a front perspective view of the pivot bar section 650*b* showing portions of receptor ports 654 and 655, suture release slot 653, and pivot bar channel 651. FIG. 73 is a front perspective view of the assembled pivot bar 650 with pivot bar rivet 652. The pivot bar is rotated by moving the pivot bar actuation knob 625 which moves a single pivot bar actuation rod 620. The pivot bar actuation rod pulls or pushes the pivot bar rivet 652, which causes the pivot bar to rotate with respect to pivot bar roll pins 657*a* and 657*b*. In this example, a pivot bar actuation spring 626 biases the pivot bar to an extended position.

Example

Suture Placement Device with Disposable or Replaceable Guides

In this example, a metal or other reusable suture placement device body is hinged to provide access to the stylet guides, so that the stylet guides may be removed and replaces. In other examples, the pivot bar may be removed and replaced.

Example

Suture Placement Device Used as Obturator

In this example, a suture placement device with a pivot bar is adapted to serve as an obturator and a closure device. FIG. 74A shows a suture placement device that is configured to be used as an obturator 701. In this example, a removable head 710 is placed over the suture placement device and trocar to secure the device as it is used to pierce the fascia during initial placement of the trocar port. The suture placement device/obturator is placed inside the trocar port (not shown) during this operation. The leading edge 721 of the pivot bar on the suture placement device is sharp to penetrate the fascia during trocar installation. FIG. 74B shows the suture placement device/obturator of FIG. 74A with the head 710 removed so that the device is configured to be used as a suture placement device. FIG. 74C shows the pivot bar 720 deployed when the device of FIG. 74B is inserted into a trocar port (not shown). The pivot bar has a sharp first tip 721 and a rounded second tip 722. In one example, the sharp first tip 721 is rotated 180 degrees after its use as an obturator tip so that the rounded second tip 722 becomes the leading tip when the suture placement device is re-inserted into a trocar port to serve as a closure device.

Example

Suture Placement Device for 10 Mm Trocars

In this example, the suture placement device is sized to fit inside a 10 mm or larger diameter trocar, so that the trocar can be removed over the device.

Example

Suture Placement Device for 8 Mm Trocars

Figure 75C:
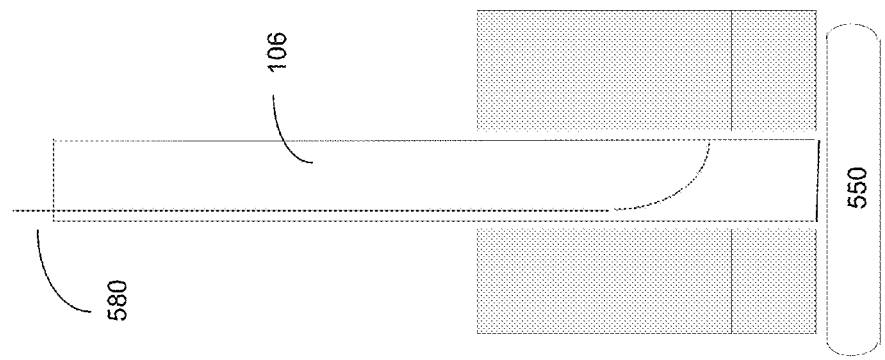
Figure 75B:
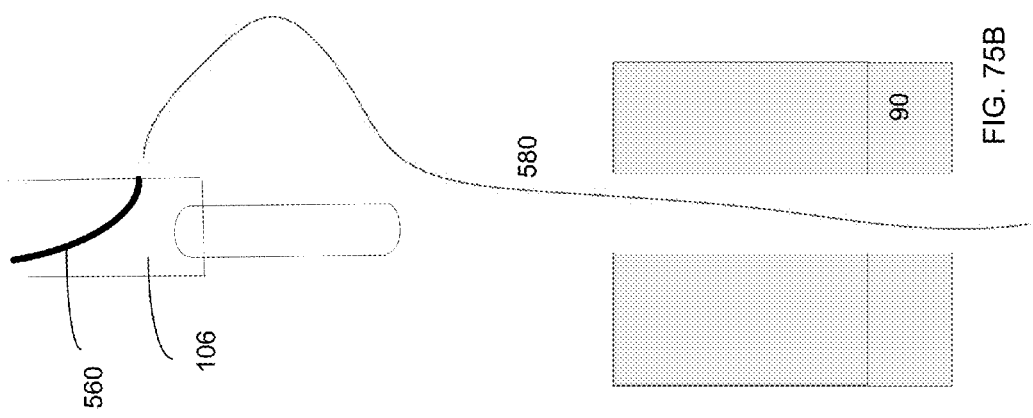
Figure 75A:
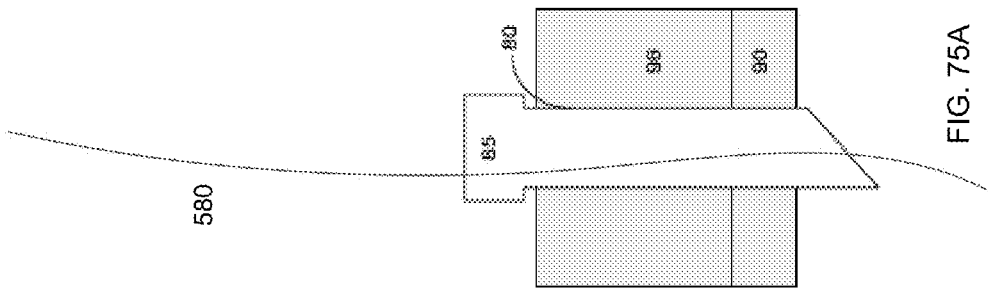

In this example, a suture placement device designed for insertion into a 10 mm trocar is inserted into an 8 mm trocar port site. Referring to FIG. 75A, the proximal end of a stylet 580 is inserted into the trocar. The trocar is then removed over the stylet. After removing the trocar, the distal end of the stylet 580 is inserted into the distal end of stylet guide 560 of a suture placement device 106 without deploying the stylet guides as shown in FIG. 75B. The stylet is pushed through the stylet guide 560 until the distal end of the stylet is pushed out of the stylet entry port. The stylet is then grasped and used as a guide wire as the suture placement device is inserted into the trocar port site. Referring to FIG. 75C, the pivot bar 550 is deployed and a slight upward pressure is applied to the suture placement device as the stylet is removed until the proximal end of the stylet 580 is drawn into the stylet guide 560. The stylet guides are then deployed and the stylet is fed through the device as described above.

DESCRIPTION OF EMBODIMENT

Suture Loading Devices

In the examples described above, a stylet is used to route a suture through the suture path. In various device testing, a trocar port site can be closed in about 60 seconds or less, with about 10-30 seconds required to route a stylet. Several example suture loading devices have been developed in order to reduce the required closure time by reducing stylet load time.

FIGS. 76A-76E are cross section schematics illustrating a suture loading device 750 to route a suture through a suture path.

FIGS. 76A-76B illustrate a suture loading technique using a suture loading device 750. In this example, a flexible leading shaft portion 762 is inserted into a stylet guide entry port. In a first step, as illustrated by FIG. 76A, the flexible leading shaft portion 762 is contained within a stylet guide of the suture placement device and extends from below point A at the proximal end of the suture placement device to point C at the first receptor port on the pivot bar. This positioning of the flexible leading shaft portion 762 within the stylet guide protects the flexible leading shaft portion to minimize kinking FIG. 76B illustrates a more rigid push shaft section 764 of the suture loading device 750 pushed downward with handle 780 so that the distal end 765 of the push shaft section 764 is at or near point C. In this example, the push shaft section is flexible enough to be pushed through the guide from point B to point C, but not flexible enough to make the bend in the suture path at point C. In this example, the path A-B-C is longer than the path C-C'-B'-A' so that pushing the push shaft section to point C forces the flexible leading shaft portion 762 through path C-C'-B'-A' thereby causing the distal end 763 of the flexible leading shaft portion 762 to emerge from the suture placement device at point A'. As described below, the suture may either be grasped by the suture loading device and pulled back through the path A'-B'-C'-C-B-A as the suture loading device 750 is withdrawn, or the suture may have been carried through the suture path so that the suture can be released and held while the suture loading device is withdrawn.

In one example, suture capture is performed on the flexible leading shaft portion 762 before the suture loading device is inserted into the suture placement device. After the flexible leading shaft portion 762 emerges from the suture placement device at point A', the the suture may be removed. The suture loading device 750 is then withdrawn while the suture end is held at point A'.

In another example, suture capture is performed after the suture loading device is inserted into the suture placement device and the flexible leading shaft portion 762 emerges from the suture placement device at point A' as illustrated by FIG. 76B.

In FIG. 76C, the suture loading device is partially withdrawn from the suture placement device so that the first end of the suture is between points A' and B'.

Figure 76E:
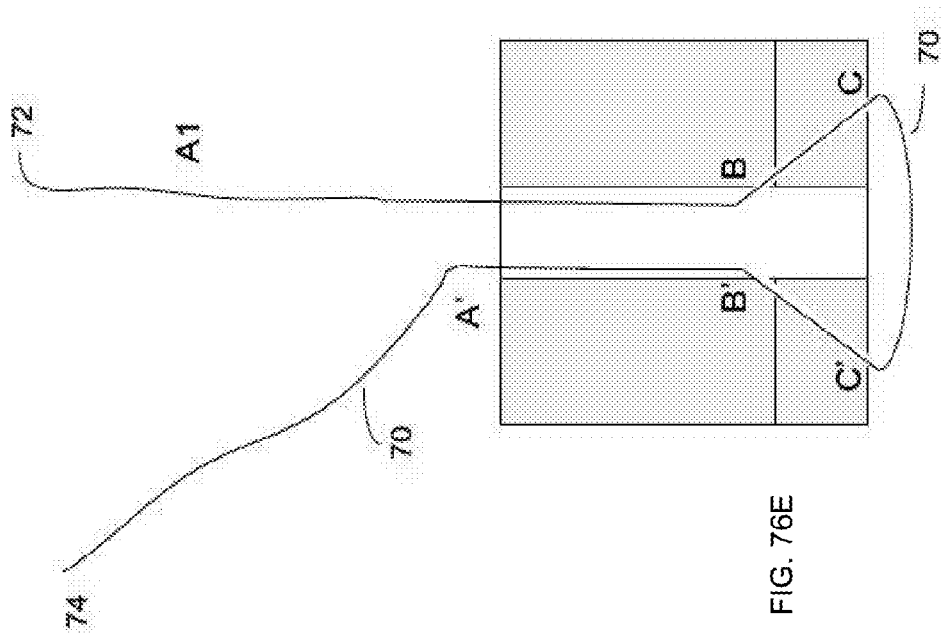
Figure 76D:
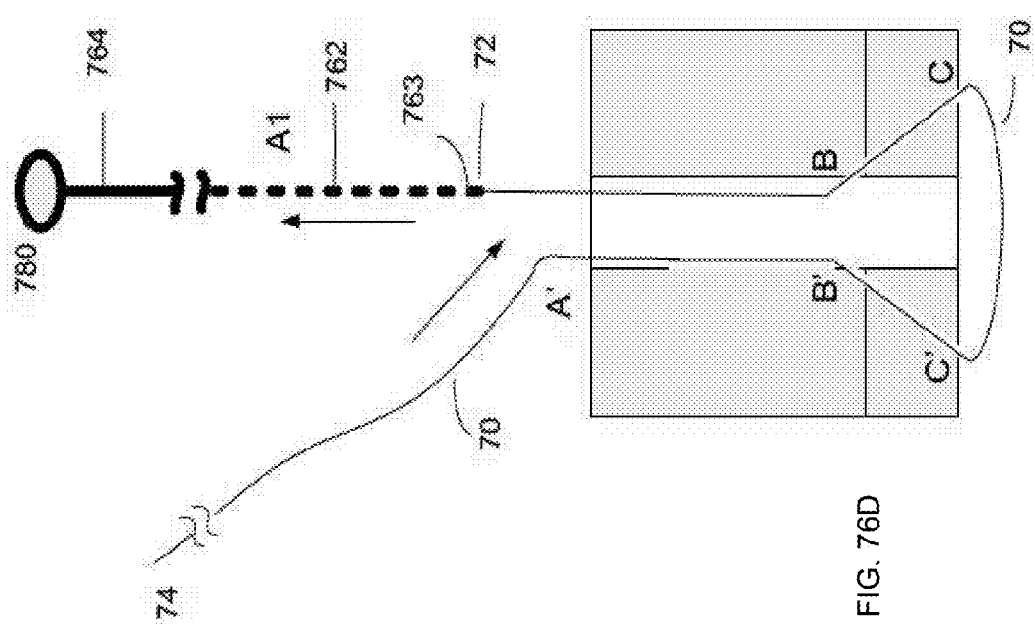

In FIG. 76D, the suture loading device is almost withdrawn from the suture placement device so that the first end of the suture is between points A and B.

In FIG. 76E, the suture loading device is fully withdrawn from the suture placement device so that the first end of the suture has been pulled out of the suture placement device at point A; and the hand has been depressed to release the suture.

Example

Suture Loading Device

FIG. 77A is a front perspective view of a suture loading device 751 that is used to pull a suture 70 though a suture path. The suture loading device 751 has a two-part shaft 760 comprising a flexible leading shaft portion 762 and a push shaft section 764.

Figure 77B:
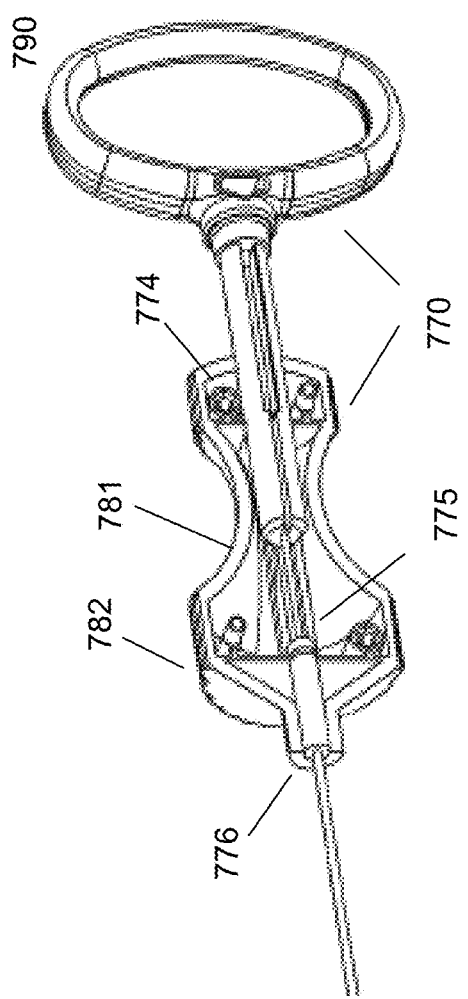

FIG. 77B is a detailed cross section view of a handle assembly 770 with a handle 790 and a collar 782. The collar 782 has a handle opening 774, an interior chamber 775, and a shaft opening 776. In this example, the collar includes a circumferential finger recess 781 configured so that the collar can be grasped between two fingers as the handle 782 is depressed with the palm of the hand or thumb.

FIG. 77C is a detailed view of the distal end 763 of suture loading device 751 with the device in its normally-closed orientation.

FIG. 77D is a detailed cross section view of a handle assembly 770 with the handle 790 in a suture capture/release orientation.

FIG. 77E is a detailed view of the distal end of suture loading device 751 with the device in a suture-capture orientation. In this example, two wires 752 and 754 are routed from the handle and through the two part shaft. The proximal end of the wires are attached to distal end 792 of the handle, so that as the handle is depressed toward the collar, the distal end of the two wires are extended past the distal end 763 of the flexible leading shaft portion 762. The distal ends of the two wires are joined with a ball 755 that has a diameter greater than the inside diameter of the flexible leading shaft portion 762. When the wires are retracted, the ball 755 serves to assist in pushing the flexible leading shaft portion through the suture path. When the distal end of the wires and ball are extended past the distal end of the distal end 763 of the flexible leading shaft portion 762, a portion of a suture may be placed over the exposed wires so that when the handle is released, the ball 755 will be retracted to the distal end 763 of the flexible leading shaft portion and will secure the suture between the ball 755 and the distal end 763 of the flexible leading shaft portion 762. The suture may be released by moving the handle back to the capture/release orientation.

In one example, the suture may be captured on the flexible leading shaft portion 762 before the suture loading device is inserted into the suture placement device. After the flexible leading shaft portion 762 emerges from the suture placement device at point A', the handle is depressed so that the suture may be removed. The suture loading device 751 is then withdrawn while the suture end is held.

In another example, suture capture is performed after the suture loading device is inserted into the suture placement device and the flexible leading shaft portion 762 emerges from the suture placement device at point A'. The handle is depressed so that the suture may be attached, the suture loading device is withdrawn from the suture placement device, and the handle is depressed again so that the suture may be removed.

Stylet Ball Tip

Stylet loading has been improved by modifying the lead tip of a stylet by attaching a ball such as shown in FIG. 77C. The ball appears to minimize stylet hangups in the suture path.

Example

Suture Loading Device

FIG. 78A is a front perspective view of another suture loading device 756. The suture loading device 756 has a handle assembly 771, and a two-part shaft 760 comprising a flexible leading shaft portion 762 and a push shaft section

764. The flexible leading shaft portion 762 has a gap 753 that is expanded or contracted by operating the handle.

FIG. 78B is a detailed cross section view of a handle assembly 771.

FIG. 78C is a detailed view of the distal end portion of suture loading device 756 with gap 753 opened to capture a suture between wires 752 and 754 which are forced apart as the handle is operated. The suture is also released by opening gap 753.

Stylet Plunger

In another example, a portion of a stylet is loaded into the suture placement device, and a plunger 791 such as illustrated in FIG. 79 is used to push the leading portion of the stylet through the suture path. The plunger in FIG. 79 comprises a handle 793, and a relatively rigid shaft 794.

While exemplary embodiments of the invention have been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A suture placement device for the placement of a suture after the removal of an endoscopic trocar port, the suture placement device comprising
   a cannular housing configured to be insertable into a trocar port of a determined width, the cannular housing having a diameter that permits the trocar port to be removed after the device is positioned in the trocar port, the cannular housing comprising
      a proximal portion and a distal portion, and having a longitudinal axis extending from the proximal portion to the distal portion;
   an extension mechanism movably coupled to the distal portion of the cannular housing, the extension mechanism comprising:
      a first segment with a first terminus and a first receptor port in proximity to the first terminus,
      a second segment with a second terminus and a second receptor port in proximity to the second terminus, and
      the extension mechanism being movable between
         a folded position, with the first segment and second segment being oriented for passage through the trocar port, and
         an extended position, rotated 90 degrees relative to the longitudinal axis
      the first segment and second segment providing a distal suture passage, with a suture release slot, extending from the first receptor port to the second receptor port; and
   a first stylet guide comprising
      a proximal end,
      a distal end, and
      a stylet guide suture path segment between the proximal end and the distal end, the first stylet guide being movable between
         a retracted position oriented for passage through the trocar port, and
         a deployed position where a portion of the first stylet guide extends from the housing to the first receptor port of the extension mechanism; and
   a second stylet guide comprising
      a proximal end,
      a distal end, and
      a stylet guide suture path segment between the proximal end and the distal end, the second stylet guide being movable between
         a retracted position oriented for passage through the trocar port, and
         a deployed position where a portion of the second stylet guide extends from the housing to the second receptor port of the extension mechanism.

2. The suture placement device of claim 1 wherein the extension mechanism is a pivot bar.

3. The suture placement device of claim 1 further comprising an extension mechanism deployment mechanism comprising
   a thumb latch or finger latch;
   a return spring; and
   a lock.

4. The suture placement device of claim 1 wherein the cannular housing further comprises
   a first stylet guide alignment channel; and
   a second stylet guide alignment channel.

5. The suture placement device of claim 1 wherein the first stylet guide and the second stylet guides are flexible tubes.

6. The suture placement device of claim 1 further comprising a stylet guide deployment mechanism.

7. The suture placement device of claim 6 wherein the stylet guide deployment mechanism further comprises
   a thumb-driven actuator;
   a first lock configured to hold the first and second stylet guides in a fully deployed position; and
   a return spring.

8. The suture placement device of claim 7 wherein the stylet guide deployment mechanism further comprises
   a second lock configured to hold the first stylet guide in a partially deployed position.

9. The suture placement device of claim 1 further comprising
   a suture insertion element configured to be at least partially insertable into the first stylet guide.

10. The suture placement device of claim 9 wherein the suture insertion element comprises a stylet.

11. The suture placement device of claim 10 wherein the suture insertion element further comprises
    a plunger configured to advance the stylet.

12. The suture placement device of claim 11 wherein the plunger further comprises
    a suture attachment feature.

13. The suture placement device of claim 12 further comprising
    a tip feature.

14. The suture placement element of claim 9 further comprising a flexible lead portion having a proximal end and a free distal end, the free distal end having an internal diameter; and a plunger portion having a proximal end and a distal end, the distal end attached to the proximal end of the flexible lead portion.

15. The suture placement device of claim 14 further comprising a handle attached to the proximal end of the plunger portion;

a first wire and a second wire routed from the handle through the plunger portion and through the flexible lead portion, the first wire and second wire having a proximal end at the handle and a distal end;

a connector securing the distal ends of the first wire and second wire, the connector being larger than the internal diameter of the flexible lead portion;

an actuator connected to the first wire and the second wire, the actuator having a first resting position where the connector is held in proximity to the distal end of the flexible lead portion, and an extended position where the connector is extended from the distal end of the flexible lead portion.

16. The suture placement device of claim 1 wherein the first receptor port of the extension mechanism is positioned approximately one centimeter from the cannular housing; and the second receptor port of the extension mechanism is positioned approximately one centimeter from the cannular housing and opposed to the first receptor port.

17. The suture placement device of claim 1 wherein the retracted position of the first stylet guide is within the cannular housing.

18. The suture placement device of claim 1 wherein the first stylet guide is movable between a retracted position, a partially deployed lockable position where the distal end of the first stylet guide is spaced apart from the first receptor port by a desired distance in the range of about 0.1 to 1.0 cm, and a fully deployed lockable position where the distal end of the first stylet guide is extended to the first receptor port of the extension mechanism; and the proximal end of the first stylet guide is configured to be in fluid communication with a syringe, needle, or injection tube.

19. The suture placement device of claim 1 wherein the first terminus of the extension mechanism is a tapered to provide a means for tissue-spreading or tissue-penetration.

* * * * *